United States Patent
Scaife

(10) Patent No.: US 11,241,467 B2
(45) Date of Patent: Feb. 8, 2022

(54) COMPOSITION FOR TREATING ACNE

(71) Applicant: SKINTECH LIFE SCIENCE LIMITED, Middlesex (GB)

(72) Inventor: Michael C. Scaife, Charlotte, NC (US)

(73) Assignee: SKINTECH LIFE SCIENCE LIMITED, Hertfordshire (GB)

( * ) Notice: Subject to any disclaimer, the term of this patent is extended or adjusted under 35 U.S.C. 154(b) by 0 days.

(21) Appl. No.: 16/479,158

(22) PCT Filed: Jan. 19, 2018

(86) PCT No.: PCT/IB2018/000109
§ 371 (c)(1),
(2) Date: Jul. 18, 2019

(87) PCT Pub. No.: WO2018/134683
PCT Pub. Date: Jul. 26, 2018

(65) Prior Publication Data
US 2020/0138884 A1 May 7, 2020

Related U.S. Application Data

(60) Provisional application No. 62/448,808, filed on Jan. 20, 2017.

(51) Int. Cl.
*A61K 31/404* (2006.01)
*A61K 36/185* (2006.01)

(52) U.S. Cl.
CPC .......... *A61K 36/185* (2013.01); *A61K 31/404* (2013.01)

(58) Field of Classification Search
None
See application file for complete search history.

(56) References Cited

U.S. PATENT DOCUMENTS

| | | | |
|---|---|---|---|
| 5,665,367 A | 9/1997 | Burger et al. | |
| 9,180,117 B2 | 11/2015 | Alpert | |
| 9,351,958 B2 | 5/2016 | Alpert | |
| 9,907,785 B2 | 3/2018 | Alpert | |
| 10,966,958 B2 * | 4/2021 | Alpert | A61P 17/18 |
| 2003/0166583 A1 * | 9/2003 | Yoa-Pu Hu | A61K 31/015 514/27 |
| 2016/0051536 A1 * | 2/2016 | Gerk | A61K 31/7048 514/27 |
| 2016/0101083 A1 * | 4/2016 | Zeligs | A61K 33/24 424/490 |
| 2016/0367528 A1 * | 12/2016 | Alpert | A61P 17/08 |
| 2017/0231952 A1 * | 8/2017 | Alpert | A61P 17/00 514/29 |
| 2019/0000800 A1 | 1/2019 | Alpert | |
| 2019/0343798 A1 * | 11/2019 | Scaife | A61K 9/006 |

FOREIGN PATENT DOCUMENTS

| | | |
|---|---|---|
| CN | 103501772 A | 1/2014 |
| FR | 2908604 A1 | 5/2008 |
| WO | WO-2012130698 A1 | 10/2012 |
| WO | WO 2014/177123 * | 11/2014 |
| WO | WO-2014177123 A1 | 11/2014 |
| WO | WO-2018134683 A1 | 7/2018 |

OTHER PUBLICATIONS

Lake, B. et al. 3,3'-Diindolylmethane Induces CYP1A2 in Cultured Precision Cut Human Liver Slices. Xenobiotica 28(8)803-811, 1998. (Year: 1998).*
PCT/IB2018/000109 International Preliminary Report on Patentability dated Aug. 1, 2019.
PCT/IB2018/000109 International Search Report and Written Opinion dated May 24, 2018.
First Office Action issued for CN Application No. 201880019777.9, dated May 6, 2021, 14 pages.
He Fan1 et al., Inductive effect of quercetin, kaempferoland rutin on liver microsomal cytochrome P450 enzymes in rats, https://en/cnki.com.cn/Article_en/CJFDTotal-ZGYZ201009003 htm, 1 page.

* cited by examiner

*Primary Examiner* — Ralph J Gitomer
(74) *Attorney, Agent, or Firm* — Procopio, Cory, Hargreaves & Savitch LLP

(57) ABSTRACT

Described herein are pharmaceutical compositions comprising one or more modulators of a cytochrome 450 enzyme (CYP450) and substituted or unsubstituted diindolylmethane. Also described herein are methods for treating one or more skin conditions by administering a combination therapy comprising substituted or unsubstituted diindolylmethane and one or more modulators of CYP450. In particular, methods are disclosed for improving bioavailability and pharmacokinetic parameters of substituted or unsubstituted diindolylmethane following the combination therapy.

17 Claims, No Drawings

COMPOSITION FOR TREATING ACNE

CROSS-REFERENCE

This application claims the benefit of U.S. Provisional Application No. 62/448,808 filed on Jan. 20, 2017, which is incorporated by reference herein in its entirety.

BACKGROUND OF THE DISCLOSURE

Acne is a skin condition characterized by areas of blackheads, whiteheads, pimples, greasy skin, and possibly scarring. Rosacea is a chronic skin condition characterized by facial redness, small and superficial dilated blood vessels on facial skin, papules, pustules, and swelling. Acne and Rosacea are known to affect all ages.

SUMMARY OF THE DISCLOSURE

Disclosed herein, in some embodiments, are pharmaceutical compositions comprising a first component comprising a modulator of a CYP450 enzyme and a second component comprising a substituted or unsubstituted diindolylmethane, wherein said composition is for treating a skin condition. In some embodiments, the first component comprises about 100 mg to about 1000 mg of the modulator. In some embodiments, the second component comprises about 15 mg to about 100 mg of the substituted or unsubstituted diindolylmethane. In some embodiments, the second component comprises about 15 mg to about 25 mg, about 25 mg to about 35 mg, about 35 mg to about 45 mg, about 45 mg to about 55 mg, about 55 mg to about 65 mg, about 65 mg to about 75 mg, about 75 mg to about 85 mg, or about 85 mg to about 100 mg of the substituted or unsubstituted diindolylmethane. In some embodiments, the pharmaceutical composition further comprises a third component comprising a substituted or unsubstituted retinoic acid based compound. In some embodiments, the third component comprises about 100 µg to about 1000 µg of the substituted or unsubstituted retinoic acid based compound. In some embodiments, the CYP450 enzyme comprises CYP1A1, CYP1A2, CYP2D6, CYP2C8, CYP2C9, CYP3A4, CYP2C19, CYP19A1, or combinations thereof. In some embodiments, the CYP450 enzyme comprises CYP1A2 and the first component comprises a modulator of the CYP1A2. In some embodiments, the modulator of the CYP1A2 comprises quercetin. In some embodiments, the modulator of the CYP450 enzyme comprises quercetin. In some embodiments, the first component comprises about 100 mg to about 1000 mg of the modulator of the CYP1A2. In some embodiments, the first component comprises about 100 mg to about 1000 mg of the quercetin. In some embodiments, the first component comprises about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg of the quercetin. In some embodiments, the first component comprises about 400 mg to about 500 mg of the quercetin. In some embodiments, the second component comprises about 15 mg to about 25 mg, about 25 mg to about 35 mg, about 35 mg to about 45 mg, about 45 mg to about 55 mg, about 55 mg to about 65 mg, about 65 mg to about 75 mg, about 75 mg to about 85 mg, or about 85 mg to about 100 mg of the substituted or unsubstituted diindolylmethane. In some embodiments, the second component comprises about 30 mg to about 100 mg of the substituted or unsubstituted diindolylmethane. In some embodiments, the second component comprises about 45 mg of the substituted or unsubstituted diindolylmethane. In some embodiments, the pharmaceutical composition further comprises a third component comprising a substituted or unsubstituted retinoic acid based compound. In some embodiments, the third component comprises about 100 µg to about 1000 µg of the substituted or unsubstituted retinoic acid based compound. In some embodiments, the third component comprises about 100 µg to about 200 µg, about 200 µg to about 300 µg, about 300 µg to about 400 µg, about 400 µg to about 450 µg, about 450 µg to about 475 µg, about 475 µg to about 500 µg, about 500 µg to about 550 µg, about 550 µg to about 600 µg, about 600 µg to about 700 µg, about 700 µg to about 800 µg, about 800 µg to about 900 µg, about 900 µg to about 1000 µg of the substituted or unsubstituted retinoic acid based compound. In some embodiments, the third component comprises about 300 µg to about 500 µg of the substituted or unsubstituted retinoic acid based compound. In some embodiments, the third component comprises about 400 µg of the substituted or unsubstituted retinoic acid based compound. In some embodiments, the substituted or unsubstituted retinoic acid based compound comprises a vitamin A compound. In some embodiments, the first component, the second component, the third component, or combinations thereof, further comprise a pharmaceutically acceptable excipient. In some embodiments, the pharmaceutically acceptable excipient comprises sorbitol, mannitol, starch 1500, tri-calcium phosphate or combinations thereof. In some embodiments, the second component and the third component are in a same dosage form. In some embodiments, the first component and the second component are in a same dosage form. In some embodiments, the first component and the second component are in separate dosage forms. In some embodiments, a single dosage of the first component comprises about 300 mg to about 750 mg of the modulator. In some embodiments, a single dosage of the second component comprises about 30 mg to about 90 mg of the substituted or unsubstituted diindolylmethane. In some embodiments, the single dosage of the second component further comprises about 200 µg to about 1000 µg of a vitamin A compound. In some embodiments, a daily dosage of the first component comprises about 300 mg to about 2250 mg of the modulator. In some embodiments, a daily dosage of the second component comprises about 30 mg to about 270 mg of the substituted or unsubstituted diindolylmethane. In some embodiments, the daily dosage of the second component further comprises about 200 µg to about 3000 µg of a vitamin A compound. In some embodiments, the skin condition comprises acne, inflammation, rosacea, aging, or combinations thereof. In some embodiments, bioavailability of the substituted or unsubstituted diindolylmethane is increased by about 1-fold to about 100-folds compared to a control composition that does not comprise the first component. In some embodiments, Cmax of the substituted or unsubstituted diindolylmethane in plasma is increased by about 1-fold to about 100-folds compared to a control composition that does not comprise the first component. In some embodiments, AUC of the substituted or unsubstituted diindolylmethane in plasma is increased by about 1-fold to about 100-folds compared to a control composition that does not comprise the first component. In some embodiments, Tmax of the substituted or unsubstituted diindolylmethane in plasma is decreased by about 1-fold to about 100-folds compared to a control composition that does not comprise the first component. In some embodiments, percentage of the substituted or unsubstituted diindolylmethane metabolized by the CYP450 enzyme is reduced by about 0.1% to about 10% compared to a control composition that does not comprise the first component. In some embodiments, the metabolism of the substituted or unsubstituted diindolylmethane by the CYP1A2 is reduced by about 0.1% to about 10% compared to a control composition that does not comprise the quercetin. In some embodiments, bioavailability of the substituted or unsubstituted diindolylmethane is increased by about 1-fold to about 100-folds compared to a control composition that does not comprise the quercetin. In some embodiments, the first component, the second component, or both are formulated for administering via an oral or a sublingual route. In some embodiments, the first component, the second component, or both are formulated for administering via the sublingual route. In some embodiments, a ratio between the modulator and the substituted or unsubstituted diindolylmethane (CYP450 modulator: DIM in mg:mg) is about 66:1, about 45:1, about 40:1, about 35:1, about 30:1, about 25:1, about 20:1, about 15:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:5, about 1:10, about 1:20, or about 1:30. In some embodiments, a ratio between the modulator and the substituted or unsubstituted diindolylmethane (CYP450 modulator: DIM in mg:mg) is between about 15:1 and about 10:1. In some embodiments, a ratio between the quercetin and the substituted or unsubstituted diindolylmethane (quercetin: DIM in mg:mg) is between about 15:1 and 10:1. In some embodiments, a ratio between the quercetin and the substituted or unsubstituted diindolylmethane (quercetin: DIM in mg:mg) is about 11:1. In some embodiments, the second component comprises about 700 μg of a vitamin A compound. In some embodiments, the vitamin A compound comprises retinyl palmitate. In some embodiments, the second component comprises about 400 μg of a vitamin A compound. In some embodiments, the second component comprises about 400 retninol equivalents of a vitamin A compound. In some embodiments, the first component comprises one or more of black raspberry, blueberry, ellagic acid, pomegranate, walnuts, blackcurrants, soy, soybean, black soybean, turmeric, apiaceous vegetable, cruciferous vegetables, allium vegetables, garden cress, watercress, yellow onion, kale, alfalfa sprouts, green beans, broccoli,chili powder, daizein, garlic, apple, apricot, chamomile, peppermint, dandelion, green tea, black tea, rooibos tea, itadori tea, coffee, caffeine, caffeic acid, grapes, wine, peanuts, honey, medium-chain triglycerides, coconut and coconut oil, honeycomb, fish oil, rosemary, N-acetyl cysteine, chrysin, quercetin, resveratrol, myricetin, curcumin, curry powder, astaxanthin, algae, yeast, salmon, trout, krill, shrimp, crayfish, quercetin, and chicory root.

Disclosed herein, in some embodiments, are methods of treating acne in a subject in need thereof comprising a combination therapy comprising administering a first composition comprising modulators of one or more CYP450 enzymes and a second composition comprising a substituted or unsubstituted diindolylmethane. In some embodiments, the combination therapy further comprises administering a third composition comprising a substituted or unsubstituted retinoic acid based compound. Disclosed herein, in some embodiments, are methods of treating rosacea in a subject in need thereof comprising a combination therapy comprising administering a first composition comprising modulators of one or more CYP450 enzymes and a second composition comprising a substituted or unsubstituted diindolylmethane.

In some embodiments, the retinoic acid based compound is Vitamin A. In some embodiments, the Vitamin A is contained in the second composition comprising a substituted or unsubstituted diindolylmethane. In some embodiments, the first and the second compositions are administered by oral route. In some embodiments, one or more doses of the first composition comprising modulators of one or more CYP450 enzymes is administered prior to administering the second composition comprising a substituted or unsubstituted diindolylmethane. In some embodiments, the one or more doses of the first composition are administered from about 1 day to about 21 days prior to the administering the second composition. In some embodiments, the one or more doses of the first composition are administered from about 1 hour to about 30 hours prior to the administering the second composition. In some embodiments, a first dose of the first composition is administered about 24 hours prior to administering the second composition and a second dose of the first composition is administered about 12 hours prior to administering the second composition. In some embodiments, the first and the second compositions are administered concurrently.

In some embodiments, the first composition is administered to modulate one or more CYP450 enzymes comprising CYP1A1, CYP1A2, CYP2D6, CYP2C8, CYP2C9, CYP3A4, CYP2C19, and CYP19A1. In some embodiments, the first composition comprises one or more of black raspberry, blueberry, ellagic acid, pomegranate, walnuts, blackcurrants, soy, soybean, black soybean, turmeric, apiaceous vegetable, cruciferous vegetables, allium vegetables, garden cress, watercress, yellow onion, kale, alfalfa sprouts, green beans, chili powder, daizein, garlic, apple, apricot, chamomile, peppermint, dandelion, green tea, black tea, rooibos tea, itadori tea, coffee, caffeine, caffeic acid, grapes, wine, peanuts, honey, medium-chain triglycerides, coconut and coconut oil, honeycomb, fish oil, rosemary, N-acetyl cysteine, chrysin, quercetin, resveratrol, myricetin, curcumin, curry powder, fish oil, rosemary, astaxanthin, algae, yeast, salmon, trout, krill, shrimp, crayfish, and chicory root.

In some embodiments, the first composition is administered to inhibit one or more enzymes comprising CYP1A1, CYP1A2, CYP2D6, CYP2C8, CYP2C9, CYP3A4, CYP2C19, and CYP19A1. In some embodiments, the first composition comprises one or more of black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, grapes, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin. In some embodiments, the first composition comprises one or more of black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin.

In some embodiments, the first composition is administered to induce one or more enzymes cytochrome P450 enzymes comprising CYP1A1, CYP1A2, CYP2D6, CYP2C8, CYP2C9, CYP2C19, and CYP19A1. In some embodiments, the first composition comprises one or more of cruciferous vegetables, resveratrol, grapes, wine, peanuts, soy, itadori tea, green tea, black tea, curcumin, turmeric, curry powder, soybean, garlic, fish oil, rosemary, astaxanthin, algae, yeast, salmon, trout, krill, shrimp, crayfish, chicory root, quercertin, apple, apricot, blueberries, yellow onion, kale, alfalfa sprouts, green beans, broccoli, black tea, chili powder, and rooibos tea.

In some embodiments, the combination therapy increases bioavailability of the substituted or unsubstituted diindolylmethane. In some embodiments, the combination therapy increases the bioavailability of the substituted or unsubstituted diindolylmethane by about 1-fold to about 1000-fold compared to a monotherapy with only the second composition. In some embodiments, the combination therapy increases the bioavailability of the substituted or unsubstituted diindolylmethane by about 1-fold compared to a monotherapy with only the second composition. In some embodiments, the combination therapy increases the bioavailability of the substituted or unsubstituted diindolylmethane by about 2-fold compared to a monotherapy with only the second composition. In some embodiments, the combination therapy increases the bioavailability of the substituted or unsubstituted diindolylmethane by about 3-fold compared to a monotherapy with only the second composition. In some embodiments, the combination therapy increases the bioavailability of the substituted or unsubstituted diindolylmethane by about 4-fold compared to a monotherapy with only the second composition. In some embodiments, the combination therapy increases the bioavailability of the substituted or unsubstituted diindolylmethane by about 5-fold compared to a monotherapy with only the second composition. In some embodiments, the combination therapy increases the bioavailability of the substituted or unsubstituted diindolylmethane by about 10-fold compared to a monotherapy with only the second composition. In some embodiments, the combination therapy increases the bioavailability of the substituted or unsubstituted diindolylmethane by about 20-fold compared to a monotherapy with only the second composition. In some embodiments, the combination therapy increases the bioavailability of the substituted or unsubstituted diindolylmethane by about 30-fold compared to a monotherapy with only the second composition. In some embodiments, the combination therapy increases the bioavailability of the substituted or unsubstituted diindolylmethane by about 40-fold compared to a monotherapy with only the second composition. In some embodiments, the combination therapy increases the bioavailability of the substituted or unsubstituted diindolylmethane by about 50-fold compared to a monotherapy with only the second composition. In some embodiments, the combination therapy increases the bioavailability of the substituted or unsubstituted diindolylmethane by about 60-fold compared to a monotherapy with only the second composition. In some embodiments, the combination therapy increases the bioavailability of the substituted or unsubstituted diindolylmethane by about 70-fold compared to a monotherapy with only the second composition. In some embodiments, the combination therapy increases the bioavailability of the substituted or unsubstituted diindolylmethane by about 80-fold compared to a monotherapy with only the second composition. In some embodiments, the combination therapy increases the bioavailability of the substituted or unsubstituted diindolylmethane by about 90-fold compared to a monotherapy with only the second composition. In some embodiments, the combination therapy increases the bioavailability of the substituted or unsubstituted diindolylmethane by about 100-fold compared to a monotherapy with only the second composition. In some embodiments, the combination therapy increases the bioavailability of the substituted or unsubstituted diindolylmethane by about 200-fold compared to a monotherapy with only the second composition. In some embodiments, the combination therapy increases the bioavailability of the substituted or unsubstituted diindolylmethane by about 300-fold compared to a monotherapy with only the second composition. In some embodiments, the combination therapy increases the bioavailability of the substituted or unsubstituted diindolylmethane by about 400-fold compared to a monotherapy with only the second composition. In some embodiments, the combination therapy increases the bioavailability of the substituted or unsubstituted diindolylmethane by about 500-fold compared to a monotherapy with only the second composition. In some embodiments, the combination therapy increases the bioavailability of the substituted or unsubstituted diindolylmethane by about 600-fold compared to a monotherapy with only the second composition. In some embodiments, the combination therapy increases the bioavailability of the substituted or unsubstituted diindolylmethane by about 700-fold compared to a monotherapy with only the second composition. In some embodiments, the combination therapy increases the bioavailability of the substituted or unsubstituted diindolylmethane by about 800-fold compared to a monotherapy with only the second composition. In some embodiments, the combination therapy increases the bioavailability of the substituted or unsubstituted diindolylmethane by about 900-fold compared to a monotherapy with only the second composition. In some embodiments, the combination therapy increases the bioavailability of the substituted or unsubstituted diindolylmethane by about 1000-fold compared to a monotherapy with only the second composition. In some embodiments, the second composition is administered at a dosage comprising at least 15 mg of the substituted or unsubstituted diindolylmethane.

In some embodiments, the combination therapy increases Cmax of the substituted or unsubstituted diindolylmethane in plasma. In some embodiments, the combination therapy increases the Cmax of the substituted or unsubstituted diindolylmethane in plasma by from about 1-fold to about 1000-fold compared to a monotherapy with only the first composition. In some embodiments, the combination therapy increases the Cmax of the substituted or unsubstituted diindolylmethane by about 1-fold compared to a monotherapy with only the second composition. In some embodiments, the combination therapy increases the Cmax of the substituted or unsubstituted diindolylmethane by about 2-fold compared to a monotherapy with only the second composition. In some embodiments, the combination therapy increases the Cmax of the substituted or unsubstituted diindolylmethane by about 3-fold compared to a monotherapy with only the second composition. In some embodiments, the combination therapy increases the Cmax of the substituted or unsubstituted diindolylmethane by about 4-fold compared to a monotherapy with only the second composition. In some embodiments, the combination therapy increases the Cmax of the substituted or unsubstituted diindolylmethane by about 5-fold compared to a monotherapy with only the second composition. In some embodiments, the combination therapy increases the Cmax of the substituted or unsubstituted diindolylmethane by about 10-fold compared to a monotherapy with only the second composition. In some embodiments, the combination therapy increases the Cmax of the substituted or unsubstituted diindolylmethane by about 20-fold compared to a monotherapy with only the second composition. In some embodiments, the combination therapy increases the Cmax of the substituted or unsubstituted diindolylmethane by about 30-fold compared to a monotherapy with only the second composition. In some embodiments, the combination therapy increases the Cmax of the substituted or unsubstituted diindolylmethane by about 40-fold compared to a monotherapy with only the second composition. In some embodiments, the combination therapy increases the Cmax of the substituted or unsubstituted diindolylmethane by about 50-fold compared to a monotherapy with only the second composition. In some embodiments, the combination therapy increases the Cmax of the substituted or unsubstituted diindolylmethane by about 60-fold compared to a monotherapy with only the second composition. In some embodiments, the combination therapy increases the Cmax of the substituted or unsubstituted diindolylmethane by about 70-fold compared to a monotherapy with only the second composition. In some embodiments, the combination therapy increases the Cmax of the substituted or unsubstituted diindolylmethane by about 80-fold compared to a monotherapy with only the second composition. In some embodiments, the combination therapy increases the Cmax of the substituted or unsubstituted diindolylmethane by about 90-fold compared to a monotherapy with only the second composition. In some embodiments, the combination therapy increases the Cmax of the substituted or unsubstituted diindolylmethane by about 100-fold compared to a monotherapy with only the second composition. In some embodiments, the combination therapy increases the Cmax of the substituted or unsubstituted diindolylmethane by about 200-fold compared to a monotherapy with only the second composition. In some embodiments, the combination therapy increases the Cmax of the substituted or unsubstituted diindolylmethane by about 300-fold compared to a monotherapy with only the second composition. In some embodiments, the combination therapy increases the Cmax of the substituted or unsubstituted diindolylmethane by about 400-fold compared to a monotherapy with only the second composition. In some embodiments, the combination therapy increases the Cmax of the substituted or unsubstituted diindolylmethane by about 500-fold compared to a monotherapy with only the second composition. In some embodiments, the combination therapy increases the Cmax of the substituted or unsubstituted diindolylmethane by about 600-fold compared to a monotherapy with only the second composition. In some embodiments, the combination therapy increases the Cmax of the substituted or unsubstituted diindolylmethane by about 700-fold compared to a monotherapy with only the second composition. In some embodiments, the combination therapy increases the Cmax of the substituted or unsubstituted diindolylmethane by about 800-fold compared to a monotherapy with only the second composition. In some embodiments, the combination therapy increases the Cmax of the substituted or unsubstituted diindolylmethane by about 900-fold compared to a monotherapy with only the second composition. In some embodiments, the combination therapy increases the Cmax of the substituted or unsubstituted diindolylmethane by about 1000-fold compared to a monotherapy with only the second composition. In some embodiments, the second composition is administered at a dosage comprising at least 15 mg of the substituted or unsubstituted diindolylmethane.

In some embodiments, the combination therapy increases AUC of the substituted or unsubstituted diindolylmethane in plasma. In some embodiments, the combination therapy increases the AUC of the substituted or unsubstituted diindolylmethane in plasma by from about 1-fold to about 1000-fold compared to a monotherapy with only the second composition. In some embodiments, the combination therapy increases the AUC of the substituted or unsubstituted diindolylmethane by about 1-fold compared to a monotherapy with only the second composition. In some embodiments, the combination therapy increases the AUC of the substituted or unsubstituted diindolylmethane by about 2-fold compared to a monotherapy with only the second composition. In some embodiments, the combination therapy increases the AUC of the substituted or unsubstituted diindolylmethane by about 3-fold compared to a monotherapy with only the second composition. In some embodiments, the combination therapy increases the AUC of the substituted or unsubstituted diindolylmethane by about 4-fold compared to a monotherapy with only the second composition. In some embodiments, the combination therapy increases the AUC of the substituted or unsubstituted diindolylmethane by about 5-fold compared to a monotherapy with only the second composition. In some embodiments, the combination therapy increases the AUC of the substituted or unsubstituted diindolylmethane by about 10-fold compared to a monotherapy with only the second composition. In some embodiments, the combination therapy increases the AUC of the substituted or unsubstituted diindolylmethane by about 20-fold compared to a monotherapy with only the second composition. In some embodiments, the combination therapy increases the AUC of the substituted or unsubstituted diindolylmethane by about 30-fold compared to a monotherapy with only the second composition. In some embodiments, the combination therapy increases the AUC of the substituted or unsubstituted diindolylmethane by about 40-fold compared to a monotherapy with only the second composition. In some embodiments, the combination therapy increases the AUC of the substituted or unsubstituted diindolylmethane by about 50-fold compared to a monotherapy with only the second composition. In some embodiments, the combination therapy increases the AUC of the substituted or unsubstituted diindolylmethane by about 60-fold compared to a monotherapy with only the second composition. In some embodiments, the combination therapy increases the AUC of the substituted or unsubstituted diindolylmethane by about 70-fold compared to a monotherapy with only the second composition. In some embodiments, the combination therapy increases the AUC of the substituted or unsubstituted diindolylmethane by about 80-fold compared to a monotherapy with only the second composition. In some embodiments, the combination therapy increases the AUC of the substituted or unsubstituted diindolylmethane by about 90-fold compared to a monotherapy with only the second composition. In some embodiments, the combination therapy increases the AUC of the substituted or unsubstituted diindolylmethane by about 100-fold compared to a monotherapy with only the second composition. In some embodiments, the combination therapy increases the AUC of the substituted or unsubstituted diindolylmethane by about 200-fold compared to a monotherapy with only the second composition. In some embodiments, the combination therapy increases the AUC of the substituted or unsubstituted diindolylmethane by about 300-fold compared to a monotherapy with only the second composition. In some embodiments, the combination therapy increases the AUC of the substituted or unsubstituted diindolylmethane by about 400-fold compared to a monotherapy with only the second composition. In some embodiments, the combination therapy increases the AUC of the substituted or unsubstituted diindolylmethane by about 500-fold compared to a monotherapy with only the second composition. In some embodiments, the combination therapy increases the AUC of the substituted or unsubstituted diindolylmethane by about 600-fold compared to a monotherapy with only the second composition. In some embodiments, the combination therapy increases the AUC of the substituted or unsubstituted diindolylmethane by about 700-fold compared to a monotherapy with only the second composition. In some embodiments, the combination therapy increases the AUC of the substituted or unsubstituted diindolylmethane by about 800-fold compared to a monotherapy with only the second composition. In some embodiments, the combination therapy increases the AUC of the substituted or unsubstituted diindolylmethane by about 900-fold compared to a monotherapy with only the second composition. In some embodiments, the combination therapy increases the AUC of the substituted or unsubstituted diindolylmethane by about 1000-fold compared to a monotherapy with only the second composition.

In some embodiments, the combination therapy decreases Tmax of the substituted or unsubstituted diindolylmethane in plasma. In some embodiments, the combination therapy decreases the Tmax of the substituted or unsubstituted diindolylmethane in plasma by from about 1-fold to about 1000-fold compared to a monotherapy with only the second composition. In some embodiments, the combination therapy decreases the Tmax of the substituted or unsubstituted diindolylmethane by about 1-fold compared to a monotherapy with only the second composition. In some embodiments, the combination therapy decreases the Tmax of the substituted or unsubstituted diindolylmethane by about 2-fold compared to a monotherapy with only the second composition. In some embodiments, the combination therapy decreases the Tmax of the substituted or unsubstituted diindolylmethane by about 3-fold compared to a monotherapy with only the second composition. In some embodiments, the combination therapy decreases the Tmax of the substituted or unsubstituted diindolylmethane by about 4-fold compared to a monotherapy with only the second composition. In some embodiments, the combination therapy decreases the Tmax of the substituted or unsubstituted diindolylmethane by about 5-fold compared to a monotherapy with only the second composition. In some embodiments, the combination therapy decreases the Tmax of the substituted or unsubstituted diindolylmethane by about 10-fold compared to a monotherapy with only the second composition. In some embodiments, the combination therapy decreases the Tmax of the substituted or unsubstituted diindolylmethane by about 20-fold compared to a monotherapy with only the second composition. In some embodiments, the combination therapy decreases the Tmax of the substituted or unsubstituted diindolylmethane by about 30-fold compared to a monotherapy with only the second composition. In some embodiments, the combination therapy decreases the Tmax of the substituted or unsubstituted diindolylmethane by about 40-fold compared to a monotherapy with only the second composition. In some embodiments, the combination therapy decreases the Tmax of the substituted or unsubstituted diindolylmethane by about 50-fold compared to a monotherapy with only the second composition. In some embodiments, the combination therapy decreases the Tmax of the substituted or unsubstituted diindolylmethane by about 60-fold compared to a monotherapy with only the second composition. In some embodiments, the combination therapy decreases the Tmax of the substituted or unsubstituted diindolylmethane by about 70-fold compared to a monotherapy with only the second composition. In some embodiments, the combination therapy decreases the Tmax of the substituted or unsubstituted diindolylmethane by about 80-fold compared to a monotherapy with only the second composition. In some embodiments, the combination therapy decreases the Tmax of the substituted or unsubstituted diindolylmethane by about 90-fold compared to a monotherapy with only the second composition. In some embodiments, the combination therapy decreases the Tmax of the substituted or unsubstituted diindolylmethane by about 100-fold compared to a monotherapy with only the second composition. In some embodiments, the combination therapy decreases the Tmax of the substituted or unsubstituted diindolylmethane by about 200-fold compared to a monotherapy with only the second composition. In some embodiments, the combination therapy decreases the Tmax of the substituted or unsubstituted diindolylmethane by about 300-fold compared to a monotherapy with only the second composition. In some embodiments, the combination therapy decreases the Tmax of the substituted or unsubstituted diindolylmethane by about 400-fold compared to a monotherapy with only the second composition. In some embodiments, the combination therapy decreases the Tmax of the substituted or unsubstituted diindolylmethane by about 500-fold compared to a monotherapy with only the second composition. In some embodiments, the combination therapy decreases the Tmax of the substituted or unsubstituted diindolylmethane by about 600-fold compared to a monotherapy with only the second composition. In some embodiments, the combination therapy decreases the Tmax of the substituted or unsubstituted diindolylmethane by about 700-fold compared to a monotherapy with only the second composition. In some embodiments, the combination therapy decreases the Tmax of the substituted or unsubstituted diindolylmethane by about 800-fold compared to a monotherapy with only the second composition. In some embodiments, the combination therapy decreases the Tmax of the substituted or unsubstituted diindolylmethane by about 900-fold compared to a monotherapy with only the second composition. In some embodiments, the combination therapy decreases the Tmax of the substituted or unsubstituted diindolylmethane by about 1000-fold compared to a monotherapy with only the second composition. In some embodiments, the second composition is administered at a dosage comprising at least 15 mg of the substituted or unsubstituted diindolylmethane.

In some embodiments, the percentage of substituted or unsubstituted diindolylmethane effluxed by P-gp following the combination therapy is about 0.1% to about 50% of the percentage of substituted or unsubstituted diindolylmethane effluxed by P-gp following a monotherapy with only the first composition. In some embodiments, the percentage of substituted or unsubstituted diindolylmethane effluxed by P-gp following the combination therapy is about 0.1% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.2% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.3% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.4% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.5% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.6% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.7% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.8% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 0.9% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 1% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 2% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 3% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 4% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 5% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 6% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 7% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 8% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 9% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 10% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 20% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 30% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 40% of the percentage of substituted or unsubstituted diindolylmethane effluxed by P-gp following a monotherapy with only the second composition. In some embodiments, the percentage of substituted or unsubstituted diindolylmethane effluxed by P-gp following the combination therapy is about 50% of the percentage of substituted or unsubstituted diindolylmethane effluxed by P-gp following a monotherapy with only the second composition. In some embodiments, the second composition is administered at a dosage comprising at least 15 mg of the substituted or unsubstituted diindolylmethane.

In some embodiments, the percentage of substituted or unsubstituted diindolylmethane metabolized by CYP450 enzymes following the combination therapy is from about 0.1% to about 50% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.1% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.2% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.3% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.4% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.5% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.6% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.7% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.8% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 0.9% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 1% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 2% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 3% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 4% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 5% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 6% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 7% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 8% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 9% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 10% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 20% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 30% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 40% of the percentage of substituted or unsubstituted diindolylmethane metabolized by CYP450 enzymes following a monotherapy with only the second composition. In some embodiments, the percentage of substituted or unsubstituted diindolylmethane metabolized by CYP450 enzymes following the combination therapy is about 50% of the percentage of substituted or unsubstituted diindolylmethane metabolized by CYP450 enzymes following a monotherapy with only the second composition. In some embodiments, the second composition is administered at a dosage comprising at least 15 mg of the substituted or unsubstituted diindolylmethane.

In some embodiments, the percentage of a composition influxed by an OATP following the combination therapy is from about 0.1% to about 50% of the percentage of substituted or unsubstituted diindolylmethane influxed by an OATP following a monotherapy with only the second composition. In some embodiments, the percentage of a composition influxed by an OATP following the combination therapy is about 0.2% of the percentage of substituted or unsubstituted diindolylmethane influxed by an OATP following a monotherapy with only the second composition. In some embodiments, the percentage of a composition influxed by an OATP following the combination therapy is about 0.3% of the percentage of substituted or unsubstituted diindolylmethane influxed by an OATP following a monotherapy with only the second composition. In some embodiments, the percentage of a composition influxed by an OATP following the combination therapy is about 0.4% of the percentage of substituted or unsubstituted diindolylmethane influxed by an OATP following a monotherapy with only the second composition.

In some embodiments, the percentage of a composition influxed by an OATP following the combination therapy is about 0.5% of the percentage of substituted or unsubstituted diindolylmethane influxed by an OATP following a monotherapy with only the second composition. In some embodiments, the percentage of a composition influxed by an OATP following the combination therapy is about 0.6% of the percentage of substituted or unsubstituted diindolylmethane influxed by an OATP following a monotherapy with only the second composition. In some embodiments, the percentage of a composition influxed by an OATP following the combination therapy is about 0.7% of the percentage of substituted or unsubstituted diindolylmethane influxed by an OATP following a monotherapy with only the second composition. In some embodiments, the percentage of a composition influxed by an OATP following the combination therapy is about 0.8% of the percentage of substituted or unsubstituted diindolylmethane influxed by an OATP following a monotherapy with only the second composition. In some embodiments, the percentage of a composition influxed by an OATP following the combination therapy is about 0.9% of the percentage of substituted or unsubstituted diindolylmethane influxed by an OATP following a monotherapy with only the second composition. In some embodiments, the percentage of a composition influxed by an OATP following the combination therapy is about 1% of the percentage of substituted or unsubstituted diindolylmethane influxed by an OATP following a monotherapy with only the second composition. In some embodiments, the percentage of a composition influxed by an OATP following the combination therapy is about 2% of the percentage of substituted or unsubstituted diindolylmethane influxed by an OATP following a monotherapy with only the second composition. In some embodiments, the percentage of a composition influxed by an OATP following the combination therapy is about 3% of the percentage of substituted or unsubstituted diindolylmethane influxed by an OATP following a monotherapy with only the second composition. In some embodiments, the percentage of a composition influxed by an OATP following the combination therapy is about 4% of the percentage of substituted or unsubstituted diindolylmethane influxed by an OATP following a monotherapy with only the second composition. In some embodiments, the percentage of a composition influxed by an OATP following the combination therapy is about 5% of the percentage of substituted or unsubstituted diindolylmethane influxed by an OATP following a monotherapy with only the second composition. In some embodiments, the percentage of a composition influxed by an OATP following the combination therapy is about 6% of the percentage of substituted or unsubstituted diindolylmethane influxed by an OATP following a monotherapy with only the second composition. In some embodiments, the percentage of a composition influxed by an OATP following the combination therapy is about 7% of the percentage of substituted or unsubstituted diindolylmethane influxed by an OATP following a monotherapy with only the second composition. In some embodiments, the percentage of a composition influxed by an OATP following the combination therapy is about 8% of the percentage of substituted or unsubstituted diindolylmethane influxed by an OATP following a monotherapy with only the second composition. In some embodiments, the percentage of a composition influxed by an OATP following the combination therapy is about 9% of the percentage of substituted or unsubstituted diindolylmethane influxed by an OATP following a monotherapy with only the second composition. In some embodiments, the percentage of a composition influxed by an OATP following the combination therapy is about 10% of the percentage of substituted or unsubstituted diindolylmethane influxed by an OATP following a monotherapy with only the second composition. In some embodiments, the percentage of a composition influxed by an OATP following the combination therapy is about 20% of the percentage of substituted or unsubstituted diindolylmethane influxed by an OATP following a monotherapy with only the second composition. In some embodiments, the percentage of a composition influxed by an OATP following the combination therapy is about 30% of the percentage of substituted or unsubstituted diindolylmethane influxed by an OATP following a monotherapy with only the second composition. In some embodiments, the percentage of a composition influxed by an OATP following the combination therapy is about 40% of the percentage of substituted or unsubstituted diindolylmethane influxed by an OATP following a monotherapy with only the second composition. In some embodiments, the percentage of a composition influxed by an OATP following the combination therapy is about 50% of the percentage of substituted or unsubstituted diindolylmethane influxed by an OATP following a monotherapy with only the second composition. In some embodiments, the second composition comprising a substituted or unsubstituted diindolylmethane is administered in a dosage comprising at least 15 mg of the substituted or unsubstituted diindolylmethane. In some embodiments, the OATP is an OATP expressed in the hepatocytes of the liver.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed. It is intended that the following claims define the scope of the present disclosure and that methods and structures within the scope of these claims and their equivalents be covered thereby.

Unless defined otherwise, all technical and scientific terms used herein have the same meaning as commonly understood by one of skill in the art to which the present disclosure described herein belong. All publications, patents, and patent applications mentioned in this specification are hereby incorporated by reference to the same extent as if each individual publication, patent, or patent application was specifically and individually indicated to be incorporated by reference.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

DIM

Diindolylmethane (DIM) is a natural compound formed during the autolytic breakdown of glucobrassicin present in food plants of the Brassica genus, including broccoli, cabbage, Brussels sprouts, cauliflower and kale. The autolytic breakdown of glucobrassicin requires the catalytic reaction of the enzyme myrosinase, which is endogenous to these plants and released upon rupture of the cell wall. The compound is normally manufactured by chemical synthesis but in some embodiments is also prepared by natural means from the extracts of Brassica vegetables, as listed above, particularly from sprouting broccoli or from broccoli seeds.

Thus, the substituted or unsubstituted DIM in some embodiments is synthetic, or in some embodiments is a natural product obtained from the Brassica genus of plants, as discussed above.

Vitamin A

Vitamin A is a fat-soluble vitamin that has several important functions in the body. Prescription creams and pills containing retinoids, a synthetic form of vitamin A, are used to help clear up severe acne and psoriasis. They have also shown promise for treating other skin disorders such as warts and premature aging from the sun. Recent studies show that topical forms along with antioxidants may help minimize the appearance of fine lines and wrinkles. Oral isotretinoin, a synthetic Vitamin A has been approved since 1982 for the treatment of severe, treatment-resistant acne. Isotretinoin decreases the size and secretion of the sebaceous gland, normalizes follicular keratinization, prevents comedogenesis, inhibits the growth of surface and ductal Propionibacterium acnes via changes of the follicular milieu, and has anti-inflammatory effects.

Acne

Acne is a chronic inflammatory disease of the pilosebaceous unit resulting from androgen-induced increased sebum production, altered keratinisation, inflammation, and bacterial colonisation of hair follicles on the face, neck, chest, and back by Propionibacterium acnes. The initial pathology of acne is the comedo and includes acne vulgaris, neonatal acne, infantile acne, and pomade acne. The disease of acne is characterized by a great variety of clinical lesions. Although one type of lesion may be predominant (typically the comedo), close observation usually reveals the presence of several types of lesions (comedones, pustules, papules, and/or nodules). The lesions can be either noninflammatory or, more typically, inflammatory. In addition to lesions, patients may have, as the result of lesions, scars of varying size. The fully developed, open comedo (i.e., a plug of dried sebum in a skin pore) is not usually the site of inflammatory changes, unless it is traumatized by the patient. The developing microcomedo and the closed comedo are the major sites for the development of inflammatory lesions. Because the skin is always trying to repair itself, sheaths of cells will grow out from the epidermis (forming appendageal structures) in an attempt to encapsulate the inflammatory reaction. This encapsulation is often incomplete and further rupture of the lesion typically occurs, leading to multichanneled tracts as can be seen in many acne scars.

There are primarily four factors that are believed to be the contributors of acne: (1) increased sebum production; (2) comedo formation, in which the follicular infundibulum hypercornifies, hyperkeratinizes, and hypodesquamates; (3) colonization of the follicle by anaerobic Propionibacterium sp., mainly P. acnes; and (4) the host's inflammatory response. These four factors are interrelated to each other. Sebum is comedogenic and causes inflammation by itself. The Propionibacterium has high lipolytic activity and liberates free fatty acids from sebum lipids. The free fatty acids have been shown to cause marked inflammation. The microorganisms also produce other extracellular enzymes such as proteases, hyaluronidases, and chemotactic factors, which are important in some inflammatory processes. Other factors such as diet have been implicated, but not proven. Facial scarring due to acne affects up to 20% of teenagers. Acne can persist into adulthood, with detrimental effects on self-esteem. The disease is so common in youth at their puberty that it often has been termed physiological. Although acne stops appearing for most people by the age of 25, some people, the majority of them women, experience the disease well into their adult life. This "adult acne" differs from teenage acne in location and that it tends to be more inflammatory with fewer comedones.

In general, there are four major principles presently governing the therapy of acne: (i) correction of the altered pattern of follicular keratinization; (ii) decrease sebaceous gland activity; (iii) decrease the follicular bacterial population (especially P. acnes) and thereby inhibit the production of extra cellular inflammatory products; and (iv) produce an anti-inflammatory effect.

Rosacea

Rosacea is a chronic inflammatory condition of the facial skin affecting the blood vessels and pilosebaceous units. Rosacea is more common in persons of northern and western European descent with a fair complexion, but it can affect skin of any color. Although symptoms may wax and wane during the short term, rosacea can progress with time. Patients usually present with complaints of flushing and blushing and sensitive skin, and their skin may be especially irritated by topical preparations. Rosacea has a variety of triggers; however, they may be unnoticed by the patient.

It is a chronic and progressive cutaneous vascular disorder, primarily involving the malar and nasal areas of the face. Rosacea is characterized by flushing, erythema, papules, pustules, telangiectasia, facial edema, ocular lesions, and, in its most advanced and severe form, hyperplasia of tissue and sebaceous glands leading to rhinophyma. Rhinophyma, a florid overgrowth of the tip of the nose with hypervascularity and modularity, is an unusual progression of rosacea of unknown cause. Ocular lesions are common, including mild conjunctivitis, burning, and grittiness. Blepharitis, the most common ocular manifestation, is a nonulcerative condition of the lidmargins. Rosacea most commonly occurs between the ages of 30 to 60, and may be seen in women experiencing hormonal changes associated with menopause. Women are more frequently affected than men; the most severe cases, however, are seen in men.

Methods of Treating Acne or Rosacea by Combination Therapy

The cytochromes P450 are a superfamily of hemoproteins. They represent the terminal oxidases of the mixed function oxidase system. The cytochrome P450 gene superfamily is composed of at least 207 genes that have been named based on the evolutionary relationships of the cytochromes P450. Three cytochrome P450 gene families (CYP1, CYP2 and CYP3) have been shown to be responsible for metabolism of several drugs. At least 15 cytochromes P450 have been characterized to varying degrees in the human liver. The liver contains many isoforms of cytochrome P450 and can biotransform a large variety of substances. The enterocytes lining the lumen of the intestine also have significant cytochrome P450 activity, and in some cases this activity is dominated by a single family of isozymes, 3A, which are important isoforms in drug metabolism.

Provided herein, in some embodiments, are methods of treating acne or rosacea in a subject in need thereof comprising administering to the subject a combination therapy comprising a first composition comprising modulators of one or more cytochrome P-450 enzymes and a second composition comprising a substituted or unsubstituted diindolylmethane. In some embodiments, the combination therapy further comprises administering a third composition comprising a substituted or unsubstituted retinoic acid based compound. In some embodiments, the substituted or unsubstituted retinoic acid based compound is Vitamin A. In some embodiments, the Vitamin A is contained within the second composition. In some embodiments, the combination therapy is carried out by administering a pharmaceutical composition as described herein, comprising a first component comprising a modulator of a CYP450 enzyme and a second component comprising a substituted or unsubstituted diindolylmethane. In some cases, the pharmaceutical composition further comprises a third component, wherein the third component comprises a retinoic acid based compound as described herein.

In some embodiments, the first composition comprises at least one modulator of one or more CYP-450 enzymes selected from a group consisting of CYP1A1, CYP1A2, CYP2A, CYP2B, CYP2B1, CYP2C, CYP2C6, CYP2C9, CYP2C19, CYP2D6, CYP2E1, CYP3A, CYP3A2, CYP3A4, CYP4A1, CYP4B1, and CYP19A1.

In some embodiments, the first composition comprises at least one inhibitor of one or more CYP-450 enzymes selected from a group consisting of CYP1A1, CYP1A2, CYP2A, CYP2B, CYP2B1, CYP2C, CYP2C6, CYP2C9, CYP2C19, CYP2D6, CYP2E1, CYP3A, CYP3A2, CYP3A4, CYP4A1, and CYP4B1. In some embodiments, the first composition comprises at least one inhibitor of one or more CYP-450 enzymes selected from a group consisting of CYP2A, CYP2B, CYP2B1, CYP2C, CYP2C6, CYP2C9, CYP2C19, CYP2D6, CYP2E1, CYP3A, and CYP3A2. In some embodiments, the at least one inhibitor of one or more CYP-450 enzymes is selected from black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, grapes, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin. In some embodiments, the at least one inhibitor is selected from black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin. In some embodiments, the at least one inhibitor is not grapefruit juice, green tea extract, or saw palmetto extract.

In some embodiments, the first composition comprises at least one inducer of one or more CYP-450 enzymes selected from a group consisting of CYP1A1, CYP1A2, CYP2A, CYP2B, CYP2B1, CYP2C, CYP2C6, CYP2C9, CYP2C19, CYP2D6, CYP2E1, CYP3A, CYP3A2, CYP3A4, CYP4A1, CYP4B1, and CYP19A1. In some embodiments, the first composition comprises at least one inducer of one or more CYP-450 enzymes selected from a group consisting of CYP1A1, CYP1A2, CYP2C19, and CYP3A4. In some embodiments, the at least one inducer of one or more CYP-450 enzymes is selected from cruciferous vegetables, resveratrol (e.g., grapes, wine, peanuts, soy, itadori tea, green tea, black tea, curcumin (e.g., turmeric, curry powder), soybean, garlic, fish oil, rosemary, astaxanthin (e.g., algae, yeast, salmon, trout, krill, shrimp, crayfish), chicory root, quercertin (e.g., apple, apricot, blueberries, yellow onion, kale, alfalfa sprouts, green beans, broccoli, black tea, chili powder), and rooibos tea. In some embodiments, the at least one inducer of one or more CYP-450 enzymes is selected from cruciferous vegetables, resveratrol (e.g., grapes, wine, peanuts, soy, itadori tea, green tea, black tea, curcumin (e.g., turmeric, curry powder), soybean, garlic, fish oil, rosemary, astaxanthin (e.g., algae, yeast, salmon, trout, krill, shrimp, crayfish). In some embodiments, the at least one inducer of one or more CYP-450 enzymes is selected from chicory root, quercertin (e.g., apple, apricot, blueberries, yellow onion, kale, alfalfa sprouts, green beans, broccoli, black tea, chili powder), rosemary, and garlic. In some embodiments, the at least one inducer of one or more CYP-450 enzymes is rooibos tea, garlic, fish oil, cruciferous vegetables, and curcumin (e.g., turmeric, curry powder). In some embodiments, the at least one inducer of one or more CYP-450 enzymes is green tea, or caffeic acid (e.g., coffee).

In some embodiments, the first compositions described herein comprising one or more modulators of CYP-450 enzymes are administered in the form of pills, tablets, liquid formulations, shakes, beverages etc. In some embodiments, the first compositions described herein comprising one or more modulators of CYP-450 enzymes are provided in the form of powders and packaged in packets or pouches.

In some embodiments, the combination therapy comprises administering the first composition comprising at least one inhibitor of one or more CYP-450 enzymes prior to administering the second composition comprising substituted or unsubstituted diindolylmethane. In some embodiments, the combination therapy comprises administering one or more doses of the first composition comprising at least one inhibitor of one or more CYP-450 enzymes prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 21 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 20 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 19 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 18 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 17 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 16 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 15 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 14 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 13 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 12 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 11 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 10 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 9 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 8 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 7 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 6 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 5 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 4 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 3 days prior to administering the second composition comprising substituted or unsubstituted diindolylmethane. In some embodiments, the combination therapy comprises administering one or more doses of the first composition comprising at least one inhibitor of one or more CYP-450 enzymes from about 1 day to about 2 days prior to administering the second composition comprising substituted or unsubstituted diindolylmethane.

In some embodiments, the combination therapy comprises administering one or more doses of the first composition comprising at least one inhibitor of one or more CYP-450 enzymes from about 1 hour to about 48 hours prior to administering the second composition comprising substituted or unsubstituted diindolylmethane. In some embodiments, the combination therapy comprises administering one or more doses of the first composition comprising at least one inhibitor of one or more CYP-450 enzymes about 1 hour prior to administering the second composition comprising substituted or unsubstituted diindolylmethane. In some embodiments, the combination therapy comprises administering one or more doses of the first composition comprising at least one inhibitor of one or more CYP-450 enzymes about 6 hour prior to administering the second composition comprising substituted or unsubstituted diindolylmethane. In some embodiments, the combination therapy comprises administering one or more doses of the first composition comprising at least one inhibitor of one or more CYP-450 enzymes about 12 hours prior to administering the second composition comprising substituted or unsubstituted diindolylmethane. In some embodiments, the combination therapy comprises administering one or more doses of the first composition comprising at least one inhibitor of one or more CYP-450 enzymes about 18 hours prior to administering the second composition comprising substituted or unsubstituted diindolylmethane. In some embodiments, the combination therapy comprises administering one or more doses of the first composition comprising at least one inhibitor of one or more CYP-450 enzymes about 24 hours prior to administering the second composition comprising substituted or unsubstituted diindolylmethane. In some embodiments, the combination therapy comprises administering one or more doses of the first composition comprising at least one inhibitor of one or more CYP-450 enzymes about 30 hours prior to administering the second composition comprising substituted or unsubstituted diindolylmethane. In some embodiments, the combination therapy comprises administering one or more doses of the first composition comprising at least one inhibitor of one or more CYP-450 enzymes about 36 hours prior to administering the second composition comprising substituted or unsubstituted diindolylmethane. In some embodiments, the combination therapy comprises administering one or more doses of the first composition comprising at least one inhibitor of one or more CYP-450 enzymes about 42 hours prior to administering the second composition comprising substituted or unsubstituted diindolylmethane. In some embodiments, the combination therapy comprises administering one or more doses of the first composition comprising at least one inhibitor of one or more CYP-450 enzymes about 48 hours prior to administering the second composition comprising substituted or unsubstituted diindolylmethane.

In some embodiments, the one or more doses of the first composition comprising at least one inhibitor of one or more CYP-450 enzymes are administered over a period of from about 12 hours to about 48 hours. In some embodiments, the one or more doses of the first composition comprising at least one inhibitor of one or more CYP-450 enzymes are administered over a period of about 12 hours. In some embodiments, the one or more doses of the first composition comprising at least one inhibitor of one or more CYP-450 enzymes are administered over a period of about 18 hours. In some embodiments, the one or more doses of the first composition comprising at least one inhibitor of one or more CYP-450 enzymes are administered over a period of about 24 hours. In some embodiments, the one or more doses of the first composition comprising at least one inhibitor of one or more CYP-450 enzymes are administered over a period of about 30 hours. In some embodiments, the one or more doses of the first composition comprising at least one inhibitor of one or more CYP-450 enzymes are administered over a period of about 36 hours. In some embodiments, the one or more doses of the first composition comprising at least one inhibitor of one or more CYP-450 enzymes are administered over a period of about 42 hours. In some embodiments, the one or more doses of the first composition comprising at least one inhibitor of one or more CYP-450 enzymes are administered over a period of about 48 hours.

In some embodiments, the one or more doses of the first composition comprising at least one inhibitor of one or more CYP-450 enzymes comprises a first dose and a second dose. In some embodiments, the first and second doses of the first composition are respectively administered about 48 hours and about 24 hours prior to the administration of a second composition comprising substituted or unsubstituted diindolylmethane. In some embodiments, the first and second doses of the first composition are respectively administered about 42 hours and about 18 hours prior to the administration of a second composition comprising substituted or unsubstituted diindolylmethane. In some embodiments, the first and second doses of the first composition are respectively administered about 36 hours and about 12 hours prior to the administration of a second composition comprising substituted or unsubstituted diindolylmethane. In some embodiments, the first and second doses of the first composition are respectively administered about 30 hours and about 6 hours prior to the administration of a second composition comprising substituted or unsubstituted diindolylmethane. In some embodiments, the first and second doses of the first composition are respectively administered about 24 hours and about 1 hour prior to the administration of a second composition comprising substituted or unsubstituted diindolylmethane.

Increase in Bioavailability of DIM by Prior Administration of CYP-450 Modulators In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane compared to a monotherapy with a composition comprising substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane compared to a monotherapy with a composition comprising substituted or unsubstituted diindolylmethane and Vitamin A.

The active metabolite of vitamin A, retinoic acid, is known to be a powerful regulator of gene transcription. Retinoic acid is also a therapeutic drug. The oxidative metabolism of retinoic by certain members of the cytochrome P450 (CYP-450) superfamily helps to maintain tissue RA concentrations within appropriate bounds. Enzyme kinetic studies have demonstrated that several CYP proteins, expecially those belonging to the CYP26 family (CYP26A1, CYP26B1, and CYP26C1) are capable of metabolizing retinoic acid. Without being limited by any particular theory, it is contemplated that controlling the activity of CYP enzymes that affect the metabolism of retinoic acid leads to an increase in its bioavailability. Furthermore, it is also contemplated, without being bound by a particular theory, that retinoic acid itself inhibits the activity of certain CYP-450 enzymes, such as CYP1A1 and CYP1A2, which in turn leads to reduced metabolism of diindolylmethane by CYP450 enzymes and results in increased bioavailability of diindolylmethane. In some embodiments, the combination therapy comprising administration of one or more modulators of CYP-450 enzymes prior to the administration of a composition comprising a substituted or substituted diindolylmethane and Vitamin A increases the bioavailability of the substituted or unsubstituted diindolylmethane compared to a monotherapy with a composition comprising substituted or unsubstituted diindolylmethane and Vitamin A. In some embodiments, the increase in bioavailability of substituted or unsubstituted diindolylmethane is due to reduced metabolism of Vitamin A by CYP-450 enzymes. In some embodiments, the increase in bioavailability of substituted or unsubstituted diindolylmethane is due to inhibition of CYP-450 enzymes by Vitamin A.

In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by from about 1-fold to about 1000-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 1-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 2-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 3-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 4-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 5-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 6-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 7-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 8-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 9-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 10-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 20-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 30-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 40-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 50-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 60-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 70-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 80-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 90-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 100-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 200- fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 300-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 400-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 500-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 600-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 700-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 800-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 900-fold compared to a monotherapy with a composition comprising a substituted or unsubstituted diindolylmethane. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by about 1000-fold compared to a monotherapy with a composition comprising a substituted or unsubstituted diindolylmethane.

In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by reducing its metabolism by one or more CYP-450 enzymes. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by reducing its metabolism by one or more of CYP2D6, CYP2C8, CYP2C9, CYP3A4,CYP2C19, and CYP19A1. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by reducing its metabolism by CYP3A4. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by reducing its metabolism by CYP2C19.

In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is from about 0.1% to about 50% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.1% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.2% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.3% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.4% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.5% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.6% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.7% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.8% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 0.9% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 1% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 2% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 3% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 4% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 5% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 6% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 7% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 8% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 9% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 10% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 20% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 30% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 40% of the percentage of substituted or unsubstituted diindolylmethane metabolized by CYP-450 enzymes following a monotherapy with a composition comprising a substituted or unsubstituted diindolylmethane. In some embodiments, the percentage of substituted or unsubstituted diindolylmethane metabolized by CYP-450 enzymes following the combination therapy comprising administration of one or more modulators of CYP-450 enzymes prior to the administration of a composition comprising a substituted or substituted diindolylmethane is about 50% of the percentage of substituted or unsubstituted diindolylmethane metabolized by CYP-450 enzymes following a monotherapy with a composition comprising a substituted or unsubstituted diindolylmethane.

In some embodiments, the combination therapy by administering the first and second compositions, comprising a substituted or unsubstituted diindolylmethane and one or more inducers of CYP1A1 and/or CYPA2, respectively, synergistically induces the CYP1A1 and/or CYP1A2 enzymes. In some embodiments, the synergistic induction of the CYPA1 and/or CYP1A2 enzymes leads to increased efficacy of the substituted or unsubstituted diindolylmethane against acne or rosacea.

Improved Pharmacokinetic Parameters of DIM upon Prior Administration of CYP-450 Modulators Bioavailability includes the following exemplary pharmacokinetic factors: rate (or time after administration) of achievement of minimum effective drug serum concentration (MEC), maximum drug serum concentration (Cmax), rate (or time after administration) of achievement of maximum drug serum concentration (Tmax), and the area under the drug serum concentration-time curve above a line representing minimum effective drug serum concentration (AUC). In some embodiments, the methods of treating acne or rosacea by administration of substituted or unsubstituted diindolylmethane by sublingual or buccal route, as described herein, leads to enhancement in one more of the factors mentioned above.

Increased Cmax

In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by from about 1-fold to about 1000-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by from about 1-fold to about 500-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by from about 1-fold to about 100-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by from about 1-fold to about 50-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by from about 1-fold to about 20-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by from about 1-fold to about 10-fold compared to a monotherapy with a composition comprising a substituted or unsubstituted diindolylmethane.

In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 1-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 2-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 3-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 4-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 5-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 6-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 7-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 8-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 9-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 10-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 20-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 30-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 40-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 50-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 60-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 70-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 80-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 90-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 100-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 200-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 300-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 400-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 500-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 600-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 700-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 800-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 900-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Cmax of the substituted or unsubstituted diindolylmethane in plasma increases by about 1000-fold compared to a monotherapy with a composition comprising a substituted or unsubstituted diindolylmethane.

Increased AUC

In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by from about 1-fold to about 1000-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by from about 1-fold to about 500-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by from about 1-fold to about 100-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by from about 1-fold to about 50-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by from about 1-fold to about 20-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by from about 1-fold to about 10-fold compared to a monotherapy with a composition comprising a substituted or unsubstituted diindolylmethane.

In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 1-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 2-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 3-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 4-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 5-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 6-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 7-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 8-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 9-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 10-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 20-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 30-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 40-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 50-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 60-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 70-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 80-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 90-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 100-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 200-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 300-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 400-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 500-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 600-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 700-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 800-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 900-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the AUC of the substituted or unsubstituted diindolylmethane in plasma increases by about 1000-fold compared to a monotherapy with a composition comprising a substituted or unsubstituted diindolylmethane.

Decreased Tmax

In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by from about 1-fold to about 1000-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by from about 1-fold to about 500-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by from about 1-fold to about 100-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by from about 1-fold to about 50-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by from about 1-fold to about 20-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by from about 1-fold to about 10-fold compared to a monotherapy with a composition comprising a substituted or unsubstituted diindolylmethane.

In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 1-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 2-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 3-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 4-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 5-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 6-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 7-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 8-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 9-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 10-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 20-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 30-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 40-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 50-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 60-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 70-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 80-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 90-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 100-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 200-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 300-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 400-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 500-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 600-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 700-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 800-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 900-fold compared to a monotherapy with a composition comprising a substituted or unsubstituted diindolylmethane. In some embodiments, following the combination therapy comprising administration of one or more modulators of CYP-450 enzymes prior to the administration of a composition comprising a substituted or unsubstituted diindolylmethane the Tmax of the substituted or unsubstituted diindolylmethane in plasma decreases by about 1000-fold compared to a monotherapy with a composition comprising a substituted or unsubstituted diindolylmethane.

Methods of Treating Acne and/or Rosacea using DIM by Avoiding Efflux and/or Influx by Membrane Transporters Membrane transporters are known to be major determinants of the pharmacokinetic, safety and efficacy profiles of drugs. In particular, more than 400 membrane transporters in two major superfamilies: ATP-binding cassette (ABC) and solute carrier (SLC) have been annotated in the human genome. It is known that transporters play a part in vivo in drug disposition, therapeutic efficacy and adverse drug reactions. The in vivo role of transporters is demonstrated in several animal species, including knockout mice and by loss-of-function genetic variants in humans. These studies have provided considerable information on the in vivo role of many ABC and SLC transporters. Clinical pharmacokinetic drug-drug interaction (DDI) studies have suggested that transporters often work together with drug-metabolizing enzymes (DMEs) in drug absorption and elimination.

P-gp

P-glycoprotein (P-gp), a 170-kDa member of the ATP-binding cassette transporter superfamily (ABCB1), is a membrane transporter protein that is known to mediate the ATP-dependent export of drugs from cells. Intestinal drug efflux by P-gp is widely recognized as a major determinant for the low or variable oral absorption of several drugs. It has been shown to be expressed in the luminal membrane of the small intestine and blood-brain barrier, and in the apical membranes of excretory cells such as hepatocytes and kidney proximal tubule epithelia. In recent years, there has been much interest in the potential role of P-gp, which, by its action of pumping drugs out of epithelial cells back into the intestinal lumen, is hypothesized to limit the oral bioavailability of a wide range of drugs. Several drugs have been shown to have low bioavailability due to the P-gp-mediated efflux occurring in the small intestine.

In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by reducing its efflux by P-gp. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is from about 0.1% to about 50% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.1% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.2% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.3% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.4% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.5% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.6% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.7% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.8% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 0.9% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 1% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 2% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 3% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 4% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 5% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 6% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 7% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 8% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 9% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 10% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 20% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 30% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 40% of the percentage of substituted or unsubstituted diindolylmethane effluxed by P-gp following a monotherapy with a composition comprising a substituted or unsubstituted diindolylmethane. In some embodiments, the percentage of substituted or unsubstituted diindolylmethane effluxed by P-gp following the combination therapy comprising administration of one or more modulators of CYP-450 enzymes prior to the administration of a composition comprising a substituted or substituted diindolylmethane is about 50% of the percentage of substituted or unsubstituted diindolylmethane effluxed by P-gp following a monotherapy with a composition comprising a substituted or unsubstituted diindolylmethane.

In some embodiments, the percentage of the composition comprising substituted or unsubstituted diindolylmethane effluxed by intestinal protein P-gp is quantified using a bi-directional transporter assay. In some embodiments, the transporter assay is a bi-directional MDR1-MDCK permeability assay.

OATP

Organic anion transporting polypeptides (OATP) form a family of influx transporters expressed in various tissues important for pharmacokinetics. Of the 11 human OATP transporters, OATP1B1, OATP1B3, and OATP2B1 are expressed on the sinusoidal membrane of hepatocytes and have been shown to facilitate the liver uptake of their substrate drugs. OATP1A2 is expressed on the luminal membrane of small intestinal enterocytes and at the blood-brain barrier, potentially mediating drug transport at these sites. Several clinically used drugs have been identified as substrates of OATP transporters (e.g. many statins are substrates of OATP1B1). Some drugs inhibit OATP transporters (e.g. cyclosporine) causing pharmacokinetic drug-drug interactions. In some embodiments, the combination therapy comprising administration of one or more modulators of CYP-450 enzymes prior to the administration of a composition comprising a substituted or substituted diindolylmethane increases the bioavailability of the substituted or unsubstituted diindolylmethane by reducing its influx into the enterocyte or hepatocyte by an OATP. In some embodiments, the percentage of a composition influxed by an OATP following the combination therapy comprising administration of one or more modulators of CYP-450 enzymes prior to the administration of a composition comprising a substituted or substituted diindolylmethane is from about 0.1% to about 50% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.1% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.2% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.3% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.4% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.5% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.6% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.7% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.8% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 0.9% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 1% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 2% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 3% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 4% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 5% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 6% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 7% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 8% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 9% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 10% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 20% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 30% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 40% of the percentage of substituted or unsubstituted diindolylmethane influxed by an OATP following a monotherapy with a composition comprising a substituted or unsubstituted diindolylmethane. In some embodiments, the percentage of a composition influxed by an OATP following the combination therapy comprising administration of one or more modulators of CYP-450 enzymes prior to the administration of a composition comprising a substituted or substituted diindolylmethane is about 50% of the percentage of substituted or unsubstituted diindolylmethane influxed by an OATP following a monotherapy with a composition comprising a substituted or unsubstituted diindolylmethane. In some embodiments, the OATP is an OATP expressed in the hepatocytes of the liver.

DIM Composition, Formulations, Routes of Administration and Delivery Dosage

In some embodiments, the second composition described herein comprises a substituted or unsubstituted diindolylmethane. In some embodiments, the second composition described herein comprises a substituted or unsubstituted diindolylmethane that has been adapted to improve bioavailability. In some embodiments, the substituted or unsubstituted diindolylmethane that has been adapted to improve bioavailability is Bioresponse-diindolylmethane (BR-DIM). In some embodiments, the second composition described herein comprises substituted or unsubstituted diindolylmethane that has not been adapted for improved bioavailability. In some embodiments, the substituted or unsubstituted diindolylmethane that has not been adapted for improved bioavailability is not BR-DIM. In some embodiments, the second composition described herein further comprises a substituted or unsubstituted retinoic acid based compound.

In some embodiments, the retinoic acid based compound is any such compound known in the art that is suitable for sublingual or buccal, oral, or topical administration. For example, in some embodiments, it is selected from a substituted or unsubstituted first generation retinoid, a substituted or unsubstituted second generation retinoid, and a substituted or unsubstituted third generation retinoid. In some embodiments, the retinoid is a substituted or unsubstituted first generation retinoid. In some embodiments, the substituted or unsubstituted first generation retinoid is selected from a substituted or unsubstituted retinol, a substituted or unsubstituted retinal, a substituted or unsubstituted tretinoin (e.g., retinoic acid or Retin A), a substituted or unsubstituted isotretinoin (e.g. Accutane™), and a substituted or unsubstituted alitretinoin. In some embodiments, the retinoid is vitamin A. In some embodiments, the retinoid is a substituted or unsubstituted second generation retinoid selected from a substituted or unsubstituted etretinate, and a substituted or unsubstituted acitretin. In some embodiments, the retinoid is a substituted or unsubstituted third generation retinoid selected from a substituted or unsubstituted tazarotene, a substituted or unsubstituted bexarotene, and a substituted or unsubstituted adapalene.

In some embodiments, the second composition described herein comprises a diindolylmethane of Formula 1:

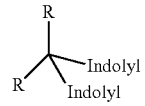

Formula 1 wherein the R groups are independently selected from hydrogen atoms and C1-C6 hydrocarbon substituents; and wherein the indolyl groups are independently selected from indole-3-yl and indole-2-yl groups; and wherein the indolyl groups are unsubstituted, or are substituted with one or more C1-C6 hydrocarbon substituents.

In some embodiments, the second composition described herein comprises an unsubstituted 3,3'diindolylmethane. In some embodiments, the second composition described herein comprises an unsubstituted 3,3'diindolylmethane and a vitamin A compound (e. g. vitamin A palmitate).

In some embodiments, the second composition described herein comprises BR-DIM. In some embodiments, the second composition described herein comprises BR-DIM and a vitamin A compound (e.g., vitamin A palmitate).

In some embodiments, the second composition comprising substituted or unsubstituted diindolylmethane is administered at a delivery dose that is sufficiently low to avoid toxicity, whilst still maintaining the required pharmaceutical effect. In some embodiments, the delivery dose of the second composition varies depending upon whether it is a natural or synthetic product. In some embodiments, the delivery dose of the second composition comprising the substituted or unsubstituted diindolylmethane is determined by whether or not the diindolylmethane has been adapted to improve bioavailability. In some embodiments, the delivery dose for a second composition comprising BR-DIM is less than the delivery dose for a second composition comprising substituted or unsubstituted diindolylmethane that has not been adapted to improve bioavailability.

In some embodiments, the delivery dose of the second composition is from about 10 mg to about 20 mg, from about 15 mg to about 25 mg, from about 20 mg to about 30 mg, from about 25 mg to about 35 mg, from about 30 mg to about 40 mg, from about 35 mg to about 45 mg, from about 40 mg to about 50 mg, from about 45 mg to about 55 mg, from about 50 mg to about 100 mg, from about 55 mg to about 150 mg, from about 60 mg to about 200 mg, from about 65 mg to about 250 mg, from about 70 mg to about 300 mg, from about 75 mg to about 350 mg, from about 80 mg to about 400 mg, from about 85 mg to about 450 mg, from about 90 mg to about 500 mg, from about 95 mg to about 550 mg, from about 100 mg to about 600 mg, from about 110 mg to about 700 mg, from about 120 mg to about 800 mg, from about 130 mg to about 900 mg, from about 140 mg to about 1000 mg, from about 150 mg to about 1100 mg, from about 200 mg to about 1200 mg, from about 250 mg to about 1300 mg, from about 300 mg to about 1400 mg, or from about 350 mg to about 1500 mg.

In some embodiments, the delivery dose of the second composition is at least 10 mg, at least 15 mg, at least 20 mg, at least 30 mg, at least 40 mg, at least 55 mg, at least 65 mg, at least 75 mg, or at least 100 mg.

In some embodiments, the delivery dose of the second composition described herein provides a daily dose of the substituted or unsubstituted diindolylmethane from about 10 mg to about 20 mg, from about 15 mg to about 25 mg, from about 20 mg to about 30 mg, from about 25 mg to about 35 mg, from about 30 mg to about 40 mg, from about 35 mg to about 45 mg, from about 40 mg to about 50 mg, from about 45 mg to about 55 mg, from about 50 mg to about 100 mg, from about 55 mg to about 150 mg, from about 60 mg to about 200 mg, from about 65 mg to about 250 mg, from about 70 mg to about 300 mg, from about 75 mg to about 350 mg, from about 80 mg to about 400 mg, from about 85 mg to about 450 mg, from about 90 mg to about 500 mg, from about 95 mg to about 550 mg, from about 100 mg to about 600 mg, from about 110 mg to about 700 mg, from about 120 mg to about 800 mg, from about 130 mg to about 900 mg, from about 140 mg to about 1000 mg, from about 150 mg to about 1100 mg, from about 200 mg to about 1200 mg, from about 250 mg to about 1300 mg, from about 300 mg to about 1400 mg, or from about 350 mg to about 1500 mg.

In some embodiments, the delivery dose of the second composition described herein provides a daily dose of substituted or unsubstituted diindolylmethane that is at least 10 mg, at least 15 mg, at least 20 mg, at least 30 mg, at least 40 mg, at least 55 mg, at least 65 mg, at least 75 mg, or at least 100 mg.

In some embodiments, the second composition comprising a substituted or unsubstituted diindolylmethane is administered in any of the above dosages, including the higher dosages, if desired. In some embodiments, the second composition comprising a substituted or unsubstituted diindolylmethane that has been adapted to improve bioavailability is administered in any of the above dosages, including the higher dosages, if desired. In some embodiments, the substituted or unsubstituted diindolylmethane that has been adapted to improve bioavailability is BR-DIM.

In some embodiments, the second composition comprising substituted or unsubstituted diinolylmethane is a formulation which is administered by sublingual or buccal route. The term "formulation which is administered by sublingual or buccal route" as used herein refers to a drug delivery formulation wherein an active compound is provided for absorption across one or more membranes in the buccal cavity, including the buccal mucosa, buccal gingiva, mucous membrane of the tongue, sublingual membrane, and the soft palate. The term encompasses all suitable solid and semi-solid dosage forms, including troches, sublingual tablets, buccal tablets (i.e. a preparation which can be placed under the tongue), effervescent tablets, lollipops, capsules, films, sprays, and gels (e.g., chitosan based gels, mucoadhesive gels). The term "buccal" is used in its broadest sense to refer to the oral cavity as a whole. In some embodiments, the composition comprising a formulation which is administered by sublingual or buccal route is also suitable for administration by oral route.

In some embodiments, the second composition comprising substituted or unsubstituted diinolylmethane is a formulation which is administered by oral route. In some embodiments, the formulation which is administered by oral route is in the form of a tablet, capsule, gel, cream, or ointment. In some embodiments, the second composition comprising a formulation which is administered by oral route is also suitable for administration by sublingual or buccal route.

In some embodiments, the delivery dose of the second composition comprising the substituted or unsubstituted diindolylmethane depends on the route of administration.

In some embodiments, the delivery dose of the second composition for sublingual or buccal administration is at least 10 mg. In some embodiments, the delivery dose of the second composition for sublingual or buccal administration is at least 15 mg. In some embodiments, the delivery dose of the second composition for sublingual or buccal administration is at least 20 mg. In some embodiments, the delivery dose of the second composition for sublingual or buccal administration is at least 25 mg. In some embodiments, the delivery dose of the second composition for sublingual or buccal administration is at least 30 mg. In some embodiments, the delivery dose of the second composition for sublingual or buccal administration is at least 35 mg. In some embodiments, the delivery dose of the second composition for sublingual or buccal administration is at least 40 mg. In some embodiments, the delivery dose of the second composition for sublingual or buccal administration is at least 45 mg. In some embodiments, the delivery dose of the second composition for sublingual or buccal administration is at least 50 mg. In some embodiments, the delivery dose of the second composition for sublingual or buccal administration is at least 55 mg. In some embodiments, the delivery dose of the second composition for sublingual or buccal administration is at least 65 mg. In some embodiments, the delivery dose of the second composition for sublingual or buccal administration is at least 70 mg. In some embodiments, the delivery dose of the second composition for sublingual or buccal administration is at least 75 mg.

In some embodiments, the delivery dose of the second composition for oral administration is at least 10 mg. In some embodiments, the delivery dose of the second composition for oral administration is at least 15 mg. In some embodiments, the delivery dose of the second composition for oral administration is at least 20 mg. In some embodiments, the delivery dose of the second composition for oral administration is at least 25 mg. In some embodiments, the delivery dose of the second composition for oral administration is at least 30 mg. In some embodiments, the delivery dose of the second composition for oral administration is at least 35 mg. In some embodiments, the delivery dose of the second composition for oral administration is at least 40 mg. In some embodiments, the delivery dose of the second composition for oral administration is at least 45 mg. In some embodiments, the delivery dose of the second composition for oral administration is at least 50 mg. In some embodiments, the delivery dose of the second composition for oral administration is at least 55 mg. In some embodiments, the delivery dose of the second composition for oral administration is at least 65 mg. In some embodiments, the delivery dose of the second composition for oral administration is at least 70 mg. In some embodiments, the delivery dose of the second composition for oral administration is at least 75 mg.

In some embodiments, the delivery doses of the second composition for administration by sublingual or buccal route and by oral route are the same. In some embodiments, the delivery dose of the second composition for administration by sublingual or buccal route is less than the delivery dose for administration by oral route.

In some embodiments, the second composition described herein comprises substituted or unsubstituted diindolylmethane in a dose which is a fraction of the daily dose, such as a half of the daily dose, or a quarter of the daily dose, and thus is present in a half or a quarter of any of the dosages recited above. In these embodiments, each dose fraction is taken separately over time to spread the dose across the day.

In some embodiments, the second composition described herein further comprises a substituted or unsubstituted retinoic acid based component. In some embodiments, the retinoic acid based component is administered at a dosage that it is sufficiently low to avoid toxicity, whilst still maintaining the required pharmaceutical effect. In some embodiments, the delivery dosage of the retinoic acid based component depends on the bioavailability of the same. In some embodiments, the bioavailability of the substituted or unsubstituted retinoic acid based component varies depending upon whether it is a natural or synthetic product. In some embodiments, the bioavailability of the substituted or unsubstituted retinoic acid based component varies depending on whether it has been adapted to improve its bioavailability. In some embodiments, the delivery doses of the second compositions described herein provides a daily dose of the substituted or unsubstituted retinoic acid based component from about 0.05 mg to about 3 mg, from about 0.1 to about 5 mg, from about 1 mg to about 15 mg, from about 10 mg to about 45 mg, from about 25 mg to about 100 mg, from about 75 mg to about 200 mg, from about 150 mg to about 250 mg. In some embodiments, the delivery doses of the second compositions described herein provides a daily dose of the substituted or unsubstituted retinoic acid based component that is at least 0.05 mg, at least 0.1 mg, at least 0.2 mg, at least 0.4 mg, at least 1 mg, at least 5 mg, or at least 10 mg. In some embodiments, the delivery doses of the second compositions described herein provides a daily dose of the substituted or unsubstituted retinoic acid based component that is up to 15 mg, up to 10 mg, up to 9 mg, up to 8 mg, up to 7 mg, up to 6 mg, up to 5 mg, up to 2.5 mg, up to 2 mg, up to 1 mg, or up to 0.5 mg.

In some embodiments, daily dosage of the second composition comprising a substituted or unsubstituted diindolylmethane and optionally a substituted or unsubstituted retinoic acid based component is provided in the form of one or more unit doses. In some embodiments, daily dosage of the second composition comprising a substituted or unsubstituted diindolylmethane and optionally a substituted or unsubstituted retinoic acid based component is provided in the form of 2 to 4 unit doses. In these embodiments the two or more unit doses are taken during the course of a single day, such as one unit dose in the morning and one unit dose in the evening, or four unit doses spread evenly across the day, or two unit doses simultaneously twice a day.

In some embodiments, a pharmaceutical compositiuion is provided compriding a first component comprising a modulator of a CYP450 enzyme and a second component comprising a substituted or an unsubstituted diindolylmethane. In some cases, the first component comprising the modulator of CYP450 is same as the first composition comprising at least one inhibitor of one or more CYP-450 enzymes selected from a group consisting of CYP1A1, CYP1A2, CYP2A, CYP2B, CYP2B1, CYP2C, CYP2C6, CYP2C9, CYP2C19, CYP2D6, CYP2E1, CYP3A, CYP3A2, CYP3A4, CYP4A1, and CYP4B1The CYP450 modulator, in some cases, comprises a modulator of a CYP450 enzyme selected from CYP1A1, CYP1A2, CYP2D6, CYP2C8, CYP2C9, CYP3A4, CYP2C19, CYP19A1, or combinations thereof.

The second component comprises, in some embodiments, a substituted or unsubstituted diindolylmethane. In some cases, the second component comprising the substituted or unsubstituted diindolylmethane is same as the second composition comprising the substituted or unsubstituted diindolylmethane, as described above. In some embodiments, the second component comprises a substituted or unsubstituted diindolylmethane that has been adapted to improve bioavailability. In some embodiments, the substituted or unsubstituted diindolylmethane that has been adapted to improve bioavailability is Bioresponse-diindolylmethane (BR-DIM). In some embodiments, the second component comprises substituted or unsubstituted diindolylmethane that has not been adapted for improved bioavailability. In some embodiments, the substituted or unsubstituted diindolylmethane that has not been adapted for improved bioavailability is not BR-DIM. In some embodiments, the second component further comprises a substituted or unsubstituted retinoic acid based compound. In some embodiments, the pharmaceutical composition comprises a third component comprising a substituted or an unsubsituted retinoic acid based compound. The retinoic acid based compound, in some cases, is same as the retinoic acid based component described above.

In some embodiments, the first component comprises about 10 mg to about 100 mg of the modulator of the CYP450 enzyme. In some embodiments, the first component comprises about about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 100 mg of the modulator CYP450 enzyme. In some examples, the CYP450 modulator is a modulator is CYP1A2, such as quercetin. The second component, in some cases, comprises about 15 mg to about 25 mg, about 25 mg to about 35 mg, about 35 mg to about 45 mg, about 45 mg to about 55 mg, about 55 mg to about 65 mg, about 65 mg to about 75 mg, about 75 mg to about 85 mg, or about 85 mg to about 100 mg of the substituted or unsubstituted diindolylmethane. In some cases, the second component comprises about 45 mg of the substituted or unsubstituted diindolylmethane.

The pharmaceutical composition comprises, in some embodiments, a ratio between the first component and the second component, said ratio (first component:second component) is between about 66:1, about 45:1, about 40:1, about 35:1, about 30:1, about 25:1, about 20:1, about 15:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:5, about 1:10, about 1:20, or about 1:30. In some cases, the ratio between the first component and the second component is about 20:1, 19:1, 18:1, 17:1, 16:1, 15:1, 14:1, 13:1, 12.9:1, 12.8:1, 12.7:1, 12.6:1, 12.5:1, 12.4:1, 12.3:1, 12.2:1, 12.1:1, 11:1, 11.9:1, 11.8:1, 11.7:1, 11.6:1, 11.5:1, 11.4:1, 11.3:1, 11.2:1, 11.1:1, 10.9:1, 10.8:1, 10.7:1, 10.6:1, 10.5:1, 10.4:1, 10.3:1, 10.2:1, 10.1:1, 10:1, 9:1, 8:1, 7:1, 6:1, 5:1, 4:1, 3:1, 2:1, or 1:1.

The pharmaceutical composition, in some embodiments, is such that a single dose of the furst component comprises about 300 mg to about 750 mg of the modulator of the CYP450 enzyme, a single dose of the second component comprises about 30 mg to about 90 mg of the substituted or unsubstituted diindolylmethane, and a single dose of the third component comprises about 200 µg to about 1000 µg of a vitamin A compound, such as retinyl palmitate. The pharmaceutical composition, in some embodiments, is such that a daily dose of the first component comprises about 300 mg to about 2250 mg of the modulator of the CYP450 enzyme, a daily dose of the second component comprises about 30 mg to about 270 mg of the substituted or unsubstituted diindolylmethane, and a daily dose of the third component comprises about 200 µg to about 3000 µg of a vitamin A compound, such as retinyl palmitate.

The pharmaceutical composition, in some cases, comprises the first and the second component in a same dosage form or in different dosage forms. In some cases, the second component and the third component are in a same dosage form. Dosage forms include, but are not limited to, tablets, capsules, sublingual or buccal dosage forms. In certain cases, the first component is in a dosage form for oral administration and the second component is in a dosage form for sublingual or buccal administration.

In some embodiments, the bioavailability, AUC, Cmax of the substituted or unsubstituted diindolylmethane is increased in the pharmaceutical composition, compared to a control composition that does not comprise the first component comprising the modulator of the CYP450 enzyme. The increases in bioavailability, AUC, Cmax, or combinations thereof are, in some cases, between about 1-fold to about 10-folds, about 10-folds to about 20-folds, about 20-folds to about 30-folds, about 30-folds to about 40-folds, about 40-folds to about 50-folds, about 50-folds to about 60-folds, about 60-folds to about 70-folds, about 70-folds to about 80-folds, about 80-folds to about 90-folds, or about 90-folds to about 100-folds. In some embodiments, the Tmax of the substituted or unsubstituted diindolylmethane is decreased in the pharmaceutical composition, compared to a control composition that does not comprise the first component comprising the modulator of the CYP450 enzyme. The decrease in Tmax is, in some cases, between about 1-fold to about 10-folds, about 10-folds to about 20-folds, about 20-folds to about 30-folds, about 30-folds to about 40-folds, about 40-folds to about 50-folds, about 50-folds to about 60-folds, about 60-folds to about 70-folds, about 70-folds to about 80-folds, about 80-folds to about 90-folds, or about 90-folds to about 100-folds.

In some embodiments, the pharmaceutical composition is such that the metabolism of the substituted or unsubstituted diindolylmethane by the CYP450 modulator is reduced by about 0.1% to about 10% compared to a control composition that does not comprise the first component. The percentage of reduction is, in some cases, between about 0.1% to about 1%, about 2% to about 5%, about 7% to about 8%, about 9% to about 10%. In some embodiments, the pharmaceutical composition is such that the metabolism of the substituted or unsubstituted diindolylmethane by CYP1A2 is reduced by about 0.1% to about 10% compared to a control composition that does not comprise the first component. The percentage of reduction is, in some cases, between about 0.1% to about 1%, about 2% to about 5%, about 7% to about 8%, about 9% to about 10%.

In some embodiments, the pharmaceutical composition is such that the percentage of the substituted or unsubstituted diindolylmethane metabolized by the CYP450 enzyme is reduced by about 0.1% to about 10% compared to a control composition that does not comprise the first component. The percentage of reduction is, in some cases, between about 0.1% to about 1%, about 2% to about 5%, about 7% to about 8%, about 9% to about 10%. In some embodiments, the pharmaceutical composition is such that the percentage of the substituted or unsubstituted diindolylmethane metabolized by the CYP1A2 is reduced by about 0.1% to about 10% compared to a control composition that does not comprise the first component.

Non-limiting examples of the modulator of CYP450 enzyme comprise quercetin, black raspberry, blueberry, ellagic acid, pomegranate, walnuts, blackcurrants, soy, soybean, black soybean, turmeric, apiaceous vegetable, cruciferous vegetables, allium vegetables, garden cress, watercress, yellow onion, kale, alfalfa sprouts, green beans, broccoli, chili powder, daizein, garlic, apple, apricot, chamomile, peppermint, dandelion, green tea, black tea, rooibos tea, itadori tea, coffee, caffeine, caffeic acid, grapes, wine, peanuts, honey, medium-chain triglycerides, coconut and coconut oil, honeycomb, fish oil, rosemary, N-acetyl cysteine, chrysin, quercetin, resveratrol, myricetin, cur-cumin, curry powder, astaxanthin, algae, yeast, salmon, trout, krill, shrimp, crayfish, chicory root, or combinations thereof.

Methods for Preparation

In some embodiments, are provided, methods for preparing the compositions described herein, for use in the methods described herein, of treating acne or rosacea. In some embodiments, using the methods described herein, a composition suitable for sublingual or buccal administration is prepared. In some embodiments, using the methods described herein, a comparative composition suitable for oral administration is prepared. In some embodiments, using the methods described herein, a composition suitable for both sublingual or buccal and oral administration is prepared.

In some embodiments, any methods known in the art for blending or mixing various components of the composition are employed. In some embodiments, the methods employed are methods for blending and/or mixing powders. In some embodiments, the method comprises mixing substituted or unsubstituted diindolylmethane with one or more pharmaceutically acceptable excipients and/or additives, and optionally with a substituted or unsubstituted retinoic acid based component, to form the composition. In some embodiments, the substituted or unsubstituted diindolylmethane, and the substituted or unsubstituted retinoic acid based component are each, separately from each other, mixed with one or more pharmaceutically acceptable excipients and/or additives before being mixed together to form the composition. In some embodiments, the substituted or unsubstituted diindolylmethane, the substituted or unsubstituted retinoic acid based component, and/or pharmaceutically acceptable excipients are added sequentially to the mixture during the mixing process.

In some embodiments, the selection of the pharmaceutically acceptable excipients and the method of blending are adapted in order to overcome any mixing, flow, and fill issues or punch issues with the composition. In some embodiments, the composition comprising a substituted or unsubstituted diindolylmethane is provided in micro-encapsulated form, such that the powder particles have a tendency to clump together. In some embodiments, the composition comprising a first component, comprising a substituted or unsubstituted diindolylmethane is blended using a method that is adapted to avoid creating hot spots of increased concentrations of the active ingredients. In some embodiments, the composition comprising a substituted or unsubstituted diindolylmethane, and optionally a substituted or unsubstituted retinoic acid based component, is blended using a method that involves short processing/blending times, to protect the composition from light and air, wherein the composition is hygroscopic and light sensitive. In some embodiments, the composition comprising a substituted or unsubstituted diindolylmethane, and optionally a substituted or unsubstituted retinoic acid based component, is prepared in the form of a powder, and the powder is protected from both light and air during storage.

In some embodiments, one or more of microcrystalline cellulose, magnesium silicate, tricalcium phosphate, and magnesium stearate (a traditional lubricant) are employed as pharmaceutically acceptable additives and excipients, in preparing the compositions described herein, to help with flow characteristics and/or lubrication. In some embodiments, other pharmaceutically acceptable additives and excipients known in the art are employed if desired. In some embodiments, the composition comprises from about 50.0% to about 65.0% by weight of tri-calcium phosphate. In some embodiments, the composition comprises from about 55.0% to about 60.0% by weight, or from about 57.0 to about 59.0% by weight of tri-calcium phosphate. In some embodiments, the composition comprises about 58% by weight of tri-calcium phosphate. In some embodiments, the composition comprises about 58.3% by weight of tri-calcium phosphate.

In some embodiments, the correct blending of all ingredients is desirable in achieving uniform capsule fills of the compositions as described herein. In some embodiments, the correct blending of all ingredients is desirable in achieving uniform capsule fills of the compositions as described herein. In some embodiments, a V-blender is highly effective for successful mixing. In some embodiments, a minimum 316 grade stainless steel vessel is used for the mixing process. In some embodiments, sieving is performed at one or more of the start, the middle, and the end of the mixing process. In some embodiments, blend studies to confirm blend uniformity are completed to validate the method and formulation, using methods and techniques known in the field.

In some embodiments, the first composition described herein, comprising modulators of one or more cytochrome P450 enzymes is mixed with pharmaceutically acceptable carriers or excipients known to those of skill in the art, and administered in dosage forms including but not limited to, oral administration in the form of juice, powders, tablets, suspension, emulsifiers, capsules, granules, troches, pills, suspensions, spirits, syrups, and limonades; injectable administration intravenously or otherwise; topical administration in the form of ointments, solids, suspensions, powders, paps, suppositories, aerosols, cataplasmas, liniments, lotions, enemas, and emulsifiers. In some embodiments, well-known excipients in the form of solid or liquid are used. The several non-limiting examples of excipients used to administer the dosage forms include: excipients in powders and other oral powders such as lactose, crystalline cellulose, starch, dextrin, calcium phosphate, calcium carbonate, synthetic and natural aluminum dioxide, magnesium oxide, dried aluminum hydroxide, magnesium stearate, and sodium bicarbonate; excipients in topical powders such as zinc oxide, talc, starch, kaolin, borate powder, zinc stearate, magnesium stearate, magnesium carbonate, precipitated calcium carbonate, bismuth subgallate, and potassium aluminum sulfate powder; excipients in liquids such as water, glycerin, propylene glycol, sweet-taste syrup, ethanol, fatty oil, ethylene glycol, polyethylene glycol, and sorbitol; excipients in ointments such as hydrophobic or hydrophilic base (including oil soluble base, water-soluble base, and suspended base) prepared by mixing fat, fatty oil, lanoline, Vaseline, glycerin wax, Japan wax, paraffin, paraffin sulphate, resins, higher alcohols, plastics, glycols, water, or surfactant.

In some embodiments, first compositions discussed herein are administered in any of the forms considered herein, or otherwise known to those of skill in the art. In some embodiments, the first composition is administered orally in a liquid form, either as an extract, concentrated extract, or other liquid form.

Certain Definitions

Unless defined otherwise, all technical and scientific terms used herein have the same meaning as is commonly understood by one of skill in the art to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, are also effective and safe.

The term "patient", "subject", or "individual" are used interchangeably. As used herein, they refer to individuals suffering from a disorder, and the like, and encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. In some embodiments of the methods and compositions provided herein, the individual is a mammal. In preferred embodiments, the individual is a human.

The terms "treat", "treating", "treatment", and other grammatical equivalents, as used herein, include alleviating, abating, or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "administer", "administering", "administration", and the like, as used herein, refer to the methods that may be used to enable delivery of compounds or compositions to the desired site of biological action. These methods include, but are not limited to, sublingual or buccal routes, oral routes, intraduodenal routes, parenteral injection (including intravenous, subcutaneous, intraperitoneal, intramuscular, intravascular, or infusion), topical, and rectal administration. Those of skill in the art are familiar with administration techniques that can be employed with the compounds and methods described herein.

The term "acceptable", as used herein, with respect to a formulation, composition, or ingredient, means having no persistent detrimental effect on the general health of the individual being treated.

The term "pharmaceutically acceptable", as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "DIM", as used herein, refers to a substituted or unsubstituted diindolylmethane compound.

The term "BR-DIM", or "BioResponse DIM", as used herein, refers to an unsubstituted DIM, provided by BioResponse, LLC.

The term "maximum concentration", or Cmax, as used herein, refers to the maximum (or peak) serum concentration that the substituted or unsubstituted diindolylmethane achieves in the plasma after it has been administered and prior to the administration of a second dose.

The term "time of maximum concentration", or Tmax, as used herein, refers to the time at which the Cmax is observed.

The term "area under the curve", or AUC, or $AUC_{0-inf}$, as used herein, refers to the area under the curve, also known as the definite integral, in a plot of concentration of drug in blood plasma against time.

The term "unit dose", as used herein, refers to an amount of substituted or unsubstituted diindolylmethane contained in one discreet pharmaceutical dosage form. Examples of pharmaceutical dosage forms that contain a unit dose include but are not limited to a tablet, a capsule, a buccal tablet, a sub-lingual tablet, an orally-disintegrating tablet, an effervescent tablet, a lollipop, a lozenge, a troche, a liquid solution or suspension, powder or liquid or solid crystals packed within a single tablet or capsule, a cream, a gel, an ointment, or a lotion.

EXAMPLES

The following specific, non-limiting examples are to be construed as merely illustrative, and do not limit the present disclosure of the scope of the disclosure. Without further elaboration, it is believed that one skilled in the art can, based on the description herein, utilize the present disclosure to its fullest extent.

Example 1

Effect of the Combination Therapy on the PK Profile of DIM in Plasma

The objective of this study is to determine the pharmacokinetic (PK) profile of a diindolylmethane (DIM) formulation in plasma, synthesized and prepared using any of the methods described above, administered after single or multiple doses of CYP-450 modulators. Participants are grouped into (a) Group 1: DIM administered after a prior dose of a CYP-450 modulator (b) Group 2: DIM administered without a prior dose of a CYP-450 modulator.

Part 1: Plasma Pharmacokinetics of DIM Formulation after a Single Oral 75 mg Dose Participants of Groups 1 and 2 are administered, with or without a prior dose of a CYP-450 modulator respectively, a single 75 mg dose of the DIM formulation. Blood samples are drawn from the participants at baseline and at 0.5, 1.0, 1.5, 2, 3, 4, 6, 8, 9 h, following administration of the DIM formulation dosage on day 1.

Part 2: Pharmacokinetic Profile of DIM following Bi-Daily Dosing for 4 Weeks.

In the second part of the study, participants of Groups 1 and 2 are administered, with or without a prior dose of a CYP-450 modulator respectively, on days 1 through 28, a single dose of 75 mg of the DIM formulation twice daily. Blood samples are taken at the completion of treatment as per the schedule described for Part 1.

For each part of the study, pharmacokinetic parameters, including but not limited to, maximum concentration ($C_{max}$), time to $C_{max}$ ($T_{max}$), biological half-life (t½), and area under the concentration time curve ($AUC_{0-inf}$) are calculated for all subjects who complete the respective part. A one-compartment elimination model fits the data.

Example 2

Determination of Plasma Levels of BioResponse Diindolylmethane (BR-DIM) Following Single and Multiple Oral Dosing, and after Prior Treatment with Specific Substrates of Hepatic CYP Enzyme Activity and of P-gp Transport Function The primary objectives of this study are:
1. To measure the pharmacokinetics of nutritional-grade, absorption-enhanced diindolylmethane (BR-DIM) BR-DIM in the plasma following single and multiple dosing in healthy male volunteers.
2. To determine the effect of DIM on the activity of certain hepatic CYP enzymes as well as enteric P-gp as assessed by measuring changes in the levels of specific substrates of these enzymes (5-drug probe cocktail)/efflux transporter.
3. Following the oral administration of specific nutritional grade food supplements reported to be inhibitors or inducers of certain CYP enzymes, to measure the effect of these supplements on the PK profile of BR-DIM in healthy male volunteers.

Part 1a

All participants on day one receive a single daily oral dose of placebo together with a 5-drug probe cocktail and P-gp-s; blood and urine samples over a 9-hour period (1,2,3,4,6, and 9 hr) will be taken to determine the activity of the specific CYP enzyme or transporter as measured by the plasma and urinary levels of the respective CYP probe substrate.

After a suitable wash out period, a single oral dose of 75 mg BioResponse Diindolylmethane (BR-DIM) is given, after which blood samples are taken to determine the 9h PK profile of BR-DIM.

Part 1b

After a suitable wash-out period, a single oral dose of 75 mg of BR-DIM is given concomitantly with the 5-drug probe cocktail and blood and urine samples are taken to establish the levels of the respective CYP probe substrate or trasnporter, as well as the PK profile for BR-DIM.

An exemplary probe cocktail contains: caffeine (to study the effect of CYP1A2), metoprolol (to study the effect of CYP2D6), losartan/celecoxib (to study the effect of CYP2C9), midazolam to study the effect of CYP3A, and fexofenadine or other non-metabolized drug that inhibits the activity of the enterocyte efflux transporter P-glycoprotein (P-gp).

Part 2

Participants receive, on days 1-28, a single oral dose of 75 mg BR-DIM twice daily. Blood samples are taken at the completion of treatment. At the end of the 28-day period, the final dose of BR-DIM together with the 5-drug probe cocktail is administered. Blood and urine samples are taken as per the schedule described for day 1.

Part 3

Once the results from Part 2 have been analyzed, the same participants who completed both Parts 1(a,b) and 2, are administered one or more nutritional grade food supplements that are expected to inhibit or induce the hepatic CYP enzymes or transporter being studied. Thereafter, the participants are subjected to the same procedures as are detailed in Parts 1 and 2 above. Blood and urine are collected periodically throughout the study (and prior to inclusion in the study to assess urinary levels of cotinine and DIM obtained from the diet). After completion of study intervention, participants are followed at 1 week to record any observed adverse effects.

The study participants are healthy men and women with the following inclusion exemplary criteria:
1. Nonsmoker confirmed by urine cotinine test
2. Life expectancy>=12 months
3. Hemoglobin>10 g/dL
4. Absolute granulocyte count>1,500/mm^3
5. Creatinine<2.0 mg/dL
6. Albumin>3.0 g/dL
7. Bilirubin<1.8 mg/dL
8. AST and ALT<110 U/L
9. Alkaline phosphatase<300 U/L
10. Body mass index=<30
11. No acute, unstable, chronic, or recurring medical conditions
12. No strict vegetarians, or consumption of cruciferous vegetables immediately prior to, or during, the study period.
13. Participants who have stopped eating cruciferous vegetables within the past 2 weeks and agree to refrain from eating them for the duration of the study are eligible
14. Cruciferous vegetables include broccoli, cabbage (including coleslaw), cauliflower, bok-choy, brussels sprouts, collards, kale, kohlrabi, mustard greens, rutabaga, turnip, and watercress
15. Participants must have refrained from eating grapefruit or grapefruit juice for two weeks prior to inclusion into the study, as well as throughout the study. Other food products or supplements will also be excluded throughout the study.
16. No serious drug allergies or other serious intolerance or allergies
17. Mild seasonal allergies allowed
18. No chronic conditions, including headaches, dysphoria, fatigue, dizziness, blurred vision, insomnia, rhinorrhea, nausea, vomiting, abdominal pain, diarrhea, constipation, menopausal hot flashes/night sweats, or clinically significant premenstrual syndrome
19. No serious, acute, or chronic illness
20. No requirement for chronic drug therapy
21. No alcohol ingestion within 48 hours of study treatment
22. No investigational drugs within the past 3 months
23. No prior chemotherapy
24. No concurrent regular medications or hormones
25. No recent change in medications or dosage of medications
26. No concurrent regular supplements or vitamins
27. No concurrent over-the-counter medications or food supplements
28. If participants are coffee drinkers, then it is requested that the drinking habits (number or strength of coffee drinks) will not change for 2 weeks before or during the study.

Example 3

Improved Efficacy of Rosacea Treatment by Prior Administration of a CYP450 Modulator The objective of this study is to determine the efficacy of a diindolylmethane (DIM) formulation in treating rosacea following a 4-week treatment with DIM, administered after a prior dose of a CYP-modulator. The DIM formulation for this study is synthesized and prepared using any of the methods described above.

Participants are grouped into (a) Group 1: DIM administered after prior dose of a CYP-modulator(b) Group 2: DIM administered without a prior dose of a CYP-450 modulator Participants of Groups 1 and 2 are administered orally, or via sublingual route, with or without a prior dose of a CYP-450 modulator respectively, on days 1 through 28, a single dose of 75 mg of the DIM formulation twice daily. After completion of the study, participants are requested to self-report on certain skin parameters related to rosacea, e.g., redness, flushing, dryness, red bumps, or swelling.

Example 4

Improved Efficacy of Acne Treatment by Prior Administration of DIM

The objective of this study is to determine the efficacy of a diindolylmethane (DIM) formulation in treating acne following a 4-week treatment with DIM, administered after a prior dose of a CYP-modulator. The DIM formulation for this study is synthesized and prepared using any of the methods described above.

Participants are grouped into (a) Group 1: DIM administered after prior dose of a CYP-modulator (b) Group 2: DIM administered without a prior dose of a CYP-450 modulator.

Participants of Groups 1 and 2 are administered orally, or via sublingual route, with or without a prior dose of a CYP-450 modulator respectively, on days 1 through 28, a single dose of 75 mg of the DIM formulation twice daily. After completion of the study, skin biophysical parameters related to acne; including but not limited to skin sebum and stratum corneum hydration levels; transepidermal water loss values; pH; and erythema and hair growth parameters such as total number, density and proportion of anagen hair, of the study participants are assessed.

Example 5

Multiple Dose PK Study of a Sublingual Formulation of DIM+Vitamin A Taken with or without Quercetin Clinical hypothesis: Plasma exposure of DIM is greater when the ACCUMAX SL is taken in combination with Quercetin compared with ACCUMX SL alone.

Study objectives: Primary—To assess the effects of Quercetin supplementation on plasma levels of DIM following dosing with ACCUMAX SL.

Study endpoints: Primary—Plasma levels of DIM following treatment with either one week's administration of Quercetin followed by 2 weeks' administration of Quercetin and ACCUMAX sublingual (ACCUMAX SL) or no treatment for one week and then 2 weeks' administration of ACCUMAX SL.

Study design: Randomized, open-label, parallel trial.

Population: 14 healthy adult males and females. An equal gender ratio is not required for this study.

Inclusion criteria:
1. The participant is able to read and understand the Informed Consent Form (ICF), and understand study procedures.
2. The participant has signed the ICF.
3. The participant is willing to comply with the dosing schedule and associated fasting requirements.
4. Aged between 18 and 45 years inclusive at screening.
5. The participant is a non-nicotine user (has not smoked or used other nicotine products [e.g., chewing tobacco, gum, patch, electronic-cigarette]) and has not used the products within 3 months prior to screening
6. BMI≥20 to ≤30 kg/m2.
7. Willing to maintain their habitual consumption of cruciferous vegetables for the duration of the study.
8. Willing to not consume grapefruit or grapefruit juice from screening and for the duration of the study.
9. Willing to not consume food supplements or vitamins from screening and for the duration of the study.
10. Willing to not consume more than 14 units of alcohol per week from screening and for the duration of the study.
11. Willing to not consume alcohol within 48 hours of all study visits.
12. Willing to limit their daily intake of caffeine to not exceed 500 mg caffeine per day from screening and for the duration of the study.
13. Female participants who are willing to use an acceptable form of contraception (including abstinence, combined oestrogen/progesterone medication, or intrauterine contraceptive devices). Where hormonal contraception is used, the participant needs to have been on stable treatment for 3 months prior to screening and agrees that no changes will be made to this treatment throughout the study.
14. The participant is, in the opinion of the investigator, healthy on the basis of a physical examination, self-reported medical history, vital signs, Electrocardiogram (ECG), and the results of routine laboratory tests.
15. Participant is available to attend visits for the duration of the study.

Exclusion Criteria:
1. Treatment with retinoids within 6 months of enrolment in this study.
2. Serious drug allergies or other serious intolerances. Including but not limited to a known sensitivity to vitamin A or DIM, or a history of any allergy that in the opinion of the investigator would contraindicate participant participation.
3. Significant acute, unstable, chronic (including symptoms of headaches, dysphoria, fatigue, dizziness, blurred vision, insomnia, rhinorrhoea, nausea, vomiting, abdominal pain, diarrhoea, constipation, menopausal hot flashes/night sweats, or clinically significant premenstrual syndrome) or recurring medical conditions as judged by the investigator.
4. Clinically significant psychiatric, cardiovascular, respiratory, hepatic, renal, gastrointestinal, endocrine, neurological (particularly myasthenia gravis), immunological, or haematological disease or abnormality, as determined by the investigator.
5. Prior treatment with chemotherapy.
6. Currently participating in another study with an investigational or non-investigational drug or device, or has participated in another clinical trial within 3 months prior to signing the ICF.
7. Participants whose clinical laboratory test values are outside the accepted reference range at screening, with values that are deemed as clinically significant by the investigator.
8. Participants who demonstrate a reactive screen for hepatitis B surface antigen, hepatitis C antibody, or HIV antibody.
9. Pregnant confirmed by urine pregnancy test, or breast-feeding/lactating females.
10. The participant has a known history of allergic response(s) to any of the ingredients in Quercetin or its components.
11. Currently consuming more than two portions of cruciferous vegetables per day.
12. Currently taking regular prescribed concurrent medications or hormones (other than oral contraception)
13. Use of over the counter medications or herbal remedies (except for over the counter analgesics, cold remedies and anti-histamines) from screening and for the duration of the study.
14. History of alcohol, narcotic, benzodiazepine, or other substance abuse or dependence within the 12 months preceding Visit 1.
15. Positive urine drug screen at any visit at Surrey CRC (i.e., amphetamines, barbiturates, benzodiazepines, cannabinoids, cocaine, or opiates). A repeat test will not be allowed.
16. Positive urine cotinine test at screening. A repeat test will not be allowed.
17. Positive alcohol breath test at any visit to Surrey CRC. A repeat test will not be allowed.
18. Participants who report donating greater than 150 ml of blood or donating plasma within 28 days before dosing.
19. Any condition that, in the investigator's opinion, compromises the participant's ability to meet protocol requirements or to complete the study.

No waivers from the Protocol will be allowed.

Discontinuation and withdrawal of participants from the study: Any participant may voluntarily discontinue participation in this study at any time. The investigator may also, at their discretion, discontinue the participant from participating in this study at any time, and must do so if any of the following criteria are met:

Positive alcohol breath test at any visit.

Positive urine test for drugs of abuse or cotinine at any visit.

Positive pregnancy test at any visit.

Concomitant use of any medication which may interfere with study outcome, participant safety and study products throughout the study.

Any other reason that, in the investigator's opinion, compromises the participant's ability to meet protocol requirements or to complete the study.

The reason for termination will be recorded in the Case Report Form (CRF).

A participant may withdraw (or be withdrawn) from the study prematurely for the following reasons:
Withdrawal of consent.
  AE (AE section must be completed).
  Protocol deviation.
  Lost to follow-up.
  Other (must be specified).
If a participant discontinues/withdraws prior to randomisation to study treatment (Visit 2) they will be considered as a screen failure. Screen failures can be replaced to ensure that 14 participants are randomised to ensure that 12 participants complete visit 4.

A follow-up visit must be performed if premature discontinuation/withdrawal following randomisation at Visit 2 takes place. The procedures performed should be as per the end of study (EOS) visit indicated on the study flow chart.

Study Products (Formulations, Route of Administration and Dose Regimen):
  Quercetin (Food supplement)
    One single daily dose of 500 mg Quercetin given as an oral formulation
    Taken daily for 3 weeks (treatment group A) (Days 1-21)
    To be taken in the morning within 2 hours of waking and before food is consumed
    The daily 500 mg dose of quercetin has been chosen as it is a dose that is commonly recommended as a minimum dose for use as a food supplement.
  ACCUMAX SL (Food supplement)
    Oral microencapsulated diindolylmethane and Vitamin A given as a sublingual (SL) formulation
    One SL tablet will be taken and allowed to dissolve under the tongue twice a day for 14 days (Days 8-21) in both groups A and B
    SL tablets will be taken in the morning after an overnight fast of at least 8 hours and in the evening before going to bed (not with food)
    Each SL tablet contains 45 mg DIM and 400 µg retinol equivalents (RE), 45 mg DIM and 732.8 µg of retinyl palmitate, or 45 mg DIM and 400 µg retinyl palmitate
    Total daily dose of 90 mg DIM and 800 µg retinol equivalents
    A daily dose of 90 mg DIM and 800 µg RE has been chosen as this is comparable to the daily oral dose of a capsule formulation SKIN ACCUMAX™ that has been marketed worldwide for many years.
PK Parameters: Plasma PK Concentrations.
Main Parameters of Safety: Adverse Events.
Assessment Schedule:
  Visit 1—Screening (Day −28 to Day −1)
    Informed consent
    Demography
    Medical History
    Concomitant medications
    Full Physical Exam
    ECG
    Height/Weight/BMI
    Blood sample for Haematology, Biochemistry, virology
    Urinalysis
    Urine drugs of abuse
    Urine Cotinine
    Urine pregnancy (female participants only)
    Breath Alcohol
    Vital Signs: blood pressure, heart rate, oral temperature, respiratory rate
    Assessment of inclusion/exclusion criteria
  Visit 2-Day 1
    Assessment of inclusion/exclusion criteria
    Randomisation
    Urine pregnancy (female participants only)
    Urine drugs of abuse
    Urine Cotinine
    Breath Alcohol
    Product (Quercetin only) Dispensing to Group A
    Dosing (single dose taken at the visit) by Group A
    Adverse Events
    Concomitant Medications
  Group A participants will then self-dose at home once daily for 7 days. Time of dosing will be recorded in a diary. The participants should take the dose within 2 hours of waking and before consuming food.
  Visit 3-Day 8
    Assessment of inclusion/exclusion criteria
    Urine Pregnancy (female participants only)
    Urine drugs of abuse
    Urine Cotinine
    Breath Alcohol
    Product (Quercetin only) Returns Accountability
    Product (Quercetin and ACCUMAX SL for Group A or just ACCUMAX SL for Group B) Dispensing
    Dosing (that days dose taken at the visit for both groups)
    Adverse Events
    Concomitant Medications
  Participants will then leave the SCRC and will self-dose at home for 2 weeks. All participants must take the ACCUMAX SL twice a day (once in the morning after an overnight fast of at least 8 hours and in the evening before going to bed (not with food)). There must be at least 8 hours between the morning and evening doses. Group A participants also taking Quercetin must take this once a day within 2 hours of waking and before consuming food. This can be taken at the same time as the ACCUMAX SL. Time of dosing will be recorded in a diary as well as any adverse events that have been noted by the participant.
  Visit 4-Day 21
    Assessment of inclusion/exclusion criteria
    Urine pregnancy (female participants only)
    Urine drugs of abuse
    Urine Cotinine
    Breath Alcohol
    Vital Signs
    Full Physical Exam
    Product (Quercetin and ACCUMAX) Returns Accountability
    Product Dispensing (Quercetin and ACCUMAX SL (Group A) or just ACCUMAX SL (Group B))
    Dosing (that days dose taken at the visit for both groups)
    PK blood sampling—0 (pre-dose), 0.5, 1, 1.5, 2, 3, 4, 6, 9, 12 hours
    Adverse Events
    Concomitant Medications
  Participants will take the study products daily at home as follows:
    Group A: Quercetin for 1 week followed by 2 weeks of Quercetin and ACCUMAX SL
    Group B: 1 week no Quercetin and then 2 weeks of just ACCUMAX SL
  Whilst dosing at home participants will also complete a diary to record times of dosing, adverse events and concomitant medications.

Participants randomised to Group A will need to take the Quercetin in the morning within 2 hours of waking (with the exception of Visits 2, 3 and 4) and before consuming any food. The ACCUMAX SL tablet must be taken in the morning after an overnight fast of at least 8 hours and in the evening before going to bed (not with food). Each product should be taken ideally at the same time in the morning and evening. There must be at least 8 hours between the morning and evening doses. Participants will be asked to record the times of their dosing in a diary.

If a participant misses a single dose then this should be taken as soon as possible thereafter. If more than one consecutive dose is missed, then the normal dosing regimen should be maintained and the protocol deviation recorded for possible exclusion at data lock.

Study restrictions: Participants will be required to comply with the following for the duration of the study:

Dietary Restrictions: Participants must agree to maintain their habitual intake of cruciferous vegetables for the duration of the study. Those who consume more than two portions of cruciferous vegetables per day will be excluded from participation. Participants must also be willing not to consume grapefruit or grapefruit juice for the duration of the study. Whilst at Surrey CRC for visit 4, participants must only consume foods and beverages that are provided.

Alcohol Restrictions: Participants must refrain from drinking alcohol for 48 hours prior to all study visits and will undergo an alcohol breath test to ensure compliance. Throughout the study participants should not consume more than 14 units of alcohol per week [NOTE: 1 unit is equivalent to approximately a half-pint (250 mL) of 4% beer or 1 (25 mL) measure of spirits or approximately half a glass (76 mL) of 13% wine].

Caffeine Restrictions: Participants must not consume more than 500 mg of caffeine (4-5 cups of strong coffee) per day for the duration of the study.

Prohibited medications and non-drug therapies: Participants are prohibited from taking medications (including food supplements and vitamins) during the course of the study (from screening onwards) except for oral contraceptives and the occasional use of paracetamol and ibuprofen, cold remedies and anti-histamines. If participants are prescribed any medications (including creams, ointments, inhalers) or if they purchase any medications 'over the counter' (OTC) (including herbal remedies), for example from the pharmacy, supermarket or health food shop, they must report the name of the drug(s)/herbal preparation(s), the dose, the dates, and the duration of treatment at their next visit, and reason for use, which will subsequently be recorded in the source document and CRF. Participants will be questioned at each assessment visit about the use of concomitant medication in the period since the last assessment visit. If a participant takes any of the above medications they will be withdrawn from the study. Any medication taken from screening and throughout the study period must be recorded on the source document and CRF with the name of the drug, dosage, date(s) of administration and reason for use.

Data analysis: Pharmacological parameters of plasma DIM concentrations ($AUC_{0-inf}$, $AUC_{0-t}$, $T_{max}$, and $C_{max}$, $C_{min}$, $K_{el}$, $t^{1/2}$, $T_{lag}$) will be compared between ACCUMAX SL group and ACCUMAX SL plus Quercetin group. Where required, parameters will be adjusted for time 0 where concentrations >0.

Duration of study period (per participant): 3 weeks plus screening period. Total number of scheduled visits 4.

Study Flow Chart:

| Procedures | Visit 1 Screening (Days −28-1) | Visit 2 Day 1 | Visit 3 Day 8 | Visit 4 (EOS) Day 21 |
|---|---|---|---|---|
| Written informed consent | X | | | |
| Demographic data | X | | | |
| Medical History | X | | | |
| Full Physical examination | X | | | X |
| Vital signs [a] | X | | | X |
| Assessment of inclusion/exclusion criteria | X | X | X | X |
| Height, Weight, BMI | X | | | |
| Concomitant medication | X | X | X | X |
| 12 Lead electrocardiogram (ECG) | X | | | |
| Laboratory safety [b] | X | | | |
| Urinalysis | X | | | |
| Alcohol breath test | X | X | X | X |
| Urine drug of abuse test | X | X | X | X |
| Urine cotinine | X | X | X | X |
| Urine pregnancy test [c] | X | X | X | X |
| Randomisation | | X | | |
| Product Returns | | | X | X |
| Accountability | | | | |
| Product (Quercetin) Dispensing: Group A only | | X | X | X[e] |
| Product (ACCUMAX SL) Dispensing: Groups A and B | | | X | X[e] |
| Dosing at the SCRC during visit | | X | X | X[e] |
| Adverse Events | | X | X | X |
| PK blood Sampling[d] | | | | X[e] |
| Dosing at home | | | Daily by Participants | |
| Dosing Diary | | | Daily by Participants | |

[a] Heart rate, blood pressure, oral temperature, respiratory rate
[b] Haematology, biochemistry, virology, urinalysis
[c] Female participants only
[d] PK timepoints –0 (pre-dose), 0.5 (+/−1 min), 1 (+/−1 min), 1.5 (+/−1 min), 2 (+/−1 min), 3 (+/−5 min), 4 (+/−5 min), 6 (+/−5 min), 9 (+/−5 min), 12 (+/−5 min) hours
[e] Not if EOS (End of Study) visit Study Data Parameters:
Pharmacokinetic Sampling Parameters
Sampling Times: Blood will be drawn at the following specified time points relative to dosing:
Pre-dose (0), 0.5 (+/−1 min), 1 (+/−1 min), 1.5 (+/−1 min), 2 (+/−1 min), 3 (+/−5 min), 4 (+/−5 min), 6 (+/−5 min), 9 (+/−5 min), 12 (+/−5 min) hours.
The total number of blood samples for pharmacokinetic analysis will be 10 for each participant.
The collection, handling and shipping requirements for these samples are described in separate study-specific documents.
Bioanalytic Methods: Plasma samples will be assayed for DIM concentrations by the analytical laboratory.
Blood Sample Volume: The blood volume for each PK sample will be 5 ml. Therefore a total of approximately 55 ml will be taken during Visit 4.
Safety parameters: Physical examinations, laboratory safety tests (blood chemistry, haematology, and urinalysis), vital sign measurements, and 12-lead ECGs will be performed at scheduled time points as per the study flow chart (see section 5.1). These procedures may also be performed at unscheduled time points if considered clinically necessary by the investigator. The detailed outline of the study procedures can be found in the study flowchart.
Vital Signs: Vital signs include: diastolic and systolic blood pressure measurement following five minutes in the supine position, heart rate, oral temperature and respiratory rate. They will be obtained at Visits 1 and 4.

ECG: A 12-lead ECG must be performed after resting for ~10 minutes in the supine position at the screening visit.

Clinical Laboratory Assessments: The following laboratory analyses will be taken at screening approximately 12 ml will be taken:

Haematology: haemoglobin, hematocrit, white blood cell count, red blood cell count and platelets Blood chemistry: alanine aminotransferase (ALT), albumin, alkaline phosphatase, aspartase aminotransferase (AST), blood urea nitrogen (BUN), calcium, chloride, creatinine, eGFR, lipids, magnesium, phosphorus, potassium, sodium, total bilirubin and total protein.

Virology: (Hepatitis B surface antigen, Hepatitis C antibody, HIV antibody).

Urinalysis will be performed by dipstick to evaluate protein, glucose, pH, ketones, specific gravity, bilirubin, nitrites, Leukocytes, Blood/Haemoglobin. Microscopy may be performed if the dipstick result is abnormal and deemed clinically significant.

If laboratory results are outside the reference range at screening and deemed NCS by the physicians then they do not need to be repeated, clinically significant results can be repeated once at the investigators discretion.

Safety monitoring: All participants will receive an information card indicating participation in the study with the name, address, and telephone number of a contact person at the study site for information in the event of an emergency.

Adverse Events (AEs): AEs will be collected from randomisation and for the 3-week duration of the study. Participants will be asked to document any AEs in their dosing diary whilst dosing at home. In addition, participants will be asked about any documented AEs and if they have any additional AEs when they attend for each study visit.

Specification of Safety Parameters:

Safety Assessment Abnormalities Reported as AEs and SAEs: Any abnormal safety assessments (e.g., vital signs measurements), including those that worsen from baseline, and felt to be clinically significant in the medical and scientific judgement of the investigator, are to be recorded as AEs or SAEs. However, any clinically significant safety assessments that are associated with the underlying disease, unless judged by the investigator to be more severe than expected for the participant's condition, are not to be reported as AEs or SAEs.

Pregnancy: Any pregnancy of a clinical study participant, or the partner of a clinical study participant must be reported in the same way as SAEs. Pregnancy complications and elective terminations for medical reasons must also be reported as an AE or SAE. Spontaneous abortions must be reported as an SAE. Any pregnancy that occurs during study participation must be reported using a clinical trial pregnancy form. To ensure participant safety, each pregnancy must be reported to the Sponsor within 24 hours. The Principal Investigator (PI) must assess whether the participant should be withdrawn from the study. The pregnancy must be followed up to determine outcome (including premature termination) and status of mother and child. Any SAE occurring in association with a pregnancy, brought to the investigator's attention after the participant has completed the study, and considered by the investigator as possibly related to the study product, must be promptly reported to the Sponsor.

Definition of an AE: Any untoward medical occurrence in a patient or clinical trial subject administered a medicinal product and which does not necessarily have a causal relationship with this treatment.

Note: An AE can therefore be any unfavourable and unintended sign (including an abnormal laboratory finding), symptom, or disease (new or exacerbated) temporally associated with the use of study products whether or not related to the study products.

Events meeting the definition of an AE include:

Exacerbation of a chronic or intermittent preexisting condition including either an increase in frequency and/or intensity of the condition New conditions detected or diagnosed after study product administration even though it may have been present prior to the start of the study Signs, symptoms, or the clinical sequelae of a suspected interaction Signs, symptoms, or the clinical sequelae of a suspected overdose of either study product or a concomitant medication (overdose per se will not be reported as an AE/SAE).

Events that do not meet the definition of an AE include:

Medical or surgical procedure (e.g. endoscopy, appendectomy); the condition that leads to the procedure is an AE.

Situations where an untoward medical occurrence did not occur (social and/or convenience admission to a hospital).

Anticipated day-to-day fluctuations of pre-existing disease(s) or condition(s) present or detected at the start of the study that do not worsen.

The disease/disorder being studied or expected progression, signs, or symptoms of the disease/disorder being studied, unless more severe than expected for the participant's condition.

Definition of a SAE: An SAE is any untoward medical occurrence that, at any dose:

Results in death: In general, death should not be reported as an event. Death is viewed as an outcome of an event, rather than an event itself. In cases where the cause of death is unknown, death may be reported as an event initially. However, every attempt must be made to submit a follow-up report identifying the probable cause of death when sufficient data are available. A death occurring during the study or which comes to the attention of the investigator within 4 weeks after stopping the study products, whether considered due to the study products or not, must be reported.

Is life-threatening: NOTE: The term 'life-threatening' in the definition of 'serious' refers to an event in which the participant was at risk of death at the time of the event. It does not refer to an event, which hypothetically might have caused death, if it were more severe.

Requires hospitalisation or prolongation of existing hospitalization: NOTE: In general, hospitalisation signifies that the participant has been detained (usually involving at least an overnight stay) at the hospital or emergency ward for observation and/or treatment that would not have been appropriate in the physician's office or out-patient setting. Complications that occur during hospitalisation are AEs. If a complication prolongs hospitalisation or fulfils any other serious criteria, the event is serious. When in doubt as to whether "hospitalisation" occurred or was necessary, the AE should be considered serious. Hospitalisation for elective treatment of a pre-existing condition that did not worsen from baseline is not considered an AE.

Results in persistent or significant disability/incapacity: NOTE: The term disability means a substantial disruption of a person's ability to conduct normal life functions. This definition is not intended to include experiences of relatively minor medical significance such as uncomplicated headache, nausea, vomiting, diarrhoea, influenza, or accidental trauma (e.g. sprained ankle) which may interfere or prevent everyday life functions but do not constitute a substantial disruption.

Is a congenital anomaly/birth defect.

Medical or scientific judgment must be exercised in deciding whether reporting is appropriate in other situations, such as important medical events that may not be immediately life-threatening or result in death or hospitalisation but may jeopardise the participant or may require medical or surgical intervention to prevent one or the other outcomes listed in the above definition. These should also be considered serious. Examples of such events are invasive or malignant cancers, intensive treatment in an emergency room or at home for allergic bronchospasm, blood dyscrasias or convulsions that do not result in hospitalisation, or development of drug dependency or drug abuse.

Evaluating and Recording AEs: The investigator or designee is responsible for detecting, documenting and reporting events that meet the definition of an AE or SAE. These must be recorded in the source AE form and/or CRF.

For all AEs, the following must be assessed and recorded on the AEs page of the CRF:
a) Description of AE
b) Start date and time
c) End date and time
d) Severity i.e. mild, moderate, severe (see below)
e) Relationship to study product(s)—completed by study physician
f) Action taken with study medication
g) Action/Treatment required, e.g. paracetamol
h) Outcome
i) Seriousness (see section on SAEs)

SAEs and AEs will be collected from the time that the first dose of study products is given until the follow up contact. However any SAEs assessed as related to study participation (e.g. products, protocol-mandated procedures, invasive tests, or change in existing therapy) will be recorded from the time a participant consents to participate in the study up to and including any follow-up contact. All SAEs will be reported to Sponsor within 24 hours.

Intensity of Event: The intensity of an AE is defined as follows:
Mild Transient symptoms, requiring no treatment, no interference with participant's daily activities, easily tolerated.
Moderate Marked symptoms, moderate interference with the participant's daily activities, usually ameliorated by simple therapeutic measures.
Severe Considerable interference with the participant's daily activities, requires intensive therapeutic intervention, incapacitating.

The term severe is a measure of intensity: thus a SAE is not necessarily serious. For example, nausea of several hours duration may be rated as severe, but may not be clinically serious.

Relationship to Study Products: The relationship of each AE to the study products must be recorded by a medically-qualified member of staff as one of the following scale:
Definitely Not related—The AE is judged to be clearly and incontrovertibly due only to extraneous causes (for example, disease, environment) definitely not associated with the test products being given and does not meet the criteria for any other drug relationship listed.
Probably Not related—In general, this category is applicable to an AE which meets the following criteria (it certainly must meet the first two criteria):
  1. It does not follow a reasonable temporal sequence from the product administration.
  2. It may readily have been produced by the participant's clinical state, environmental or toxic factors, or other modes of therapy administered to the participant.
  3. It does not follow a known pattern of response to the suspected product.
  4. It does not reappear or worsen when the product is re-administered.
Possibly Related—This category applies to those AEs in which the connection with the test products administration appears unlikely but cannot be ruled out with certainty. An AE may be considered as possibly product related if, or when:
  1. It follows a reasonable temporal sequence from administration of the product.
  2. It may have been produced by the participant's clinical state, environmental or toxic factors or other modes of therapy administered to the participant.
  3. It follows a known pattern of response to the suspected product.
Probably Related—This category applies to those AEs which are considered, with a high degree of certainty, to be related to the test products. An AE may be considered as probably product related if:
  1. It follows a reasonable temporal sequence from administration of the product.
  2. It cannot be reasonably explained by the known characteristics of the participant's clinical state, environmental or toxic factors, or other modes.
  3. It disappears or decreases on cessation or reduction in dose (there are important exceptions when an AE does not disappear upon discontinuation of the product, yet product-relatedness clearly exists).
  4. It follows a known pattern of response to the suspected product.

5. It reappears upon re-challenge.

Definitely Related—This category applies to those AEs which are considered to be definitely related to the test product. An AE may be considered as Definitely related if:
1. There is evidence of exposure to the test product.
2. It follows a reasonable temporal sequence from administration of the product.
3. It cannot be reasonably explained by the known characteristics of the participant's clinical state, environmental or toxic factors, or other modes.
4. The AE is more likely explained by the test product than by any other cause.
5. Dechallenge is positive.
6. Rechallenge (if feasible) is positive.
7. The AE shows a pattern consistent with previous knowledge of the test product or test product class.

Expectedness of SAEs: For this study, an adverse reaction is 'unexpected' if its nature and severity are not consistent with the information about the study products in question, set out in the IB. A medically-qualified member of staff must assign expectedness.

Prompt Reporting of SAEs, and Other Events to Sponsor: SAEs and pregnancies will be reported promptly to the Sponsor as described in the following table, once the investigator determines that the event meets the protocol definition for that event.

| Type of Event | Initial Reports | | Follow-up Information on a Previous Report | |
|---|---|---|---|---|
| | Time Frame | Documents | Time Frame | Documents |
| All SAEs | 24 hours | "SAE" form | 24 hours | Updated "SAE" form |
| Pregnancy | 24 hours | Pregnancy Notification Form | 24 hours | Pregnancy Follow-up Form |

SAEs which come to the attention of the investigator within 28 days of the first dose of the products, whether considered due to any of the study products or not, must be reported within the above timelines.

Treatment and Follow-up of AEs: All AEs must be documented and followed up until the event is either resolved or adequately explained, even after the participant has completed his/her trial treatment. In the case of any SAE, the participant must be followed up until clinical recovery is complete and laboratory results have returned to normal or until progression has been stabilised. This may mean that follow-up will continue after the participant has completed the clinical trial and that additional investigations may be requested by the Sponsor. SAEs that are spontaneously reported by a participant to the investigator after study completion and considered by the investigator to be caused by the study products with a reasonable possibility must be handled in the same manner as for SAEs reported during the study. In the event of unexplained clinically abnormal laboratory test values, the tests must be repeated immediately and followed up until the results have returned to within the range of normal and/or an adequate explanation of the abnormality is given. If a clear explanation is established, it must be recorded on the CRF.

Breaking the Double Blind Code: This is an open-label study and therefore this is not required.

Overdose of Study Products

Definition of an Overdose for this Protocol: An overdose is defined as whether the participant has taken, accidentally or intentionally, any study product administered as part of the protocol in excess of the dose prescribed by the protocol. The investigator or the reporting physician must assess the overdose incident as to whether it is an overdose with an AE or without an AE. All overdoses must be reported to the Sponsor.

Management of Overdose: Overdose of study product in the context of this clinical study may be managed with general symptomatic and supportive measures.

Analysis:

Primary endpoint: Relative bioavailability of the parameter $AUC_{inf}$ of DIM following ACCUMAX SL plus Quercetin compared to ACCUMAX SL alone.

Secondary end points: The mean values of the following parameters for the plasma DIM concentration time profile will be statistically compared between the two arms of the study $AUC_{0-t}$
$C_{max}$
$C_{min}$
$T_{max}$
$T_{lag}$
$K_{elim}$
$T_{1/2}$
Clearance In addition, the parameters AUC0-t, AUC0-inf and Cmax will be appropriately adjusted where the plasma concentration at time 0 is quantifiable to approximate single dosing.

Prior to locking the database a SAP will be prepared by the Trial Statistician which will be formally approved and signed off by the Trial Statistician, the Principal Investigator(s) and the Sponsor.

All participants who receive at least one dose of study product will be included in the safety analysis. No formal statistical analysis will be performed.

Example 6

Multiple Dose PK Study of a DIM+Vitamin a Taken with or without CYP450 Enzyme Modulator The parameters of this study are the same as disclosed in Example 5 above unless otherwise stated.

Study endpoints: Primary—Plasma levels of DIM following treatment with either one week's administration of CYP450 enzyme modulator (e.g. Quercetin) followed by 2 weeks' administration of CYP450 enzyme modulator and DIM+Vitamin A or no treatment for one week and then 2 weeks' administration of DIM+Vitamin A. In some instances, DIM+Vitamin A are administered orally. In some intances, DIM+Vitamin A are administered sublingually.

Study Products (Formulations, Route of Administration and Dose Regimen):

CYP450 enzyme modulator
  One single daily dose of about 100 mg to about 1000 mg given as an oral formulation
  Taken daily for 3 weeks (treatment group A) (Days 1-21)
  To be taken in the morning within 2 hours of waking and before food is consumed DIM+Vitamin A
  Oral or sublingual formulation
  Taken twice a day for 14 days (Days 8-21) in both groups A and B
  Tablets will be taken in the morning after an overnight fast of at least 8 hours and in the evening before going to bed (not with food)
  DIM dose of about 30 mg to about 200 mg per day
  Vitamin A dose of about 200 µg to about 2000 µg per day Data analysis: Pharmacological parameters of plasma DIM concentrations ($AUC_{0-inf}$, $AUC_{0-t}$, $T_{max}$, and $C_{max}$, $C_{min}$, $K_{el}$, $t^{1/2}$, $T_{lag}$) will be compared between DIM+Vitamin A group and DIM+Vitamin A plus CYP450 enzyme modulator group. Where required, parameters will be adjusted for time 0 where concentrations >0.

Additional Exemplary formulations of DIM:

Bioavailable DIM (BR-DIM): BioResponse-Diindolylmethane (Spray-Dried Diindolylmethane); BR-DIM. BR-DIM is composed of small, amorphous particles of pure DIM, phosphatidyl choline and vitamin E PEG Succinate, NF, which are embedded in larger particles (approximately 10-50 uM) composed of Acacia, NF and Malodextrin NF. Colloidal Silicon Dioxide NF, is also added at low concentrations as a process aid. BR-DIM is employed as a part-processed product, delivering a solubilized form of DIM that is then used in the manufacture of skin ACCUMAX™ SUBLINGUAL TABLET.

Exemplary Formulation of ACCUMAX SUBLINGUAL TABLET

| Raw Material Name | mg per tablet |
| --- | --- |
| BR-DIM | 150 (=35.8 mg DIM) |
| Vitamin A Palmitate | 400 µg Retinol Equivalents (188.2 µg Retinyl palmitate) |
| Excipients: | |
| Sorbitol BP | 363 |
| Mannitol PhEur. | 150 |
| Starch 1500 | 100 |
| Other ingredients <100 mg/tablet | |
| Tablet weight | 1,000 |

Exemplary Formulation of ACCUMAX CAPSULE

| Raw Material Name | mg per tablet |
| --- | --- |
| BR-DIM | 75 (=17.9 mg DIM) |
| Vitamin A Palmitate | 200 µg Retinol Equivalents (366.4 µg Retinyl palmitate) |
| Tri-calcium phosphate | 175 |
| Other ingredients <100 mg/tablet | |
| Tablet weight | 318 |

Exemplary Formularion of ACCUMAX SUBLINGUAL PLACEBO TABLET

| Raw Material Name | mg per tablet |
| --- | --- |
| Sorbitol BP 393 | 393 |
| Mannitol Ph. Eur. (200 mesh) | 250 |
| Mannitol (80%) maize starch (20%) | 106 |
| Maize starch 100 | |
| Other ingredients <100 mg/tablet | |
| Tablet weight | 1000 |

Certain Embodiments

Embodiment 1 provides a method of treating acne in a subject in need thereof comprising a combination therapy comprising administering a first composition comprising modulators of one or more CYP450 enzymes and a second composition comprising a substituted or unsubstituted diindolylmethane.

Embodiment 2 provides the method of embodiment 1, wherein the combination therapy further comprises administering a third composition comprising a substituted or unsubstituted retinoic acid based component.

Embodiment 3 provides the method of embodiment 2, wherein the retinoic acid based component is Vitamin A.

Embodiment 4 provides the method of any one of embodiments 1-3, wherein the Vitamin A is contained in the second composition comprising a substituted or unsubstituted diindolylmethane.

Embodiment 5 provides the method of any one of embodiments 1-4, wherein the first and the second compositions are administered by oral route.

Embodiment 6 provides the method of any one of embodiments 1-5, wherein one or more doses of the first composition comprising modulators of one or more CYP450 enzymes is administered prior to administering the second composition comprising a substituted or unsubstituted diindolylmethane.

Embodiment 7 provides the method of any one of embodiments 1-6, wherein the one or more doses of the first composition are administered from about 1 day to about 21 days prior to the administering the second composition.

Embodiment 8 provides the method of any one of embodiments 1-6, wherein the one or more doses of the first composition are administered from about 1 hour to about 30 hours prior to the administering the second composition.

Embodiment 9 provides the method of any one of embodiments 1-8, wherein a first dose of the first composition is administered about 24 hours prior to administering the second composition and a second dose of the first composition is administered about 12 hours prior to administering the second composition.

Embodiment 10 provides the method of any one of embodiments 1-5, wherein the first and the second compositions are administered concurrently.

Embodiment 11 provides the method of any one of embodiments 1-9, wherein the first composition is administered to modulate one or more CYP450 enzymes comprising CYP1A1, CYP1A2, CYP2D6, CYP2C8, CYP2C9, CYP3A4, CYP2C19, and CYP19A1.

Embodiment 12 provides the method of any one of embodiments 1-11, wherein the first composition comprises one or more of black raspberry, blueberry, ellagic acid, pomegranate, walnuts, blackcurrants, soy, soybean, black soybean, turmeric, apiaceous vegetable, cruciferous vegetables, allium vegetables, garden cress, watercress, yellow onion, kale, alfalfa sprouts, green beans, chili powder, daizein, garlic, apple, apricot, chamomile, peppermint, dandelion, green tea, black tea, rooibos tea, itadori tea, coffee, caffeine, caffeic acid, grapes, wine, peanuts, honey, medium-chain triglycerides, coconut and coconut oil, honeycomb, fish oil, rosemary, N-acetyl cysteine, chrysin, quercetin, resveratrol, myricetin, curcumin, curry powder, fish oil, rosemary, astaxanthin, algae, yeast, salmon, trout, krill, shrimp, crayfish, and chicory root.

Embodiment 13 provides the method of any one of embodiments 1-11, wherein the first composition is administered to inhibit one or more enzymes comprising CYP1A1, CYP1A2, CYP2D6, CYP2C8, CYP2C9, CYP3A4, CYP2C19, and CYP19A1.

Embodiment 14 provides the method of embodiment 13, wherein the first composition comprises one or more of black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, grapes, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin.

Embodiment 15 provides the method of embodiment 13, wherein the first composition comprises one or more of black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin.

Embodiment 16 provides the method of any one of embodiments 1-11, wherein the first composition is administered to induce one or more enzymes cytochrome P450 enzymes comprising CYP1A1, CYP1A2, CYP2D6, CYP2C8, CYP2C9, CYP2C19, and CYP19A1.

Embodiment 17 provides the method of embodiment 16, wherein the first composition comprises one or more of cruciferous vegetables, resveratrol, grapes, wine, peanuts, soy, itadori tea, green tea, black tea, curcumin, turmeric, curry powder, soybean, garlic, fish oil, rosemary, astaxanthin, algae, yeast, salmon, trout, krill, shrimp, crayfish, chicory root, quercertin, apple, apricot, blueberries, yellow onion, kale, alfalfa sprouts, green beans, broccoli, black tea, chili powder, and rooibos tea.

Embodiment 18 provides the method of any one of embodiments 1-17, wherein the combination therapy increases bioavailability of the substituted or unsubstituted diindolylmethane.

Embodiment 19 provides the method of embodiment 18, wherein the combination therapy increases the bioavailability of the substituted or unsubstituted diindolylmethane by from about 1-fold to about 1000-fold compared to a monotherapy with only the second composition.

Embodiment 20 provides the method of embodiment 18, wherein the combination therapy increases the bioavailability of the substituted or unsubstituted diindolylmethane by about 1-fold compared to a monotherapy with only the second composition.

Embodiment 21 provides the method of embodiment 18, wherein the combination therapy increases the bioavailability of the substituted or unsubstituted diindolylmethane by about 2-fold compared to a monotherapy with only the second composition.

Embodiment 22 provides the method of embodiment 18, wherein the combination therapy increases the bioavailability of the substituted or unsubstituted diindolylmethane by about 3-fold compared to a monotherapy with only the second composition.

Embodiment 23 provides the method of embodiment 18, wherein the combination therapy increases the bioavailability of the substituted or unsubstituted diindolylmethane by about 4-fold compared to a monotherapy with only the second composition.

Embodiment 24 provides the method of embodiment 18, wherein the combination therapy increases the bioavailability of the substituted or unsubstituted diindolylmethane by about 5-fold compared to a monotherapy with only the second composition.

Embodiment 25 provides the method of embodiment 18, wherein the combination therapy increases the bioavailability of the substituted or unsubstituted diindolylmethane by about 10-fold compared to a monotherapy with only the second composition.

Embodiment 26 provides the method of embodiment 18, wherein the combination therapy increases the bioavailability of the substituted or unsubstituted diindolylmethane by about 20-fold compared to a monotherapy with only the second composition.

Embodiment 27 provides the method of embodiment 18, wherein the combination therapy increases the bioavailability of the substituted or unsubstituted diindolylmethane by about 30-fold compared to a monotherapy with only the second composition.

Embodiment 28 provides the method of embodiment 18, wherein the combination therapy increases the bioavailability of the substituted or unsubstituted diindolylmethane by about 40-fold compared to a monotherapy with only the second composition.

Embodiment 29 provides the method of embodiment 18, wherein the combination therapy increases the bioavailability of the substituted or unsubstituted diindolylmethane by about 50-fold compared to a monotherapy with only the second composition.

Embodiment 30 provides the method of embodiment 18, wherein the combination therapy increases the bioavailability of the substituted or unsubstituted diindolylmethane by about 60-fold compared to a monotherapy with only the second composition.

Embodiment 31 provides the method of embodiment 18, wherein the combination therapy increases the bioavailability of the substituted or unsubstituted diindolylmethane by about 70-fold compared to a monotherapy with only the second composition.

Embodiment 32 provides the method of embodiment 18, wherein the combination therapy increases the bioavailability of the substituted or unsubstituted diindolylmethane by about 80-fold compared to a monotherapy with only the second composition.

Embodiment 33 provides the method of embodiment 18, wherein the combination therapy increases the bioavailability of the substituted or unsubstituted diindolylmethane by about 90-fold compared to a monotherapy with only the second composition.

Embodiment 34 provides the method of embodiment 18, wherein the combination therapy increases the bioavailability of the substituted or unsubstituted diindolylmethane by about 100-fold compared to a monotherapy with only the second composition.

Embodiment 35 provides the method of embodiment 18, wherein the combination therapy increases the bioavailability of the substituted or unsubstituted diindolylmethane by about 200-fold compared to a monotherapy with only the second composition.

Embodiment 36 provides the method of embodiment 18, wherein the combination therapy increases the bioavailability of the substituted or unsubstituted diindolylmethane by about 300-fold compared to a monotherapy with only the second composition.

Embodiment 37 provides the method of embodiment 18, wherein the combination therapy increases the bioavailability of the substituted or unsubstituted diindolylmethane by about 400-fold compared to a monotherapy with only the second composition.

Embodiment 38 provides the method of embodiment 18, wherein the combination therapy increases the bioavailability of the substituted or unsubstituted diindolylmethane by about 500-fold compared to a monotherapy with only the second composition.

Embodiment 39 provides the method of embodiment 18, wherein the combination therapy increases the bioavailability of the substituted or unsubstituted diindolylmethane by about 600-fold compared to a monotherapy with only the second composition.

Embodiment 40 provides the method of embodiment 18, wherein the combination therapy increases the bioavailability of the substituted or unsubstituted diindolylmethane by about 700-fold compared to a monotherapy with only the second composition.

Embodiment 41 provides the method of embodiment 18, wherein the combination therapy increases the bioavailability of the substituted or unsubstituted diindolylmethane by about 800-fold compared to a monotherapy with only the second composition.

Embodiment 42 provides the method of embodiment 18, wherein the combination therapy increases the bioavailability of the substituted or unsubstituted diindolylmethane by about 900-fold compared to a monotherapy with only the second composition.

Embodiment 43 provides the method of embodiment 18, wherein the combination therapy increases the bioavailability of the substituted or unsubstituted diindolylmethane by about 1000-fold compared to a monotherapy with only the second composition.

Embodiment 44 provides the method of any one of embodiments 18-43, wherein the second composition is administered at a dosage comprising at least 15 mg of the substituted or unsubstituted diindolylmethane.

Embodiment 45 provides the method of any one of embodiments 1-44, wherein the combination therapy increases Cmax of the substituted or unsubstituted diindolylmethane in plasma.

Embodiment 46 provides the method of embodiment 45, wherein the combination therapy increases the Cmax of the substituted or unsubstituted diindolylmethane in plasma by from about 1-fold to about 1000-fold compared to a monotherapy with only the first composition.

Embodiment 47 provides the method of embodiment 45, wherein the combination therapy increases the Cmax of the substituted or unsubstituted diindolylmethane by about 1-fold compared to a monotherapy with only the second composition.

Embodiment 48 provides the method of embodiment 45, wherein the combination therapy increases the Cmax of the substituted or unsubstituted diindolylmethane by about 2-fold compared to a monotherapy with only the second composition.

Embodiment 49 provides the method of embodiment 45, wherein the combination therapy increases the Cmax of the substituted or unsubstituted diindolylmethane by about 3-fold compared to a monotherapy with only the second composition.

Embodiment 50 provides the method of embodiment 45, wherein the combination therapy increases the Cmax of the substituted or unsubstituted diindolylmethane by about 4-fold compared to a monotherapy with only the second composition.

Embodiment 51 provides the method of embodiment 45, wherein the combination therapy increases the Cmax of the substituted or unsubstituted diindolylmethane by about 5-fold compared to a monotherapy with only the second composition.

Embodiment 52 provides the method of embodiment 45, wherein the combination therapy increases the Cmax of the substituted or unsubstituted diindolylmethane by about 10-fold compared to a monotherapy with only the second composition.

Embodiment 53 provides the method of embodiment 45, wherein the combination therapy increases the Cmax of the substituted or unsubstituted diindolylmethane by about 20-fold compared to a monotherapy with only the second composition.

Embodiment 54 provides the method of embodiment 45, wherein the combination therapy increases the Cmax of the substituted or unsubstituted diindolylmethane by about 30-fold compared to a monotherapy with only the second composition.

Embodiment 55 provides the method of embodiment 45, wherein the combination therapy increases the Cmax of the substituted or unsubstituted diindolylmethane by about 40-fold compared to a monotherapy with only the second composition.

Embodiment 56 provides the method of embodiment 45, wherein the combination therapy increases the Cmax of the substituted or unsubstituted diindolylmethane by about 50-fold compared to a monotherapy with only the second composition.

Embodiment 57 provides the method of embodiment 45, wherein the combination therapy increases the Cmax of the substituted or unsubstituted diindolylmethane by about 60-fold compared to a monotherapy with only the second composition.

Embodiment 58 provides the method of embodiment 45, wherein the combination therapy increases the Cmax of the substituted or unsubstituted diindolylmethane by about 70-fold compared to a monotherapy with only the second composition.

Embodiment 59 provides the method of embodiment 45, wherein the combination therapy increases the Cmax of the substituted or unsubstituted diindolylmethane by about 80-fold compared to a monotherapy with only the second composition.

Embodiment 60 provides the method of embodiment 45, wherein the combination therapy increases the Cmax of the substituted or unsubstituted diindolylmethane by about 90-fold compared to a monotherapy with only the second composition.

Embodiment 61 provides the method of embodiment 45, wherein the combination therapy increases the Cmax of the substituted or unsubstituted diindolylmethane by about 100-fold compared to a monotherapy with only the second composition.

Embodiment 62 provides the method of embodiment 45, wherein the combination therapy increases the Cmax of the substituted or unsubstituted diindolylmethane by about 200-fold compared to a monotherapy with only the second composition.

Embodiment 63 provides the method of embodiment 45, wherein the combination therapy increases the Cmax of the substituted or unsubstituted diindolylmethane by about 300-fold compared to a monotherapy with only the second composition.

Embodiment 64 provides the method of embodiment 45, wherein the combination therapy increases the Cmax of the substituted or unsubstituted diindolylmethane by about 400-fold compared to a monotherapy with only the second composition.

Embodiment 65 provides the method of embodiment 45, wherein the combination therapy increases the Cmax of the substituted or unsubstituted diindolylmethane by about 500-fold compared to a monotherapy with only the second composition.

Embodiment 66 provides the method of embodiment 45, wherein the combination therapy increases the Cmax of the substituted or unsubstituted diindolylmethane by about 600-fold compared to a monotherapy with only the second composition.

Embodiment 67 provides the method of embodiment 45, wherein the combination therapy increases the Cmax of the substituted or unsubstituted diindolylmethane by about 700-fold compared to a monotherapy with only the second composition.

Embodiment 68 provides the method of embodiment 45, wherein the combination therapy increases the Cmax of the substituted or unsubstituted diindolylmethane by about 800-fold compared to a monotherapy with only the second composition.

Embodiment 69 provides the method of embodiment 45, wherein the combination therapy increases the Cmax of the substituted or unsubstituted diindolylmethane by about 900-fold compared to a monotherapy with only the second composition.

Embodiment 70 provides the method of embodiment 45, wherein the combination therapy increases the Cmax of the substituted or unsubstituted diindolylmethane by about 1000-fold compared to a monotherapy with only the second composition.

Embodiment 71 provides the method of any one of embodiments 45-70, wherein the second composition is administered at a dosage comprising at least 15 mg of the substituted or unsubstituted diindolylmethane.

Embodiment 72 provides the method of any one of embodiments 1-71, wherein the combination therapy increases AUC of the substituted or unsubstituted diindolylmethane in plasma.

Embodiment 73 provides the method of embodiment 72, wherein the combination therapy increases the AUC of the substituted or unsubstituted diindolylmethane in plasma by from about 1-fold to about 1000-fold compared to a monotherapy with only the second composition.

Embodiment 74 provides the method of embodiment 72, wherein the combination therapy increases the AUC of the substituted or unsubstituted diindolylmethane by about 1-fold compared to a monotherapy with only the second composition.

Embodiment 75 provides the method of embodiment 72, wherein the combination therapy increases the AUC of the substituted or unsubstituted diindolylmethane by about 2-fold compared to a monotherapy with only the second composition.

Embodiment 76 provides the method of embodiment 72, wherein the combination therapy increases the AUC of the substituted or unsubstituted diindolylmethane by about 3-fold compared to a monotherapy with only the second composition.

Embodiment 77 provides the method of embodiment 72, wherein the combination therapy increases the AUC of the substituted or unsubstituted diindolylmethane by about 4-fold compared to a monotherapy with only the second composition.

Embodiment 78 provides the method of embodiment 72, wherein the combination therapy increases the AUC of the substituted or unsubstituted diindolylmethane by about 5-fold compared to a monotherapy with only the second composition.

Embodiment 79 provides the method of embodiment 72, wherein the combination therapy increases the AUC of the substituted or unsubstituted diindolylmethane by about 10-fold compared to a monotherapy with only the second composition.

Embodiment 80 provides the method of embodiment 72, wherein the combination therapy increases the AUC of the substituted or unsubstituted diindolylmethane by about 20-fold compared to a monotherapy with only the second composition.

Embodiment 81 provides the method of embodiment 72, wherein the combination therapy increases the AUC of the substituted or unsubstituted diindolylmethane by about 30-fold compared to a monotherapy with only the second composition.

Embodiment 82 provides the method of embodiment 72, wherein the combination therapy increases the AUC of the substituted or unsubstituted diindolylmethane by about 40-fold compared to a monotherapy with only the second composition.

Embodiment 83 provides the method of embodiment 72, wherein the combination therapy increases the AUC of the substituted or unsubstituted diindolylmethane by about 50-fold compared to a monotherapy with only the second composition.

Embodiment 84 provides the method of embodiment 72, wherein the combination therapy increases the AUC of the substituted or unsubstituted diindolylmethane by about 60-fold compared to a monotherapy with only the second composition.

Embodiment 85 provides the method of embodiment 72, wherein the combination therapy increases the AUC of the substituted or unsubstituted diindolylmethane by about 70-fold compared to a monotherapy with only the second composition.

Embodiment 86 provides the method of embodiment 72, wherein the combination therapy increases the AUC of the substituted or unsubstituted diindolylmethane by about 80-fold compared to a monotherapy with only the second composition.

Embodiment 87 provides the method of embodiment 72, wherein the combination therapy increases the AUC of the substituted or unsubstituted diindolylmethane by about 90-fold compared to a monotherapy with only the second composition.

Embodiment 88 provides the method of embodiment 72, wherein the combination therapy increases the AUC of the substituted or unsubstituted diindolylmethane by about 100-fold compared to a monotherapy with only the second composition.

Embodiment 89 provides the method of embodiment 72, wherein the combination therapy increases the AUC of the substituted or unsubstituted diindolylmethane by about 200-fold compared to a monotherapy with only the second composition.

Embodiment 90 provides the method of embodiment 72, wherein the combination therapy increases the AUC of the substituted or unsubstituted diindolylmethane by about 300-fold compared to a monotherapy with only the second composition.

Embodiment 91 provides the method of embodiment 72, wherein the combination therapy increases the AUC of the substituted or unsubstituted diindolylmethane by about 400-fold compared to a monotherapy with only the second composition.

Embodiment 92 provides the method of embodiment 72, wherein the combination therapy increases the AUC of the substituted or unsubstituted diindolylmethane by about 500-fold compared to a monotherapy with only the second composition.

Embodiment 93 provides the method of embodiment 72, wherein the combination therapy increases the AUC of the substituted or unsubstituted diindolylmethane by about 600-fold compared to a monotherapy with only the second composition.

Embodiment 94 provides the method of embodiment 72, wherein the combination therapy increases the AUC of the substituted or unsubstituted diindolylmethane by about 700-fold compared to a monotherapy with only the second composition.

Embodiment 95 provides the method of embodiment 72, wherein the combination therapy increases the AUC of the substituted or unsubstituted diindolylmethane by about 800-fold compared to a monotherapy with only the second composition.

Embodiment 96 provides the method of embodiment 72, wherein the combination therapy increases the AUC of the substituted or unsubstituted diindolylmethane by about 900-fold compared to a monotherapy with only the second composition.

Embodiment 97 provides the method of embodiment 72, wherein the combination therapy increases the AUC of the substituted or unsubstituted diindolylmethane by about 1000-fold compared to a monotherapy with only the second composition.

Embodiment 98 provides the method of any one of embodiments 72-97, wherein the second composition is administered at a dosage comprising at least 15 mg of the substituted or unsubstituted diindolylmethane.

Embodiment 99 provides the method of any one of embodiments 1-98, wherein the combination therapy decreases Tmax of the substituted or unsubstituted diindolylmethane in plasma.

Embodiment 100 provides the method of embodiment 99, wherein the combination therapy decreases the Tmax of the substituted or unsubstituted diindolylmethane in plasma by from about 1-fold to about 1000-fold compared to a monotherapy with only the second composition.

Embodiment 101 provides the method of embodiment 99, wherein the combination therapy decreases the Tmax of the substituted or unsubstituted diindolylmethane by about 1-fold compared to a monotherapy with only the second composition.

Embodiment 102 provides the method of embodiment 99, wherein the combination therapy decreases the Tmax of the substituted or unsubstituted diindolylmethane by about 2-fold compared to a monotherapy with only the second composition.

Embodiment 103 provides the method of embodiment 99, wherein the combination therapy decreases the Tmax of the substituted or unsubstituted diindolylmethane by about 3-fold compared to a monotherapy with only the second composition.

Embodiment 104 provides the method of embodiment 99, wherein the combination therapy decreases the Tmax of the substituted or unsubstituted diindolylmethane by about 4-fold compared to a monotherapy with only the second composition.

Embodiment 105 provides the method of embodiment 99, wherein the combination therapy decreases the Tmax of the substituted or unsubstituted diindolylmethane by about 5-fold compared to a monotherapy with only the second composition.

Embodiment 106 provides the method of embodiment 99, wherein the combination therapy decreases the Tmax of the substituted or unsubstituted diindolylmethane by about 10-fold compared to a monotherapy with only the second composition.

Embodiment 107 provides the method of embodiment 99, wherein the combination therapy decreases the Tmax of the substituted or unsubstituted diindolylmethane by about 20-fold compared to a monotherapy with only the second composition.

Embodiment 108 provides the method of embodiment 99, wherein the combination therapy decreases the Tmax of the substituted or unsubstituted diindolylmethane by about 30-fold compared to a monotherapy with only the second composition.

Embodiment 109 provides the method of embodiment 99, wherein the combination therapy decreases the Tmax of the substituted or unsubstituted diindolylmethane by about 40-fold compared to a monotherapy with only the second composition.

Embodiment 110 provides the method of embodiment 99, wherein the combination therapy decreases the Tmax of the substituted or unsubstituted diindolylmethane by about 50-fold compared to a monotherapy with only the second composition.

Embodiment 111 provides the method of embodiment 99, wherein the combination therapy decreases the Tmax of the substituted or unsubstituted diindolylmethane by about 60-fold compared to a monotherapy with only the second composition.

Embodiment 112 provides the method of embodiment 99, wherein the combination therapy decreases the Tmax of the substituted or unsubstituted diindolylmethane by about 70-fold compared to a monotherapy with only the second composition.

Embodiment 113 provides the method of embodiment 99, wherein the combination therapy decreases the Tmax of the substituted or unsubstituted diindolylmethane by about 80-fold compared to a monotherapy with only the second composition.

Embodiment 114 provides the method of embodiment 99, wherein the combination therapy decreases the Tmax of the substituted or unsubstituted diindolylmethane by about 90-fold compared to a monotherapy with only the second composition.

Embodiment 115 provides the method of embodiment 99, wherein the combination therapy decreases the Tmax of the substituted or unsubstituted diindolylmethane by about 100-fold compared to a monotherapy with only the second composition.

Embodiment 116 provides the method of embodiment 99, wherein the combination therapy decreases the Tmax of the substituted or unsubstituted diindolylmethane by about 200-fold compared to a monotherapy with only the second composition.

Embodiment 117 provides the method of embodiment 99, wherein the combination therapy decreases the Tmax of the substituted or unsubstituted diindolylmethane by about 300-fold compared to a monotherapy with only the second composition.

Embodiment 118 provides the method of embodiment 99, wherein the combination therapy decreases the Tmax of the substituted or unsubstituted diindolylmethane by about 400-fold compared to a monotherapy with only the second composition.

Embodiment 119 provides the method of embodiment 99, wherein the combination therapy decreases the Tmax of the substituted or unsubstituted diindolylmethane by about 500-fold compared to a monotherapy with only the second composition.

Embodiment 120 provides the method of embodiment 99, wherein the combination therapy decreases the Tmax of the substituted or unsubstituted diindolylmethane by about 600-fold compared to a monotherapy with only the second composition.

Embodiment 121 provides the method of embodiment 99, wherein the combination therapy decreases the Tmax of the substituted or unsubstituted diindolylmethane by about 700-fold compared to a monotherapy with only the second composition.

Embodiment 122 provides the method of embodiment 99, wherein the combination therapy decreases the Tmax of the substituted or unsubstituted diindolylmethane by about 800-fold compared to a monotherapy with only the second composition.

Embodiment 123 provides the method of embodiment 99, wherein the combination therapy decreases the Tmax of the substituted or unsubstituted diindolylmethane by about 900-fold compared to a monotherapy with only the second composition.

Embodiment 124 provides the method of embodiment 99, wherein the combination therapy decreases the Tmax of the substituted or unsubstituted diindolylmethane by about 1000-fold compared to a monotherapy with only the second composition.

Embodiment 125 provides the method of any one of embodiments 99-124, wherein the second composition is administered at a dosage comprising at least 15 mg of the substituted or unsubstituted diindolylmethane.

Embodiment 126 provides the method of any one of embodiments 1-125, wherein the percentage of substituted or unsubstituted diindolylmethane effluxed by P-gp following the combination therapy is about 0.1% to about 50% of the percentage of substituted or unsubstituted diindolylmethane effluxed by P-gp following a monotherapy with only the first composition.

Embodiment 127 provides the method of embodiment 126, wherein the percentage of substituted or unsubstituted diindolylmethane effluxed by P-gp following the combination therapy is about 0.1% of the percentage of substituted or unsubstituted diindolylmethane effluxed by P-gp following a monotherapy with only the second composition.

Embodiment 128 provides the method of embodiment 126, wherein the percentage of substituted or unsubstituted diindolylmethane effluxed by P-gp following the combination therapy is about 0.2% of the percentage of substituted or unsubstituted diindolylmethane effluxed by P-gp following a monotherapy with only the second composition.

Embodiment 129 provides the method of embodiment 126, wherein the percentage of substituted or unsubstituted diindolylmethane effluxed by P-gp following the combination therapy is about 0.3% of the percentage of substituted or unsubstituted diindolylmethane effluxed by P-gp following a monotherapy with only the second composition.

Embodiment 130 provides the method of embodiment 126, wherein the percentage of substituted or unsubstituted diindolylmethane effluxed by P-gp following the combination therapy is about 0.4% of the percentage of substituted or unsubstituted diindolylmethane effluxed by P-gp following a monotherapy with only the second composition.

Embodiment 131 provides the method of embodiment 126, wherein the percentage of substituted or unsubstituted diindolylmethane effluxed by P-gp following the combination therapy is about 0.5% of the percentage of substituted or unsubstituted diindolylmethane effluxed by P-gp following a monotherapy with only the second composition.

Embodiment 132 provides the method of embodiment 126, wherein the percentage of substituted or unsubstituted diindolylmethane effluxed by P-gp following the combination therapy is about 0.6% of the percentage of substituted or unsubstituted diindolylmethane effluxed by P-gp following a monotherapy with only the second composition.

Embodiment 133 provides the method of embodiment 126, wherein the percentage of substituted or unsubstituted diindolylmethane effluxed by P-gp following the combination therapy is about 0.7% of the percentage of substituted or unsubstituted diindolylmethane effluxed by P-gp following a monotherapy with only the second composition.

Embodiment 134 provides the method of embodiment 126, wherein the percentage of substituted or unsubstituted diindolylmethane effluxed by P-gp following the combination therapy is about 0.8% of the percentage of substituted or unsubstituted diindolylmethane effluxed by P-gp following a monotherapy with only the second composition.

Embodiment 135 provides the method of embodiment 126, wherein the percentage of substituted or unsubstituted diindolylmethane effluxed by P-gp following the combination therapy is about 0.9% of the percentage of substituted or unsubstituted diindolylmethane effluxed by P-gp following a monotherapy with only the second composition.

Embodiment 136 provides the method of embodiment 126, wherein the percentage of substituted or unsubstituted diindolylmethane effluxed by P-gp following the combination therapy is about 1% of the percentage of substituted or unsubstituted diindolylmethane effluxed by P-gp following a monotherapy with only the second composition.

Embodiment 137 provides the method of embodiment 126, wherein the percentage of substituted or unsubstituted diindolylmethane effluxed by P-gp following the combination therapy is about 2% of the percentage of substituted or unsubstituted diindolylmethane effluxed by P-gp following a monotherapy with only the second composition.

Embodiment 138 provides the method of embodiment 126, wherein the percentage of substituted or unsubstituted diindolylmethane effluxed by P-gp following the combination therapy is about 3% of the percentage of substituted or unsubstituted diindolylmethane effluxed by P-gp following a monotherapy with only the second composition.

Embodiment 139 provides the method of embodiment 126, wherein the percentage of substituted or unsubstituted diindolylmethane effluxed by P-gp following the combination therapy is about 4% of the percentage of substituted or unsubstituted diindolylmethane effluxed by P-gp following a monotherapy with only the second composition.

Embodiment 140 provides the method of embodiment 126, wherein the percentage of substituted or unsubstituted diindolylmethane effluxed by P-gp following the combination therapy is about 5% of the percentage of substituted or unsubstituted diindolylmethane effluxed by P-gp following a monotherapy with only the second composition.

Embodiment 141 provides the method of embodiment 126, wherein the percentage of substituted or unsubstituted diindolylmethane effluxed by P-gp following the combination therapy is about 6% of the percentage of substituted or unsubstituted diindolylmethane effluxed by P-gp following a monotherapy with only the second composition.

Embodiment 142 provides the method of embodiment 126, wherein the percentage of substituted or unsubstituted diindolylmethane effluxed by P-gp following the combination therapy is about 7% of the percentage of substituted or unsubstituted diindolylmethane effluxed by P-gp following a monotherapy with only the second composition.

Embodiment 143 provides the method of embodiment 126, wherein the percentage of substituted or unsubstituted diindolylmethane effluxed by P-gp following the combination therapy is about 8% of the percentage of substituted or unsubstituted diindolylmethane effluxed by P-gp following a monotherapy with only the second composition.

Embodiment 144 provides the method of embodiment 126, wherein the percentage of substituted or unsubstituted diindolylmethane effluxed by P-gp following the combination therapy is about 9% of the percentage of substituted or unsubstituted diindolylmethane effluxed by P-gp following a monotherapy with only the second composition.

Embodiment 145 provides the method of embodiment 126, wherein the percentage of substituted or unsubstituted diindolylmethane effluxed by P-gp following the combination therapy is about 10% of the percentage of substituted or unsubstituted diindolylmethane effluxed by P-gp following a monotherapy with only the second composition.

Embodiment 146 provides the method of embodiment 126, wherein the percentage of substituted or unsubstituted diindolylmethane effluxed by P-gp following the combination therapy is about 20% of the percentage of substituted or unsubstituted diindolylmethane effluxed by P-gp following a monotherapy with only the second composition.

Embodiment 147 provides the method of embodiment 126, wherein the percentage of substituted or unsubstituted diindolylmethane effluxed by P-gp following the combination therapy is about 30% of the percentage of substituted or unsubstituted diindolylmethane effluxed by P-gp following a monotherapy with only the second composition.

Embodiment 148 provides the method of embodiment 126, wherein the percentage of substituted or unsubstituted diindolylmethane effluxed by P-gp following the combination therapy is about 40% of the percentage of substituted or unsubstituted diindolylmethane effluxed by P-gp following a monotherapy with only the second composition.

Embodiment 149 provides the method of embodiment 126, wherein the percentage of substituted or unsubstituted diindolylmethane effluxed by P-gp following the combination therapy is about 50% of the percentage of substituted or unsubstituted diindolylmethane effluxed by P-gp following a monotherapy with only the second composition.

Embodiment 150 provides the method of any one of embodiments 126-149, wherein the second composition is administered at a dosage comprising at least 15 mg of the substituted or unsubstituted diindolylmethane.

Embodiment 151 provides the method of any one of embodiments 1-150, wherein the percentage of substituted or unsubstituted diindolylmethane metabolized by CYP450 enzymes following the combination therapy is from about 0.1% to about 50% of the percentage of substituted or unsubstituted diindolylmethane metabolized by CYP450 enzymes following a monotherapy with only the second composition.

Embodiment 152 provides the method of embodiment 151, wherein the percentage of substituted or unsubstituted diindolylmethane metabolized by CYP450 enzymes following the combination therapy is about 0.1% of the percentage of substituted or unsubstituted diindolylmethane metabolized by CYP450 enzymes following a monotherapy with only the second composition.

Embodiment 153 provides the method of embodiment 151, wherein the percentage of substituted or unsubstituted diindolylmethane metabolized by CYP450 enzymes following the combination therapy is about 0.2% of the percentage of substituted or unsubstituted diindolylmethane metabolized by CYP450 enzymes following a monotherapy with only the second composition.

Embodiment 154 provides the method of embodiment 151, wherein the percentage of substituted or unsubstituted diindolylmethane metabolized by CYP450 enzymes following the combination therapy is about 0.3% of the percentage of substituted or unsubstituted diindolylmethane metabolized by CYP450 enzymes following a monotherapy with only the second composition.

Embodiment 155 provides the method of embodiment 151, wherein the percentage of substituted or unsubstituted diindolylmethane metabolized by CYP450 enzymes following the combination therapy is about 0.4% of the percentage of substituted or unsubstituted diindolylmethane metabolized by CYP450 enzymes following a monotherapy with only the second composition.

Embodiment 156 provides the method of embodiment 151, wherein the percentage of substituted or unsubstituted diindolylmethane metabolized by CYP450 enzymes following the combination therapy is about 0.5% of the percentage of substituted or unsubstituted diindolylmethane metabolized by CYP450 enzymes following a monotherapy with only the second composition.

Embodiment 157 provides the method of embodiment 151, wherein the percentage of substituted or unsubstituted diindolylmethane metabolized by CYP450 enzymes following the combination therapy is about 0.6% of the percentage of substituted or unsubstituted diindolylmethane metabolized by CYP450 enzymes following a monotherapy with only the second composition.

Embodiment 158 provides the method of embodiment 151, wherein the percentage of substituted or unsubstituted diindolylmethane metabolized by CYP450 enzymes following the combination therapy is about 0.7% of the percentage of substituted or unsubstituted diindolylmethane metabolized by CYP450 enzymes following a monotherapy with only the second composition.

Embodiment 159 provides the method of embodiment 151, wherein the percentage of substituted or unsubstituted diindolylmethane metabolized by CYP450 enzymes following the combination therapy is about 0.8% of the percentage of substituted or unsubstituted diindolylmethane metabolized by CYP450 enzymes following a monotherapy with only the second composition.

Embodiment 160 provides the method of embodiment 151, wherein the percentage of substituted or unsubstituted diindolylmethane metabolized by CYP450 enzymes following the combination therapy is about 0.9% of the percentage of substituted or unsubstituted diindolylmethane metabolized by CYP450 enzymes following a monotherapy with only the second composition.

Embodiment 161 provides the method of embodiment 151, wherein the percentage of substituted or unsubstituted diindolylmethane metabolized by CYP450 enzymes following the combination therapy is about 1% of the percentage of substituted or unsubstituted diindolylmethane metabolized by CYP450 enzymes following a monotherapy with only the second composition.

Embodiment 162 provides the method of embodiment 151, wherein the percentage of substituted or unsubstituted diindolylmethane metabolized by CYP450 enzymes following the combination therapy is about 2% of the percentage of substituted or unsubstituted diindolylmethane metabolized by CYP450 enzymes following a monotherapy with only the second composition.

Embodiment 163 provides the method of embodiment 151, wherein the percentage of substituted or unsubstituted diindolylmethane metabolized by CYP450 enzymes following the combination therapy is about 3% of the percentage of substituted or unsubstituted diindolylmethane metabolized by CYP450 enzymes following a monotherapy with only the second composition.

Embodiment 164 provides the method of embodiment 151, wherein the percentage of substituted or unsubstituted diindolylmethane metabolized by CYP450 enzymes following the combination therapy is about 4% of the percentage of substituted or unsubstituted diindolylmethane metabolized by CYP450 enzymes following a monotherapy with only the second composition.

Embodiment 165 provides the method of embodiment 151, wherein the percentage of substituted or unsubstituted diindolylmethane metabolized by CYP450 enzymes following the combination therapy is about 5% of the percentage of substituted or unsubstituted diindolylmethane metabolized by CYP450 enzymes following a monotherapy with only the second composition.

Embodiment 166 provides the method of embodiment 151, wherein the percentage of substituted or unsubstituted diindolylmethane metabolized by CYP450 enzymes following the combination therapy is about 6% of the percentage of substituted or unsubstituted diindolylmethane metabolized by CYP450 enzymes following a monotherapy with only the second composition.

Embodiment 167 provides the method of embodiment 151, wherein the percentage of substituted or unsubstituted diindolylmethane metabolized by CYP450 enzymes following the combination therapy is about 7% of the percentage of substituted or unsubstituted diindolylmethane metabolized by CYP450 enzymes following a monotherapy with only the second composition.

Embodiment 168 provides the method of embodiment 151, wherein the percentage of substituted or unsubstituted diindolylmethane metabolized by CYP450 enzymes following the combination therapy is about 8% of the percentage of substituted or unsubstituted diindolylmethane metabolized by CYP450 enzymes following a monotherapy with only the second composition.

Embodiment 169 provides the method of embodiment 151, wherein the percentage of substituted or unsubstituted diindolylmethane metabolized by CYP450 enzymes following the combination therapy is about 9% of the percentage of substituted or unsubstituted diindolylmethane metabolized by CYP450 enzymes following a monotherapy with only the second composition.

Embodiment 170 provides the method of embodiment 151, wherein the percentage of substituted or unsubstituted diindolylmethane metabolized by CYP450 enzymes following the combination therapy is about 10% of the percentage of substituted or unsubstituted diindolylmethane metabolized by CYP450 enzymes following a monotherapy with only the second composition.

Embodiment 171 provides the method of embodiment 151, wherein the percentage of substituted or unsubstituted diindolylmethane metabolized by CYP450 enzymes following the combination therapy is about 20% of the percentage of substituted or unsubstituted diindolylmethane metabolized by CYP450 enzymes following a monotherapy with only the second composition.

Embodiment 172 provides the method of embodiment 151, wherein the percentage of substituted or unsubstituted diindolylmethane metabolized by CYP450 enzymes following the combination therapy is about 30% of the percentage of substituted or unsubstituted diindolylmethane metabolized by CYP450 enzymes following a monotherapy with only the second composition.

Embodiment 173 provides the method of embodiment 151, wherein the percentage of substituted or unsubstituted diindolylmethane metabolized by CYP450 enzymes following the combination therapy is about 40% of the percentage of substituted or unsubstituted diindolylmethane metabolized by CYP450 enzymes following a monotherapy with only the second composition.

Embodiment 174 provides the method of embodiment 151, wherein the percentage of substituted or unsubstituted diindolylmethane metabolized by CYP450 enzymes following the combination therapy is about 50% of the percentage of substituted or unsubstituted diindolylmethane metabolized by CYP450 enzymes following a monotherapy with only the second composition.

Embodiment 175 provides the method of any one of embodiments 151-174, wherein the second composition is administered at a dosage comprising at least 15 mg of the substituted or unsubstituted diindolylmethane.

Embodiment 176 provides the method of any one of embodiments 1-175, wherein the percentage of a composition influxed by an OATP following the combination therapy is from about 0.1% to about 50% of the percentage of substituted or unsubstituted diindolylmethane influxed by an OATP following a monotherapy with only the second composition.

Embodiment 177 provides the method of embodiment 176, wherein the percentage of a composition influxed by an OATP following the combination therapy is about 0.2% of the percentage of substituted or unsubstituted diindolylmethane influxed by an OATP following a monotherapy with only the second composition.

Embodiment 178 provides the method of embodiment 176, wherein the percentage of a composition influxed by an OATP following the combination therapy is about 0.3% of the percentage of substituted or unsubstituted diindolylmethane influxed by an OATP following a monotherapy with only the second composition.

Embodiment 179 provides the method of embodiment 176, wherein the percentage of a composition influxed by an OATP following the combination therapy is about 0.4% of the percentage of substituted or unsubstituted diindolylmethane influxed by an OATP following a monotherapy with only the second composition.

Embodiment 180 provides the method of embodiment 176, wherein the percentage of a composition influxed by an OATP following the combination therapy is about 0.5% of the percentage of substituted or unsubstituted diindolylmethane influxed by an OATP following a monotherapy with only the second composition.

Embodiment 181 provides the method of embodiment 176, wherein the percentage of a composition influxed by an OATP following the combination therapy is about 0.6% of the percentage of substituted or unsubstituted diindolylmethane influxed by an OATP following a monotherapy with only the second composition.

Embodiment 182 provides the method of embodiment 176, wherein the percentage of a composition influxed by an OATP following the combination therapy is about 0.7% of the percentage of substituted or unsubstituted diindolylmethane influxed by an OATP following a monotherapy with only the second composition.

Embodiment 183 provides the method of embodiment 176, wherein the percentage of a composition influxed by an OATP following the combination therapy is about 0.8% of the percentage of substituted or unsubstituted diindolylmethane influxed by an OATP following a monotherapy with only the second composition.

Embodiment 184 provides the method of embodiment 176, wherein the percentage of a composition influxed by an OATP following the combination therapy is about 0.9% of the percentage of substituted or unsubstituted diindolylmethane influxed by an OATP following a monotherapy with only the second composition.

Embodiment 185 provides the method of embodiment 176, wherein the percentage of a composition influxed by an OATP following the combination therapy is about 1% of the percentage of substituted or unsubstituted diindolylmethane influxed by an OATP following a monotherapy with only the second composition.

Embodiment 186 provides the method of embodiment 176, wherein the percentage of a composition influxed by an OATP following the combination therapy is about 2% of the percentage of substituted or unsubstituted diindolylmethane influxed by an OATP following a monotherapy with only the second composition.

Embodiment 187 provides the method of embodiment 176, wherein the percentage of a composition influxed by an OATP following the combination therapy is about 3% of the percentage of substituted or unsubstituted diindolylmethane influxed by an OATP following a monotherapy with only the second composition.

Embodiment 188 provides the method of embodiment 176, wherein the percentage of a composition influxed by an OATP following the combination therapy is about 4% of the percentage of substituted or unsubstituted diindolylmethane influxed by an OATP following a monotherapy with only the second composition.

Embodiment 189 provides the method of embodiment 176, wherein the percentage of a composition influxed by an OATP following the combination therapy is about 5% of the percentage of substituted or unsubstituted diindolylmethane influxed by an OATP following a monotherapy with only the second composition.

Embodiment 190 provides the method of embodiment 176, wherein the percentage of a composition influxed by an OATP following the combination therapy is about 6% of the percentage of substituted or unsubstituted diindolylmethane influxed by an OATP following a monotherapy with only the second composition.

Embodiment 191 provides the method of embodiment 176, wherein the percentage of a composition influxed by an OATP following the combination therapy is about 7% of the percentage of substituted or unsubstituted diindolylmethane influxed by an OATP following a monotherapy with only the second composition.

Embodiment 192 provides the method of embodiment 176, wherein the percentage of a composition influxed by an OATP following the combination therapy is about 8% of the percentage of substituted or unsubstituted diindolylmethane influxed by an OATP following a monotherapy with only the second composition.

Embodiment 193 provides the method of embodiment 176, wherein the percentage of a composition influxed by an OATP following the combination therapy is about 9% of the percentage of substituted or unsubstituted diindolylmethane influxed by an OATP following a monotherapy with only the second composition.

Embodiment 194 provides the method of embodiment 176, wherein the percentage of a composition influxed by an OATP following the combination therapy is about 10% of the percentage of substituted or unsubstituted diindolylmethane influxed by an OATP following a monotherapy with only the second composition.

Embodiment 195 provides the method of embodiment 176, wherein the percentage of a composition influxed by an OATP following the combination therapy is about 20% of the percentage of substituted or unsubstituted diindolylmethane influxed by an OATP following a monotherapy with only the second composition.

Embodiment 196 provides the method of embodiment 176, wherein the percentage of a composition influxed by an OATP following the combination therapy is about 30% of the percentage of substituted or unsubstituted diindolylmethane influxed by an OATP following a monotherapy with only the second composition.

Embodiment 197 provides the method of embodiment 176, wherein the percentage of a composition influxed by an OATP following the combination therapy is about 40% of the percentage of substituted or unsubstituted diindolylmethane influxed by an OATP following a monotherapy with only the second composition.

Embodiment 198 provides the method of embodiment 176, wherein the percentage of a composition influxed by an OATP following the combination therapy is about 50% of the percentage of substituted or unsubstituted diindolylmethane influxed by an OATP following a monotherapy with only the second composition.

Embodiment 199 provides the method of any one of embodiments 176-198, wherein the second composition comprising a substituted or unsubstituted diindolylmethane is administered in a dosage comprising at least 15 mg of the substituted or unsubstituted diindolylmethane.

Embodiment 200 provides a method of treating rosacea in a subject in need thereof comprising a combination therapy comprising administering a first composition comprising modulators of one or more CYP450 enzymes and a second composition comprising a substituted or unsubstituted diindolylmethane.

Embodiment 201 provides the method of embodiment 200, wherein the combination therapy further comprises administering a third composition comprising a substituted or unsubstituted retinoic acid based component.

Embodiment 202 provides the method of embodiment 201, wherein the retinoic acid based component is Vitamin A.

Embodiment 203 provides the method of any one of embodiments 200-202, wherein the Vitamin A is contained in the second composition comprising a substituted or unsubstituted diindolylmethane.

Embodiment 204 provides the method of any one of embodiments 200-203, wherein the first and the second compositions are administered by oral route.

Embodiment 205 provides the method of any one of embodiments 200-204, wherein one or more doses of the first composition comprising modulators of one or more CYP450 enzymes is administered prior to administering the second composition comprising a substituted or unsubstituted diindolylmethane.

Embodiment 206 provides the method of any one of embodiments 200-205, wherein the one or more doses of the first composition are administered from about 1 day to about 21 days prior to the administering the second composition.

Embodiment 207 provides the method of any one of embodiments 200-205, wherein the one or more doses of the first composition are administered from about 1 hour to about 30 hours prior to the administering the second composition.

Embodiment 208 provides the method of any one of embodiments 200-205, wherein a first dose of the first composition is administered about 24 hours prior to administering the second composition and a second dose of the first composition is administered about 12 hours prior to administering the second composition.

Embodiment 209 provides the method of any one of embodiments 200-204, wherein the first and the second compositions are administered concurrently.

Embodiment 210 provides the method of any one of embodiments 200-209, wherein the first composition is administered to modulate one or more cytochrome P450 enzymes comprising CYP1A1, CYP1A2, CYP2D6, CYP2C8, CYP2C9, CYP3A4, CYP2C19, and CYP19A1.

Embodiment 211 provides the method of any one of embodiments 200-210, wherein the first composition comprises one or more of black raspberry, blueberry, ellagic acid, pomegranate, walnuts, blackcurrants, soy, soybean, black soybean, turmeric, apiaceous vegetable, cruciferous vegetables, allium vegetables, garden cress, watercress, yellow onion, kale, alfalfa sprouts, green beans, chili powder, daizein, garlic, apple, apricot, chamomile, peppermint, dandelion, green tea, black tea, rooibos tea, itadori tea, coffee, caffeine, caffeic acid, grapes, wine, peanuts, honey, medium-chain triglycerides, coconut and coconut oil, honeycomb, fish oil, rosemary, N-acetyl cysteine, chrysin, quercetin, resveratrol, myricetin, curcumin, curry powder, fish oil, rosemary, astaxanthin, algae, yeast, salmon, trout, krill, shrimp, crayfish, and chicory root.

Embodiment 212 provides the method of any one of embodiments 200-210, wherein the first composition is administered to inhibit one or more enzymes comprising CYP1A1, CYP1A2, CYP2D6, CYP2C8, CYP2C9, CYP3A4, CYP2C19, and CYP19A1.

Embodiment 213 provides the method of embodiment 212, wherein the first composition comprises one or more of black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, grapes, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin.

Embodiment 214 provides the method of embodiment 212, wherein the first composition comprises one or more of black raspberry, blueberry, ellagic acid, pomegranate, walnuts, blackcurrants, black soybean, turmeric, apiaceous vegetable, apple, apricot, yellow onion, kale, alfalfa sprouts, green beans, black tea, chili powder, daizein, soybean, garlic, chamomile, peppermint, dandelion, green tea, wine, peanuts, itadori tea, garden cress, watercress, honey, medium-chain triglycerides, coconut and coconut oil, honeycomb, allium vegetables, fish oil, rosemary, chicory root, rooibos tea, coffee, caffeine, caffeic acid, N-acetyl cysteine, chrysin, quercetin, resveratrol, and myricetin.

Embodiment 215 provides the method of any one of embodiments 200-210, wherein the first composition is administered to induce one or more enzymes CYP450 enzymes comprising CYP1A1, CYP1A2, CYP2D6, CYP2C8, CYP2C9, CYP2C19, and CYP19A1.

Embodiment 216 provides the method of embodiment 215, wherein the first composition comprises one or more of cruciferous vegetables, resveratrol, grapes, wine, peanuts, soy, itadori tea, green tea, black tea, curcumin, turmeric, curry powder, soybean, garlic, fish oil, rosemary, astaxanthin, algae, yeast, salmon, trout, krill, shrimp, crayfish, chicory root, quercertin, apple, apricot, blueberries, yellow onion, kale, alfalfa sprouts, green beans, broccoli, black tea, chili powder, and rooibos tea.

Embodiment 217 provides the method of any one of embodiments 200-216, wherein the combination therapy increases bioavailability of the substituted or unsubstituted diindolylmethane.

Embodiment 218 provides the method of embodiment 217, wherein the combination therapy increases the bioavailability of the substituted or unsubstituted diindolylmethane by from about 1-fold to about 1000-fold compared to a monotherapy with only the second composition.

Embodiment 219 provides the method of embodiment 217, wherein the combination therapy increases the bioavailability of the substituted or unsubstituted diindolylmethane by about 1-fold compared to a monotherapy with only the second composition.

Embodiment 220 provides the method of embodiment 217, wherein the combination therapy increases the bioavailability of the substituted or unsubstituted diindolylmethane by about 2-fold compared to a monotherapy with only the second composition.

Embodiment 221 provides the method of embodiment 217, wherein the combination therapy increases the bioavailability of the substituted or unsubstituted diindolylmethane by about 3-fold compared to a monotherapy with only the second composition.

Embodiment 222 provides the method of embodiment 217, wherein the combination therapy increases the bioavailability of the substituted or unsubstituted diindolylmethane by about 4-fold compared to a monotherapy with only the second composition.

Embodiment 223 provides the method of embodiment 217, wherein the combination therapy increases the bioavailability of the substituted or unsubstituted diindolylmethane by about 5-fold compared to a monotherapy with only the second composition.

Embodiment 224 provides the method of embodiment 217, wherein the combination therapy increases the bioavailability of the substituted or unsubstituted diindolylmethane by about 10-fold compared to a monotherapy with only the second composition.

Embodiment 225 provides the method of embodiment 217, wherein the combination therapy increases the bioavailability of the substituted or unsubstituted diindolylmethane by about 20-fold compared to a monotherapy with only the second composition.

Embodiment 226 provides the method of embodiment 217, wherein the combination therapy increases the bioavailability of the substituted or unsubstituted diindolylmethane by about 30-fold compared to a monotherapy with only the second composition.

Embodiment 227 provides the method of embodiment 217, wherein the combination therapy increases the bioavailability of the substituted or unsubstituted diindolylmethane by about 40-fold compared to a monotherapy with only the second composition.

Embodiment 228 provides the method of embodiment 217, wherein the combination therapy increases the bioavailability of the substituted or unsubstituted diindolylmethane by about 50-fold compared to a monotherapy with only the second composition.

Embodiment 229 provides the method of embodiment 217, wherein the combination therapy increases the bioavailability of the substituted or unsubstituted diindolylmethane by about 60-fold compared to a monotherapy with only the second composition.

Embodiment 230 provides the method of embodiment 217, wherein the combination therapy increases the bioavailability of the substituted or unsubstituted diindolylmethane by about 70-fold compared to a monotherapy with only the second composition.

Embodiment 231 provides the method of embodiment 217, wherein the combination therapy increases the bioavailability of the substituted or unsubstituted diindolylmethane by about 80-fold compared to a monotherapy with only the second composition.

Embodiment 232 provides the method of embodiment 217, wherein the combination therapy increases the bioavailability of the substituted or unsubstituted diindolylmethane by about 90-fold compared to a monotherapy with only the second composition.

Embodiment 233 provides the method of embodiment 217, wherein the combination therapy increases the bioavailability of the substituted or unsubstituted diindolylmethane by about 100-fold compared to a monotherapy with only the second composition.

Embodiment 234 provides the method of embodiment 217, wherein the combination therapy increases the bioavailability of the substituted or unsubstituted diindolylmethane by about 200-fold compared to a monotherapy with only the second composition.

Embodiment 235 provides the method of embodiment 217, wherein the combination therapy increases the bioavailability of the substituted or unsubstituted diindolylmethane by about 300-fold compared to a monotherapy with only the second composition.

Embodiment 236 provides the method of embodiment 217, wherein the combination therapy increases the bioavailability of the substituted or unsubstituted diindolylmethane by about 400-fold compared to a monotherapy with only the second composition.

Embodiment 237 provides the method of embodiment 217, wherein the combination therapy increases the bioavailability of the substituted or unsubstituted diindolylmethane by about 500-fold compared to a monotherapy with only the second composition.

Embodiment 238 provides the method of embodiment 217, wherein the combination therapy increases the bioavailability of the substituted or unsubstituted diindolylmethane by about 600-fold compared to a monotherapy with only the second composition.

Embodiment 239 provides the method of embodiment 217, wherein the combination therapy increases the bioavailability of the substituted or unsubstituted diindolylmethane by about 700-fold compared to a monotherapy with only the second composition.

Embodiment 240 provides the method of embodiment 217, wherein the combination therapy increases the bioavailability of the substituted or unsubstituted diindolylmethane by about 800-fold compared to a monotherapy with only the second composition.

Embodiment 241 provides the method of embodiment 217, wherein the combination therapy increases the bioavailability of the substituted or unsubstituted diindolylmethane by about 900-fold compared to a monotherapy with only the second composition.

Embodiment 242 provides the method of embodiment 217, wherein the combination therapy increases the bioavailability of the substituted or unsubstituted diindolylmethane by about 1000-fold compared to a monotherapy with only the second composition.

Embodiment 243 provides the method of any one of embodiments 217-242, wherein the second composition is administered at a dosage comprising at least 15 mg of the substituted or unsubstituted diindolylmethane.

Embodiment 244 provides the method of any one of embodiments 200-243, wherein the combination therapy increases Cmax of the substituted or unsubstituted diindolylmethane in plasma.

Embodiment 245 provides the method of embodiment 244, wherein the combination therapy increases the Cmax of the substituted or unsubstituted diindolylmethane in plasma by from about 1-fold to about 1000-fold compared to a monotherapy with only the first composition.

Embodiment 246 provides the method of embodiment 244, wherein the combination therapy increases the Cmax of the substituted or unsubstituted diindolylmethane by about 1-fold compared to a monotherapy with only the second composition.

Embodiment 247 provides the method of embodiment 244, wherein the combination therapy increases the Cmax of the substituted or unsubstituted diindolylmethane by about 2-fold compared to a monotherapy with only the second composition.

Embodiment 248 provides the method of embodiment 244, wherein the combination therapy increases the Cmax of the substituted or unsubstituted diindolylmethane by about 3-fold compared to a monotherapy with only the second composition.

Embodiment 249 provides the method of embodiment 244, wherein the combination therapy increases the Cmax of the substituted or unsubstituted diindolylmethane by about 4-fold compared to a monotherapy with only the second composition.

Embodiment 250 provides the method of embodiment 244, wherein the combination therapy increases the Cmax of the substituted or unsubstituted diindolylmethane by about 5-fold compared to a monotherapy with only the second composition.

Embodiment 251 provides the method of embodiment 244, wherein the combination therapy increases the Cmax of the substituted or unsubstituted diindolylmethane by about 10-fold compared to a monotherapy with only the second composition.

Embodiment 252 provides the method of embodiment 244, wherein the combination therapy increases the Cmax of the substituted or unsubstituted diindolylmethane by about 20-fold compared to a monotherapy with only the second composition.

Embodiment 253 provides the method of embodiment 244, wherein the combination therapy increases the Cmax of the substituted or unsubstituted diindolylmethane by about 30-fold compared to a monotherapy with only the second composition.

Embodiment 254 provides the method of embodiment 244, wherein the combination therapy increases the Cmax of the substituted or unsubstituted diindolylmethane by about 40-fold compared to a monotherapy with only the second composition.

Embodiment 255 provides the method of embodiment 244, wherein the combination therapy increases the Cmax of the substituted or unsubstituted diindolylmethane by about 50-fold compared to a monotherapy with only the second composition.

Embodiment 256 provides the method of embodiment 244, wherein the combination therapy increases the Cmax of the substituted or unsubstituted diindolylmethane by about 60-fold compared to a monotherapy with only the second composition.

Embodiment 257 provides the method of embodiment 244, wherein the combination therapy increases the Cmax of the substituted or unsubstituted diindolylmethane by about 70-fold compared to a monotherapy with only the second composition.

Embodiment 258 provides the method of embodiment 244, wherein the combination therapy increases the Cmax of the substituted or unsubstituted diindolylmethane by about 80-fold compared to a monotherapy with only the second composition.

Embodiment 259 provides the method of embodiment 244, wherein the combination therapy increases the Cmax of the substituted or unsubstituted diindolylmethane by about 90-fold compared to a monotherapy with only the second composition.

Embodiment 260 provides the method of embodiment 244, wherein the combination therapy increases the Cmax of the substituted or unsubstituted diindolylmethane by about 100-fold compared to a monotherapy with only the second composition.

Embodiment 261 provides the method of embodiment 244, wherein the combination therapy increases the Cmax of the substituted or unsubstituted diindolylmethane by about 200-fold compared to a monotherapy with only the second composition.

Embodiment 262 provides the method of embodiment 244, wherein the combination therapy increases the Cmax of the substituted or unsubstituted diindolylmethane by about 300-fold compared to a monotherapy with only the second composition.

Embodiment 263 provides the method of embodiment 244, wherein the combination therapy increases the Cmax of the substituted or unsubstituted diindolylmethane by about 400-fold compared to a monotherapy with only the second composition.

Embodiment 264 provides the method of embodiment 244, wherein the combination therapy increases the Cmax of the substituted or unsubstituted diindolylmethane by about 500-fold compared to a monotherapy with only the second composition.

Embodiment 265 provides the method of embodiment 244, wherein the combination therapy increases the Cmax of the substituted or unsubstituted diindolylmethane by about 600-fold compared to a monotherapy with only the second composition.

Embodiment 266 provides the method of embodiment 244, wherein the combination therapy increases the Cmax of the substituted or unsubstituted diindolylmethane by about 700-fold compared to a monotherapy with only the second composition.

Embodiment 267 provides the method of embodiment 244, wherein the combination therapy increases the Cmax of the substituted or unsubstituted diindolylmethane by about 800-fold compared to a monotherapy with only the second composition.

Embodiment 268 provides the method of embodiment 244, wherein the combination therapy increases the Cmax of the substituted or unsubstituted diindolylmethane by about 900-fold compared to a monotherapy with only the second composition.

Embodiment 269 provides the method of embodiment 244, wherein the combination therapy increases the Cmax of the substituted or unsubstituted diindolylmethane by about 1000-fold compared to a monotherapy with only the second composition.

Embodiment 270 provides the method of any one of embodiments 244-269, wherein the second composition is administered at a dosage comprising at least 15 mg of the substituted or unsubstituted diindolylmethane.

Embodiment 271 provides the method of any one of embodiments 200-270, wherein the combination therapy increases AUC of the substituted or unsubstituted diindolylmethane in plasma.

Embodiment 272 provides the method of embodiment 271, wherein the combination therapy increases the AUC of the substituted or unsubstituted diindolylmethane in plasma by from about 1-fold to about 1000-fold compared to a monotherapy with only the second composition.

Embodiment 273 provides the method of embodiment 271, wherein the combination therapy increases the AUC of the substituted or unsubstituted diindolylmethane by about 1-fold compared to a monotherapy with only the second composition.

Embodiment 274 provides the method of embodiment 271, wherein the combination therapy increases the AUC of the substituted or unsubstituted diindolylmethane by about 2-fold compared to a monotherapy with only the second composition.

Embodiment 275 provides the method of embodiment 271, wherein the combination therapy increases the AUC of the substituted or unsubstituted diindolylmethane by about 3-fold compared to a monotherapy with only the second composition.

Embodiment 276 provides the method of embodiment 271, wherein the combination therapy increases the AUC of the substituted or unsubstituted diindolylmethane by about 4-fold compared to a monotherapy with only the second composition.

Embodiment 277 provides the method of embodiment 271, wherein the combination therapy increases the AUC of the substituted or unsubstituted diindolylmethane by about 5-fold compared to a monotherapy with only the second composition.

Embodiment 278 provides the method of embodiment 271, wherein the combination therapy increases the AUC of the substituted or unsubstituted diindolylmethane by about 10-fold compared to a monotherapy with only the second composition.

Embodiment 279 provides the method of embodiment 271, wherein the combination therapy increases the AUC of the substituted or unsubstituted diindolylmethane by about 20-fold compared to a monotherapy with only the second composition.

Embodiment 280 provides the method of embodiment 271, wherein the combination therapy increases the AUC of the substituted or unsubstituted diindolylmethane by about 30-fold compared to a monotherapy with only the second composition.

Embodiment 281 provides the method of embodiment 271, wherein the combination therapy increases the AUC of the substituted or unsubstituted diindolylmethane by about 40-fold compared to a monotherapy with only the second the.

Embodiment 282 provides the method of embodiment 271, wherein the combination therapy increases the AUC of the substituted or unsubstituted diindolylmethane by about 50-fold compared to a monotherapy with only the second composition.

Embodiment 283 provides the method of embodiment 271, wherein the combination therapy increases the AUC of the substituted or unsubstituted diindolylmethane by about 60-fold compared to a monotherapy with only the second composition.

Embodiment 284 provides the method of embodiment 271, wherein the combination therapy increases the AUC of the substituted or unsubstituted diindolylmethane by about 70-fold compared to a monotherapy with only the second composition.

Embodiment 285 provides the method of embodiment 271, wherein the combination therapy increases the AUC of the substituted or unsubstituted diindolylmethane by about 80-fold compared to a monotherapy with only the second composition.

Embodiment 286 provides the method of embodiment 271, wherein the combination therapy increases the AUC of the substituted or unsubstituted diindolylmethane by about 90-fold compared to a monotherapy with only the second composition.

Embodiment 287 provides the method of embodiment 271, wherein the combination therapy increases the AUC of the substituted or unsubstituted diindolylmethane by about 100-fold compared to a monotherapy with only the second composition.

Embodiment 288 provides the method of embodiment 271, wherein the combination therapy increases the AUC of the substituted or unsubstituted diindolylmethane by about 200-fold compared to a monotherapy with only the second composition.

Embodiment 289 provides the method of embodiment 271, wherein the combination therapy increases the AUC of the substituted or unsubstituted diindolylmethane by about 300-fold compared to a monotherapy with only the second composition.

Embodiment 290 provides the method of embodiment 271, wherein the combination therapy increases the AUC of the substituted or unsubstituted diindolylmethane by about 400-fold compared to a monotherapy with only the second composition.

Embodiment 291 provides the method of embodiment 271, wherein the combination therapy increases the AUC of the substituted or unsubstituted diindolylmethane by about 500-fold compared to a monotherapy with only the second composition.

Embodiment 292 provides the method of embodiment 271, wherein the combination therapy increases the AUC of the substituted or unsubstituted diindolylmethane by about 600-fold compared to a monotherapy with only the second composition.

Embodiment 293 provides the method of embodiment 271, wherein the combination therapy increases the AUC of the substituted or unsubstituted diindolylmethane by about 700-fold compared to a monotherapy with only the second composition.

Embodiment 294 provides the method of embodiment 271, wherein the combination therapy increases the AUC of the substituted or unsubstituted diindolylmethane by about 800-fold compared to a monotherapy with only the second composition.

Embodiment 295 provides the method of embodiment 271, wherein the combination therapy increases the AUC of the substituted or unsubstituted diindolylmethane by about 900-fold compared to a monotherapy with only the second composition.

Embodiment 296 provides the method of embodiment 271, wherein the combination therapy increases the AUC of the substituted or unsubstituted diindolylmethane by about 1000-fold compared to a monotherapy with only the second composition.

Embodiment 297 provides the method of any one of embodiments 271-296, wherein the second composition is administered at a dosage comprising at least 15 mg of the substituted or unsubstituted diindolylmethane.

Embodiment 298 provides the method of any one of embodiments 200-297, wherein the combination therapy decreases Tmax of the substituted or unsubstituted diindolylmethane in plasma.

Embodiment 299 provides the method of embodiment 298, wherein the combination therapy decreases the Tmax of the substituted or unsubstituted diindolylmethane in plasma by from about 1-fold to about 1000-fold compared to a monotherapy with only the second composition.

Embodiment 300 provides the method of embodiment 298, wherein the combination therapy decreases the Tmax of the substituted or unsubstituted diindolylmethane by about 1-fold compared to a monotherapy with only the second composition.

Embodiment 301 provides the method of embodiment 298, wherein the combination therapy decreases the Tmax of the substituted or unsubstituted diindolylmethane by about 2-fold compared to a monotherapy with only the second composition.

Embodiment 302 provides the method of embodiment 298, wherein the combination therapy decreases the Tmax of the substituted or unsubstituted diindolylmethane by about 3-fold compared to a monotherapy with only the second composition.

Embodiment 303 provides the method of embodiment 298, wherein the combination therapy decreases the Tmax of the substituted or unsubstituted diindolylmethane by about 4-fold compared to a monotherapy with only the second composition.

Embodiment 304 provides the method of embodiment 298, wherein the combination therapy decreases the Tmax of the substituted or unsubstituted diindolylmethane by about 5-fold compared to a monotherapy with only the second composition.

Embodiment 305 provides the method of embodiment 298, wherein the combination therapy decreases the Tmax of the substituted or unsubstituted diindolylmethane by about 10-fold compared to a monotherapy with only the second composition.

Embodiment 306 provides the method of embodiment 298, wherein the combination therapy decreases the Tmax of the substituted or unsubstituted diindolylmethane by about 20-fold compared to a monotherapy with only the second composition.

Embodiment 307 provides the method of embodiment 298, wherein the combination therapy decreases the Tmax of the substituted or unsubstituted diindolylmethane by about 30-fold compared to a monotherapy with only the second composition.

Embodiment 308 provides the method of embodiment 298, wherein the combination therapy decreases the Tmax of the substituted or unsubstituted diindolylmethane by about 40-fold compared to a monotherapy with only the second composition.

Embodiment 309 provides the method of embodiment 298, wherein the combination therapy decreases the Tmax of the substituted or unsubstituted diindolylmethane by about 50-fold compared to a monotherapy with only the second composition.

Embodiment 310 provides the method of embodiment 298, wherein the combination therapy decreases the Tmax of the substituted or unsubstituted diindolylmethane by about 60-fold compared to a monotherapy with only the second composition.

Embodiment 311 provides the method of embodiment 298, wherein the combination therapy decreases the Tmax of the substituted or unsubstituted diindolylmethane by about 70-fold compared to a monotherapy with only the second composition.

Embodiment 312 provides the method of embodiment 298, wherein the combination therapy decreases the Tmax of the substituted or unsubstituted diindolylmethane by about 80-fold compared to a monotherapy with only the second composition.

Embodiment 313 provides the method of embodiment 298, wherein the combination therapy decreases the Tmax of the substituted or unsubstituted diindolylmethane by about 90-fold compared to a monotherapy with only the second composition.

Embodiment 314 provides the method of embodiment 298, wherein the combination therapy decreases the Tmax of the substituted or unsubstituted diindolylmethane by about 100-fold compared to a monotherapy with only the second composition.

Embodiment 315 provides the method of embodiment 298, wherein the combination therapy decreases the Tmax of the substituted or unsubstituted diindolylmethane by about 200-fold compared to a monotherapy with only the second composition.

Embodiment 316 provides the method of embodiment 298, wherein the combination therapy decreases the Tmax of the substituted or unsubstituted diindolylmethane by about 300-fold compared to a monotherapy with only the second composition.

Embodiment 317 provides the method of embodiment 298, wherein the combination therapy decreases the Tmax of the substituted or unsubstituted diindolylmethane by about 400-fold compared to a monotherapy with only the second composition.

Embodiment 318 provides the method of embodiment 298, wherein the combination therapy decreases the Tmax of the substituted or unsubstituted diindolylmethane by about 500-fold compared to a monotherapy with only the second composition.

Embodiment 319 provides the method of embodiment 298, wherein the combination therapy decreases the Tmax of the substituted or unsubstituted diindolylmethane by about 600-fold compared to a monotherapy with only the second composition.

Embodiment 320 provides the method of embodiment 298, wherein the combination therapy decreases the Tmax of the substituted or unsubstituted diindolylmethane by about 700-fold compared to a monotherapy with only the second composition.

Embodiment 321 provides the method of embodiment 298, wherein the combination therapy decreases the Tmax of the substituted or unsubstituted diindolylmethane by about 800-fold compared to a monotherapy with only the second composition.

Embodiment 322 provides the method of embodiment 298, wherein the combination therapy decreases the Tmax of the substituted or unsubstituted diindolylmethane by about 900-fold compared to a monotherapy with only the second composition.

Embodiment 323 provides the method of embodiment 298, wherein the combination therapy decreases the Tmax of the substituted or unsubstituted diindolylmethane by about 1000-fold compared to a monotherapy with only the second composition.

Embodiment 324 provides the method of any one of embodiments 298-323, wherein the second composition is administered at a dosage comprising at least 15 mg of the substituted or unsubstituted diindolylmethane.

Embodiment 325 provides the method of any one of embodiments 200-324, wherein the percentage of substituted or unsubstituted diindolylmethane effluxed by P-gp following the combination therapy is from about 0.1% to about 50% of the percentage of substituted or unsubstituted diindolylmethane effluxed by P-gp following a monotherapy with only the first composition.

Embodiment 326 provides the method of embodiment 325, wherein the percentage of substituted or unsubstituted diindolylmethane effluxed by P-gp following the combination therapy is about 0.1% of the percentage of substituted or unsubstituted diindolylmethane effluxed by P-gp following a monotherapy with only the second composition.

Embodiment 327 provides the method of embodiment 325, wherein the percentage of substituted or unsubstituted diindolylmethane effluxed by P-gp following the combination therapy is about 0.2% of the percentage of substituted or unsubstituted diindolylmethane effluxed by P-gp following a monotherapy with only the second composition.

Embodiment 328 provides the method of embodiment 325, wherein the percentage of substituted or unsubstituted diindolylmethane effluxed by P-gp following the combination therapy is about 0.3% of the percentage of substituted or unsubstituted diindolylmethane effluxed by P-gp following a monotherapy with only the second composition.

Embodiment 329 provides the method of embodiment 325, wherein the percentage of substituted or unsubstituted diindolylmethane effluxed by P-gp following the combination therapy is about 0.4% of the percentage of substituted or unsubstituted diindolylmethane effluxed by P-gp following a monotherapy with only the second composition.

Embodiment 330 provides the method of embodiment 325, wherein the percentage of substituted or unsubstituted diindolylmethane effluxed by P-gp following the combination therapy is about 0.5% of the percentage of substituted or unsubstituted diindolylmethane effluxed by P-gp following a monotherapy with only the second composition.

Embodiment 331 provides the method of embodiment 325, wherein the percentage of substituted or unsubstituted diindolylmethane effluxed by P-gp following the combination therapy is about 0.6% of the percentage of substituted or unsubstituted diindolylmethane effluxed by P-gp following a monotherapy with only the second composition.

Embodiment 332 provides the method of embodiment 325, wherein the percentage of substituted or unsubstituted diindolylmethane effluxed by P-gp following the combination therapy is about 0.7% of the percentage of substituted or unsubstituted diindolylmethane effluxed by P-gp following a monotherapy with only the second composition.

Embodiment 333 provides the method of embodiment 325, wherein the percentage of substituted or unsubstituted diindolylmethane effluxed by P-gp following the combination therapy is about 0.8% of the percentage of substituted or unsubstituted diindolylmethane effluxed by P-gp following a monotherapy with only the second composition.

Embodiment 334 provides the method of embodiment 325, wherein the percentage of substituted or unsubstituted diindolylmethane effluxed by P-gp following the combination therapy is about 0.9% of the percentage of substituted or unsubstituted diindolylmethane effluxed by P-gp following a monotherapy with only the second composition.

Embodiment 335 provides the method of embodiment 325, wherein the percentage of substituted or unsubstituted diindolylmethane effluxed by P-gp following the combination therapy is about 1% of the percentage of substituted or unsubstituted diindolylmethane effluxed by P-gp following a monotherapy with only the second composition.

Embodiment 336 provides the method of embodiment 325, wherein the percentage of substituted or unsubstituted diindolylmethane effluxed by P-gp following the combination therapy is about 2% of the percentage of substituted or unsubstituted diindolylmethane effluxed by P-gp following a monotherapy with only the second composition.

Embodiment 337 provides the method of embodiment 325, wherein the percentage of substituted or unsubstituted diindolylmethane effluxed by P-gp following the combination therapy is about 3% of the percentage of substituted or unsubstituted diindolylmethane effluxed by P-gp following a monotherapy with only the second composition.

Embodiment 338 provides the method of embodiment 325, wherein the percentage of substituted or unsubstituted diindolylmethane effluxed by P-gp following the combination therapy is about 4% of the percentage of substituted or unsubstituted diindolylmethane effluxed by P-gp following a monotherapy with only the second composition.

Embodiment 339 provides the method of embodiment 325, wherein the percentage of substituted or unsubstituted diindolylmethane effluxed by P-gp following the combination therapy is about 5% of the percentage of substituted or unsubstituted diindolylmethane effluxed by P-gp following a monotherapy with only the second composition.

Embodiment 340 provides the method of embodiment 325, wherein the percentage of substituted or unsubstituted diindolylmethane effluxed by P-gp following the combination therapy is about 6% of the percentage of substituted or unsubstituted diindolylmethane effluxed by P-gp following a monotherapy with only the second composition.

Embodiment 341 provides the method of embodiment 325, wherein the percentage of substituted or unsubstituted diindolylmethane effluxed by P-gp following the combination therapy is about 7% of the percentage of substituted or unsubstituted diindolylmethane effluxed by P-gp following a monotherapy with only the second composition.

Embodiment 342 provides the method of embodiment 325, wherein the percentage of substituted or unsubstituted diindolylmethane effluxed by P-gp following the combination therapy is about 8% of the percentage of substituted or unsubstituted diindolylmethane effluxed by P-gp following a monotherapy with only the second composition.

Embodiment 343 provides the method of embodiment 325, wherein the percentage of substituted or unsubstituted diindolylmethane effluxed by P-gp following the combination therapy is about 9% of the percentage of substituted or unsubstituted diindolylmethane effluxed by P-gp following a monotherapy with only the second composition.

Embodiment 344 provides the method of embodiment 325, wherein the percentage of substituted or unsubstituted diindolylmethane effluxed by P-gp following the combination therapy is about 10% of the percentage of substituted or unsubstituted diindolylmethane effluxed by P-gp following a monotherapy with only the second composition.

Embodiment 345 provides the method of embodiment 325, wherein the percentage of substituted or unsubstituted diindolylmethane effluxed by P-gp following the combination therapy is about 20% of the percentage of substituted or unsubstituted diindolylmethane effluxed by P-gp following a monotherapy with only the second composition.

Embodiment 346 provides the method of embodiment 325, wherein the percentage of substituted or unsubstituted diindolylmethane effluxed by P-gp following the combination therapy is about 30% of the percentage of substituted or unsubstituted diindolylmethane effluxed by P-gp following a monotherapy with only the second composition.

Embodiment 347 provides the method of embodiment 325, wherein the percentage of substituted or unsubstituted diindolylmethane effluxed by P-gp following the combination therapy is about 40% of the percentage of substituted or unsubstituted diindolylmethane effluxed by P-gp following a monotherapy with only the second composition.

Embodiment 348 provides the method of embodiment 325, wherein the percentage of substituted or unsubstituted diindolylmethane effluxed by P-gp following the combination therapy is about 50% of the percentage of substituted or unsubstituted diindolylmethane effluxed by P-gp following a monotherapy with only the second composition.

Embodiment 349 provides the method of any one of embodiments 325-348, wherein the second composition is administered at a dosage comprising at least 15 mg of the substituted or unsubstituted diindolylmethane.

Embodiment 350 provides the method of any one of embodiments 200-349, wherein the percentage of substituted or unsubstituted diindolylmethane metabolized by CYP450 enzymes following the combination therapy is about 0.1% to about 50% of the percentage of substituted or unsubstituted diindolylmethane metabolized by CYP450 enzymes following a monotherapy with only the second composition.

Embodiment 351 provides the method of embodiment 350, wherein the percentage of substituted or unsubstituted diindolylmethane metabolized by CYP450 enzymes following the combination therapy is about 0.1% of the percentage of substituted or unsubstituted diindolylmethane metabolized by CYP450 enzymes following a monotherapy with only the second composition.

Embodiment 352 provides the method of embodiment 350, wherein the percentage of substituted or unsubstituted diindolylmethane metabolized by CYP450 enzymes following the combination therapy is about 0.2% of the percentage of substituted or unsubstituted diindolylmethane metabolized by CYP450 enzymes following a monotherapy with only the second composition.

Embodiment 353 provides the method of embodiment 350, wherein the percentage of substituted or unsubstituted diindolylmethane metabolized by CYP450 enzymes following the combination therapy is about 0.3% of the percentage of substituted or unsubstituted diindolylmethane metabolized by CYP450 enzymes following a monotherapy with only the second composition.

Embodiment 354 provides the method of embodiment 350, wherein the percentage of substituted or unsubstituted diindolylmethane metabolized by CYP450 enzymes following the combination therapy is about 0.4% of the percentage of substituted or unsubstituted diindolylmethane metabolized by CYP450 enzymes following a monotherapy with only the second composition.

Embodiment 355 provides the method of embodiment 350, wherein the percentage of substituted or unsubstituted diindolylmethane metabolized by CYP450 enzymes following the combination therapy is about 0.5% of the percentage of substituted or unsubstituted diindolylmethane metabolized by CYP450 enzymes following a monotherapy with only the second composition.

Embodiment 356 provides the method of embodiment 350, wherein the percentage of substituted or unsubstituted diindolylmethane metabolized by CYP450 enzymes following the combination therapy is about 0.6% of the percentage of substituted or unsubstituted diindolylmethane metabolized by CYP450 enzymes following a monotherapy with only the second composition.

Embodiment 357 provides the method of embodiment 350, wherein the percentage of substituted or unsubstituted diindolylmethane metabolized by CYP450 enzymes following the combination therapy is about 0.7% of the percentage of substituted or unsubstituted diindolylmethane metabolized by CYP450 enzymes following a monotherapy with only the second composition.

Embodiment 358 provides the method of embodiment 350, wherein the percentage of substituted or unsubstituted diindolylmethane metabolized by CYP450 enzymes following the combination therapy is about 0.8% of the percentage of substituted or unsubstituted diindolylmethane metabolized by CYP450 enzymes following a monotherapy with only the second composition.

Embodiment 359 provides the method of embodiment 350, wherein the percentage of substituted or unsubstituted diindolylmethane metabolized by CYP450 enzymes following the combination therapy is about 0.9% of the percentage of substituted or unsubstituted diindolylmethane metabolized by CYP450 enzymes following a monotherapy with only the second composition.

Embodiment 360 provides the method of embodiment 350, wherein the percentage of substituted or unsubstituted diindolylmethane metabolized by CYP450 enzymes following the combination therapy is about 1% of the percentage of substituted or unsubstituted diindolylmethane metabolized by CYP450 enzymes following a monotherapy with only the second composition.

Embodiment 361 provides the method of embodiment 350, wherein the percentage of substituted or unsubstituted diindolylmethane metabolized by CYP450 enzymes following the combination therapy is about 2% of the percentage of substituted or unsubstituted diindolylmethane metabolized by CYP450 enzymes following a monotherapy with only the second composition.

Embodiment 362 provides the method of embodiment 350, wherein the percentage of substituted or unsubstituted diindolylmethane metabolized by CYP450 enzymes following the combination therapy is about 3% of the percentage of substituted or unsubstituted diindolylmethane metabolized by CYP450 enzymes following a monotherapy with only the second composition.

Embodiment 363 provides the method of embodiment 350, wherein the percentage of substituted or unsubstituted diindolylmethane metabolized by CYP450 enzymes following the combination therapy is about 4% of the percentage of substituted or unsubstituted diindolylmethane metabolized by CYP450 enzymes following a monotherapy with only the second composition.

Embodiment 364 provides the method of embodiment 350, wherein the percentage of substituted or unsubstituted diindolylmethane metabolized by CYP450 enzymes following the combination therapy is about 5% of the percentage of substituted or unsubstituted diindolylmethane metabolized by CYP450 enzymes following a monotherapy with only the second composition.

Embodiment 365 provides the method of embodiment 350, wherein the percentage of substituted or unsubstituted diindolylmethane metabolized by CYP450 enzymes following the combination therapy is about 6% of the percentage of substituted or unsubstituted diindolylmethane metabolized by CYP450 enzymes following a monotherapy with only the second composition.

Embodiment 366 provides the method of embodiment 350, wherein the percentage of substituted or unsubstituted diindolylmethane metabolized by CYP450 enzymes following the combination therapy is about 7% of the percentage of substituted or unsubstituted diindolylmethane metabolized by CYP450 enzymes following a monotherapy with only the second composition.

Embodiment 367 provides the method of embodiment 350, wherein the percentage of substituted or unsubstituted diindolylmethane metabolized by CYP450 enzymes following the combination therapy is about 8% of the percentage of substituted or unsubstituted diindolylmethane metabolized by CYP450 enzymes following a monotherapy with only the second composition.

Embodiment 368 provides the method of embodiment 350, wherein the percentage of substituted or unsubstituted diindolylmethane metabolized by CYP450 enzymes following the combination therapy is about 9% of the percentage of substituted or unsubstituted diindolylmethane metabolized by CYP450 enzymes following a monotherapy with only the second composition.

Embodiment 369 provides the method of embodiment 350, wherein the percentage of substituted or unsubstituted diindolylmethane metabolized by CYP450 enzymes following the combination therapy is about 10% of the percentage of substituted or unsubstituted diindolylmethane metabolized by CYP450 enzymes following a monotherapy with only the second composition.

Embodiment 370 provides the method of embodiment 350, wherein the percentage of substituted or unsubstituted diindolylmethane metabolized by CYP450 enzymes following the combination therapy is about 20% of the percentage of substituted or unsubstituted diindolylmethane metabolized by CYP450 enzymes following a monotherapy with only the second composition.

Embodiment 371 provides the method of embodiment 350, wherein the percentage of substituted or unsubstituted diindolylmethane metabolized by CYP450 enzymes following the combination therapy is about 30% of the percentage of substituted or unsubstituted diindolylmethane metabolized by CYP450 enzymes following a monotherapy with only the second composition.

Embodiment 372 provides the method of embodiment 350, wherein the percentage of substituted or unsubstituted diindolylmethane metabolized by CYP450 enzymes following the combination therapy is about 40% of the percentage of substituted or unsubstituted diindolylmethane metabolized by CYP450 enzymes following a monotherapy with only the second composition.

Embodiment 373 provides the method of embodiment 350, wherein the percentage of substituted or unsubstituted diindolylmethane metabolized by CYP450 enzymes following the combination therapy is about 50% of the percentage of substituted or unsubstituted diindolylmethane metabolized by CYP450 enzymes following a monotherapy with only the second composition.

Embodiment 374 provides the method of any one of embodiments 350-373, wherein the second composition is administered at a dosage comprising at least 15 mg of the substituted or unsubstituted diindolylmethane.

Embodiment 375 provides the method of any one of embodiments 200-374, wherein the percentage of a composition influxed by an OATP following the combination therapy is about 0.1% to about 50% of the percentage of substituted or unsubstituted diindolylmethane influxed by an OATP following a monotherapy with only the second composition.

Embodiment 376 provides the method of embodiment 375, wherein the percentage of a composition influxed by an OATP following the combination therapy is about 0.2% of the percentage of substituted or unsubstituted diindolylmethane influxed by an OATP following a monotherapy with only the second composition.

Embodiment 377 provides the method of embodiment 375, wherein the percentage of a composition influxed by an OATP following the combination therapy is about 0.3% of the percentage of substituted or unsubstituted diindolylmethane influxed by an OATP following a monotherapy with only the second composition.

Embodiment 378 provides the method of embodiment 375, wherein the percentage of a composition influxed by an OATP following the combination therapy is about 0.4% of the percentage of substituted or unsubstituted diindolylmethane influxed by an OATP following a monotherapy with only the second composition.

Embodiment 379 provides the method of embodiment 375, wherein the percentage of a composition influxed by an OATP following the combination therapy is about 0.5% of the percentage of substituted or unsubstituted diindolylmethane influxed by an OATP following a monotherapy with only the second composition.

Embodiment 380 provides the method of embodiment 375, wherein the percentage of a composition influxed by an OATP following the combination therapy is about 0.6% of the percentage of substituted or unsubstituted diindolylmethane influxed by an OATP following a monotherapy with only the second composition.

Embodiment 381 provides the method of embodiment 375, wherein the percentage of a composition influxed by an OATP following the combination therapy is about 0.7% of the percentage of substituted or unsubstituted diindolylmethane influxed by an OATP following a monotherapy with only the second composition.

Embodiment 382 provides the method of embodiment 375, wherein the percentage of a composition influxed by an OATP following the combination therapy is about 0.8% of the percentage of substituted or unsubstituted diindolylmethane influxed by an OATP following a monotherapy with only the second composition.

Embodiment 383 provides the method of embodiment 375, wherein the percentage of a composition influxed by an OATP following the combination therapy is about 0.9% of the percentage of substituted or unsubstituted diindolylmethane influxed by an OATP following a monotherapy with only the second composition.

Embodiment 384 provides the method of embodiment 375, wherein the percentage of a composition influxed by an OATP following the combination therapy is about 1% of the percentage of substituted or unsubstituted diindolylmethane influxed by an OATP following a monotherapy with only the second composition.

Embodiment 385 provides the method of embodiment 375, wherein the percentage of a composition influxed by an OATP following the combination therapy is about 2% of the percentage of substituted or unsubstituted diindolylmethane influxed by an OATP following a monotherapy with only the second composition.

Embodiment 386 provides the method of embodiment 375, wherein the percentage of a composition influxed by an OATP following the combination therapy is about 3% of the percentage of substituted or unsubstituted diindolylmethane influxed by an OATP following a monotherapy with only the second composition.

Embodiment 387 provides the method of embodiment 375, wherein the percentage of a composition influxed by an OATP following the combination therapy is about 4% of the percentage of substituted or unsubstituted diindolylmethane influxed by an OATP following a monotherapy with only the second composition.

Embodiment 388 provides the method of embodiment 375, wherein the percentage of a composition influxed by an OATP following the combination therapy is about 5% of the percentage of substituted or unsubstituted diindolylmethane influxed by an OATP following a monotherapy with only the second composition.

Embodiment 389 provides the method of embodiment 375, wherein the percentage of a composition influxed by an OATP following the combination therapy is about 6% of the percentage of substituted or unsubstituted diindolylmethane influxed by an OATP following a monotherapy with only the second composition.

Embodiment 390 provides the method of embodiment 375, wherein the percentage of a composition influxed by an OATP following the combination therapy is about 7% of the percentage of substituted or unsubstituted diindolylmethane influxed by an OATP following a monotherapy with only the second composition.

Embodiment 391 provides the method of embodiment 375, wherein the percentage of a composition influxed by an OATP following the combination therapy is about 8% of the percentage of substituted or unsubstituted diindolylmethane influxed by an OATP following a monotherapy with only the second composition.

Embodiment 392 provides the method of embodiment 375, wherein the percentage of a composition influxed by an OATP following the combination therapy is about 9% of the percentage of substituted or unsubstituted diindolylmethane influxed by an OATP following a monotherapy with only the second composition.

Embodiment 393 provides the method of embodiment 375, wherein the percentage of a composition influxed by an OATP following the combination therapy is about 10% of the percentage of substituted or unsubstituted diindolylmethane influxed by an OATP following a monotherapy with only the second composition.

Embodiment 394 provides the method of embodiment 375, wherein the percentage of a composition influxed by an OATP following the combination therapy is about 20% of the percentage of substituted or unsubstituted diindolylmethane influxed by an OATP following a monotherapy with only the second composition.

Embodiment 395 provides the method of embodiment 375, wherein the percentage of a composition influxed by an OATP following the combination therapy is about 30% of the percentage of substituted or unsubstituted diindolylmethane influxed by an OATP following a monotherapy with only the second composition.

Embodiment 396 provides the method of embodiment 375, wherein the percentage of a composition influxed by an OATP following the combination therapy is about 40% of the percentage of substituted or unsubstituted diindolylmethane influxed by an OATP following a monotherapy with only the second composition.

Embodiment 397 provides the method of embodiment 375, wherein the percentage of a composition influxed by an OATP following the combination therapy is about 50% of the percentage of substituted or unsubstituted diindolylmethane influxed by an OATP following a monotherapy with only the second composition.

Embodiment 398 provides the method of any one of embodiments 375-397, wherein the second composition comprising a substituted or unsubstituted diindolylmethane is administered in a dosage comprising at least 15 mg of the substituted or unsubstituted diindolylmethane.

What is claimed is:

1. A pharmaceutical composition for treating acne, the composition comprising a first component comprising an inhibitor of a CYP450 enzyme and a second component comprising a substituted or unsubstituted diindolylmethane, wherein the first component and the second component are in separated unit dosage form for sequential administration, wherein the first component comprises about 100 mg to about 1000 mg of the inhibitor of the CYP450 enzyme, and wherein the second component comprises about 15 mg to about 100 mg of the substituted or unsubstituted diindolylmethane, and wherein a weight ratio between the inhibitor of the CYP450 enzyme and the substituted or unsubstituted diindolylmethane is between about 15:1 and about 10:1.

2. The pharmaceutical composition of claim 1, further comprising a third component comprising a substituted or unsubstituted retinoic acid based compound.

3. The pharmaceutical composition of claim 2, wherein the third component comprises about 100 µg to about 1000 µg of the substituted or unsubstituted retinoic acid based compound.

4. The pharmaceutical composition of claim 1, wherein the CYP450 enzyme comprises CYP1A2 and the first component comprises an inhibitor of the CYP1A2.

5. The pharmaceutical composition of claim 4, wherein the inhibitor of the CYP1A2 comprises quercetin.

6. The pharmaceutical composition of claim 4, wherein the first component comprises about 100 mg to about 1000 mg of the modulator of the CYP1A2.

7. The pharmaceutical composition of claim 5, wherein the first component comprises about 100 mg to about 1000 mg of the quercetin.

8. The pharmaceutical composition of claim 5, wherein the first component comprises about 400 mg to about 500 mg of the quercetin.

9. The pharmaceutical composition of claim 8, wherein the second component comprises about 30 mg to about 100 mg of the substituted or unsubstituted diindolylmethane.

10. The pharmaceutical composition of claim 9, wherein the second component comprises about 45 mg of the substituted or unsubstituted diindolylmethane.

11. The pharmaceutical composition of claim 10, further comprising a third component comprising a substituted or unsubstituted retinoic acid based compound.

12. The pharmaceutical composition of claim 11, wherein the third component comprises about 100 µg to about 1000 µg of the substituted or unsubstituted retinoic acid based compound.

13. The pharmaceutical composition of claim 1, wherein percentage of the substituted or unsubstituted diindolylmethane metabolized by the CYP450 enzyme is reduced by about 0.1% to about 10% compared to a control composition that does not comprise the first component.

14. The pharmaceutical composition of claim 5, wherein the metabolism of the substituted or unsubstituted diindolylmethane by the CYP1A2 is reduced by about 0.1% to about 10% compared to a control composition that does not comprise the quercetin.

15. The pharmaceutical composition of claim 5, wherein bioavailability of the substituted or unsubstituted diindolylmethane is increased by about 1-fold to about 100-folds compared to a control composition that does not comprise the quercetin.

16. The pharmaceutical composition of claim 5, wherein a weight ratio between the quercetin and the substituted or unsubstituted diindolylmethane is between about 15:1 and 10:1.

17. The pharmaceutical composition of claim 5, wherein a weight ratio between the quercetin and the substituted or unsubstituted diindolylmethane is about 11:1.

* * * * *